US010849879B2

(12) United States Patent
Seward

(10) Patent No.: US 10,849,879 B2
(45) Date of Patent: Dec. 1, 2020

(54) LOCALIZED MODULATION OF TISSUES AND CELLS TO ENHANCE THERAPEUTIC EFFECTS INCLUDING RENAL DENERVATION

(71) Applicant: Mercator MedSystems, Inc., San Leandro, CA (US)

(72) Inventor: Kirk P. Seward, San Francisco, CA (US)

(73) Assignee: MERCATOR MEDSYSTEMS, INC., Emeryville, CA (US)

( * ) Notice: Subject to any disclaimer, the term of this patent is extended or adjusted under 35 U.S.C. 154(b) by 100 days.

(21) Appl. No.: 13/656,413

(22) Filed: Oct. 19, 2012

(65) Prior Publication Data

US 2013/0252932 A1    Sep. 26, 2013

Related U.S. Application Data

(60) Provisional application No. 61/548,822, filed on Oct. 19, 2011.

(51) Int. Cl.
*A61K 31/395* (2006.01)
*C07D 295/13* (2006.01)

(52) U.S. Cl.
CPC .......... *A61K 31/395* (2013.01); *C07D 295/13* (2013.01)

(58) Field of Classification Search
CPC ....... A61K 8/43; A61K 31/395; C07D 295/13
USPC ....................................................... 514/183
See application file for complete search history.

(56) References Cited

U.S. PATENT DOCUMENTS

| | | |
|---|---|---|
| 3,271,448 A | 9/1966 | Augstein et al. |
| 3,301,755 A | 1/1967 | Mull et al. |
| 3,723,463 A | 3/1973 | Yale et al. |
| 3,780,733 A | 12/1973 | Martinez-Manzor |
| 3,911,125 A | 10/1975 | Bacaner |
| 4,105,030 A | 8/1978 | Kercso |
| 4,483,861 A | 11/1984 | Iwao et al. |
| 4,496,573 A | 1/1985 | Studt et al. |
| 4,496,578 A | 1/1985 | Iwao et al. |
| 5,112,305 A | 5/1992 | Barath et al. |
| 5,147,294 A | 9/1992 | Smith et al. |
| 5,196,024 A | 3/1993 | Barath |
| 5,242,397 A | 9/1993 | Barath et al. |
| 5,354,279 A | 10/1994 | Hofling |
| 5,364,374 A | 11/1994 | Morrison et al. |
| 5,423,851 A | 6/1995 | Samuels |
| 5,538,504 A | 7/1996 | Linden et al. |
| 5,591,139 A | 1/1997 | Lin et al. |
| 5,609,629 A | 3/1997 | Fearnot et al. |
| 5,645,564 A | 7/1997 | Northrup et al. |
| 5,658,515 A | 8/1997 | Lee et al. |
| 5,665,071 A | 9/1997 | Wyrick |
| 5,681,281 A | 10/1997 | Vigil et al. |
| 5,693,029 A | 12/1997 | Leonhardt |
| 5,722,989 A | 3/1998 | Fitch et al. |
| 5,851,197 A | 12/1998 | Marano et al. |
| 5,879,326 A | 3/1999 | Godshall et al. |
| 6,009,875 A | 1/2000 | Hubbard, Jr. |
| 6,009,877 A | 1/2000 | Edwards |
| 6,059,815 A | 5/2000 | Lee et al. |
| 6,093,172 A | 7/2000 | Funderburk et al. |
| 6,102,933 A | 8/2000 | Lee et al. |
| 6,187,210 B1 | 2/2001 | Lebouitz et al. |
| 6,210,392 B1 | 4/2001 | Vigil et al. |
| 6,256,533 B1 | 7/2001 | Yuzhakov et al. |
| 6,283,947 B1 | 9/2001 | Mirzaee |
| 6,293,925 B1 | 9/2001 | Safabash et al. |
| 6,302,870 B1 | 10/2001 | Jacobsen et al. |
| 6,331,266 B1 | 12/2001 | Powell et al. |
| 6,334,856 B1 | 1/2002 | Allen et al. |
| 6,451,240 B1 | 9/2002 | Sherman et al. |
| 6,524,274 B1 * | 2/2003 | Rosenthal et al. ......... 604/96.01 |
| 6,547,803 B2 | 4/2003 | Seward et al. |
| 6,743,211 B1 | 6/2004 | Prausnitz et al. |
| 6,787,569 B1 | 9/2004 | Goldin et al. |
| 6,860,867 B2 | 3/2005 | Seward et al. |
| 6,978,174 B2 | 12/2005 | Gelfand et al. |

(Continued)

FOREIGN PATENT DOCUMENTS

| | | |
|---|---|---|
| JP | 05-293176 A | 11/1993 |
| JP | 11-262527 A | 9/1999 |

(Continued)

OTHER PUBLICATIONS

Akinobu et al., "Effects of Renal Sympathectomy on Sodium and Water Excretion in Stroke-Prone Spontaneously Hypertensive Rats," Japan J. Pharmacol. 32, 591-597 (1982).
Altman et al., Exploring heart lymphatics in local drug delivery, Lymph. Res. Biol., (2003) 1:47-54.
Baltazar et al., "Differential contribution of syntaxin 1 and SNAP-25 to secretion in noradrenergic and adrenergic chromaffin cells," Eur J Cell Biol 2000;79(12):883-891.
Bastid et al., "Percutaneous Alcoholization of the celiac plexus under echographic guidance : an alternative to splanchnicectomy? Study of 21 cases," Annales de gastroenterologie et d'hepatologie, vol. 27 (4), pp. 163-166 (1991) (with English Abstract).

(Continued)

*Primary Examiner* — Doan T Phan
(74) *Attorney, Agent, or Firm* — Wilson Sonsini Goodrich & Rosati

(57) ABSTRACT

Pharmaceutical preparations, compositions, systems, and devices including medical devices and diagnostic or therapeutic agents, and methods to treat disease by modification of local tissue environment to modulate the therapeutic index of locally or systemically delivered therapeutic or diagnostic agents. Improved ability to reduce sympathetic nerve activity in the adventitia and perivascular tissues around arteries and veins in the body. Modulation of the local tissue environment around an artery to enable more effective denervation with or without a therapeutic agent. Modulation may include adjustment of the pH of the tissue.

23 Claims, 20 Drawing Sheets

(56) References Cited

U.S. PATENT DOCUMENTS

| | | | |
|---|---|---|---|
| 7,022,214 B2 | 4/2006 | Olech | |
| 7,074,834 B2 | 7/2006 | Tobin | |
| 7,141,041 B2 | 11/2006 | Seward | |
| 7,162,303 B2 | 1/2007 | Levin et al. | |
| 7,547,294 B2 | 6/2009 | Seward et al. | |
| 7,647,115 B2 | 1/2010 | Levin et al. | |
| 7,666,163 B2 | 2/2010 | Seward et al. | |
| 7,691,080 B2 | 4/2010 | Seward et al. | |
| 7,744,584 B2 | 6/2010 | Seward et al. | |
| 7,756,583 B2 | 7/2010 | Demarais et al. | |
| 8,131,372 B2 | 3/2012 | Levin et al. | |
| 8,145,317 B2 | 3/2012 | Demarais et al. | |
| 8,150,519 B2 | 4/2012 | Demarais et al. | |
| 8,150,520 B2 | 4/2012 | Demarais et al. | |
| 8,184,711 B2 | 5/2012 | Horiuchi et al. | |
| 9,011,879 B2 | 4/2015 | Seward | |
| 2002/0050456 A1 | 5/2002 | Sheppard, Jr. et al. | |
| 2002/0082543 A1 | 6/2002 | Park et al. | |
| 2002/0188310 A1 | 12/2002 | Seward et al. | |
| 2003/0040712 A1 | 2/2003 | Ray et al. | |
| 2003/0078562 A1 | 4/2003 | Makower et al. | |
| 2003/0120297 A1 | 6/2003 | Beyerlein | |
| 2003/0171734 A1 | 9/2003 | Seward et al. | |
| 2004/0067197 A1 | 4/2004 | Leclerc et al. | |
| 2004/0138643 A1 | 7/2004 | Seward et al. | |
| 2005/0021092 A1 | 1/2005 | Yun et al. | |
| 2005/0090714 A1 | 4/2005 | Greff | |
| 2005/0267010 A1* | 12/2005 | Goodson et al. | 514/2 |
| 2006/0025821 A1 | 2/2006 | Gelfand et al. | |
| 2006/0189941 A1 | 8/2006 | Seward et al. | |
| 2006/0212076 A1 | 9/2006 | Demarais et al. | |
| 2006/0212078 A1 | 9/2006 | Demarais et al. | |
| 2006/0265014 A1 | 11/2006 | Demarais et al. | |
| 2006/0276852 A1 | 12/2006 | Demarais et al. | |
| 2007/0100318 A1* | 5/2007 | Seward et al. | 604/506 |
| 2007/0173899 A1 | 7/2007 | Levin et al. | |
| 2007/0203549 A1 | 8/2007 | Demarais et al. | |
| 2007/0269385 A1 | 11/2007 | Yun et al. | |
| 2007/0281026 A1* | 12/2007 | Vyavahare et al. | 424/484 |
| 2008/0004596 A1 | 1/2008 | Yun et al. | |
| 2008/0193565 A1* | 8/2008 | Hornack et al. | 424/709 |
| 2009/0076409 A1 | 3/2009 | Wu et al. | |
| 2009/0192214 A1* | 7/2009 | Gravett et al. | 514/449 |
| 2009/0232850 A1 | 9/2009 | Manack et al. | |
| 2009/0263483 A1* | 10/2009 | Desai et al. | 424/484 |
| 2011/0091549 A1* | 4/2011 | Blaskovich et al. | 424/484 |
| 2011/0104060 A1 | 5/2011 | Seward | |
| 2011/0104061 A1 | 5/2011 | Seward | |
| 2013/0287698 A1 | 10/2013 | Seward | |

FOREIGN PATENT DOCUMENTS

| | | |
|---|---|---|
| JP | 2003-000708 A | 1/2003 |
| WO | WO 99/33504 A1 | 7/1999 |
| WO | WO 2001/43775 A2 | 6/2001 |
| WO | WO 02/100459 A2 | 12/2002 |
| WO | WO 2012/161875 A1 | 11/2012 |

OTHER PUBLICATIONS

BDTM PuraMatrixTM Peptide Hydrogel (Catalog No. 354250), Guidelines for Use, BD Biosciences, SPC-354250-G Rev 4.0., 2006; retrieved from the Internet: <http://www.bdbiosciences.com/external_files/d1/doc/manuals/live/web_enabled/354250Lpug.pdf>, 17 pages total.

Bello-Reuss et al., "Effects of Acute Unilateral Renal Denervation in the Rat," Journ. of Clin. Invest., vol. 56, pp. 207-217 (1975).

Bichet et al., "Renal intracortical blood flow and rennin secretion after denervation by 6-hydroxydopamine," Canadian Journ. Phys. and Pharma., vol. 60 (2), pp. 184-192 (1982).

Bidwai et al., "Preoperative Stellate-ganglion Blockade to Prevent Hypertension Following Coronary-artery Operations," Anesthesiology, vol. 51, No. 4, pp. 345-347 (1979).

Bilici, et al. Treatment of hypertension from renal artery entrapment by percutaneous-CT-guided botulinum toxin injection into diaphragmatic crus as alternative to surgery and stenting. AJR Am J Roentgenol. Sep. 2007;189(3):W143-5.

Bokhari et al., "The enhancement of osteoblast growth and differentiation in vitro on a peptide hydrogel-polyHIPE polymer hybrid material," Biomaterials Sep. 2005;26(25):5198-5208; retrieved from the Internet: <http://web.mitedu/Ims/www/PDFpapers/Bolchari%20et%20a1,%202005.pdf.

Braun-Dullaeus-et al.. "Cell cycle progression: new therapeutic target for vascular proliferative disease," Circulation. 1998; 98(1):82-9; retrieved from the Internet: <http://circ.ahajournals.org/cgi/reprint/98/1/82.

Calhoun et al, "Resistant Hypertension: Diagnosis, Evaluation and Treatment: A scientific statement from the American Heart Association Professional Education Committee of the Council for High Blood Pressure Research," Hypertension 2008;51:1403-1419; retrieved from the Internet: <http://hyper.ahajournals.org/cgi/reprint/HYPERTENSIONAHA.108.189141v1.

Campese et al., "Renal Afferent Denervation Prevents Hypertension in Rats with Chronic Renal Failure," Hypertension 1995;25:878-882; retrieved from the Internet: <http ://hyper.ahajournals.org/cgi/content/full/25/4/878.

Carroll et al., "Sympathetic block with botulinum toxin to treat complex regional pain syndrome," Annals of Neurology 2009;65(3):348-351.

Cepoi et al., "The Prevalence of chronic kidney disease in the general population in Romania: a study of 60,000 persons," *Int Urol Nephrol* (2012) 44:213-220.

Chan et al., "Update on Pharmacology for Restenosis," Current Interventional Cardiology Reports, 2001, 3: 149-155.

Cheng et al., "Unlabeled Uses of Botulinum Toxins: A Review, Part 1," Am J Health-Syst Pharm 2005;63(2):145-152.

Ciccone et al., "Effects of acute renal denervation on kidney function in deoxycorticosterone acetate-hypertensive swine," Hypertension 1986;8:925-931; retrieved from the Internet: <http://hyper.ahajournals.org/cgi/reprint/8/10/925.

Clemens et al., "Prevention of anastomotic thrombosis by Botulinum Toxin A in an animal model," Plast Rectonstr Surg 2009;123(1) 64-70.

CN201080028114.7 Office Action dated Jun. 14, 2013.

CN201080028114.7 Office Action dated Nov. 25, 2013.

Connors et al, "Renal nerves mediate changes in contralateral renal blood flow after extracorporeal shockwave lithotripsy," Nephron Physiology 2003;95:67-75.

Coresh et al., "Prevalence of Chronic Kidney Disease in the United States," *JAMA*. 2007;298(17):2038-2047 (doi: 10.1001/jama.298.17.2038.

Cruickshank, Current Cardiology Reports 2003;5:441-452 (9671):1228-1230.

Cutts et al., "Ureteric Injury as a Complication of Chemical Sympathectomy," Eur J. Vase Endovasc Surg 19, 212-213 (2000).

Das et al., "Sonographically Guided Coeliac Plexus-Block," Clinical Radiology, 45, pp. 401-403 (1992).

Daschner et al., "Penetration of gentamicin into heart valves, subcutaneous and muscular tissue of patients undergoing open heart surgery", J. Cardiovasc. Surg., (1986) 581-584.

Davis et al., "Injectable self-assembling peptide nanofibers create intramyocardial microenvironments for endothelial cells," Circulation 111: 442-450, 2005; retrieved from the Internet: <http://circ.ahajournals.org/cgi/reprint/111/4/442>.

De Paiva et al, "Functional repair of motor endplates after botulinum neurotoxin type A poisoning: Biphasic switch of synaptic activity between nerve sprouts and their parent terminals," Proc Proc Natl Acad Sci 1999;96:3200-3205; retrieved from the Internet: <http://www.pnas.org/content/96/6/3200.full.pdf+html.

De Smet et al., "Metalloproteinase Inhibition Reduces Constrictive Arterial Remodeling After Balloon Angioplasty: A Study in the Atherosclerotic Yucatan Micropig." Circulation, 2000, 101: 2962-2967; retrieved from the Internet: <ftp://circ.ahajour nals.org/cgi/reprint/101/25/2962.

Dekrey et al., "Selective Chemical Sympathectomy," Anesthesia and Analgesia, vol. 47, No. 5, (1968).

(56) References Cited

OTHER PUBLICATIONS

Demas et al., "Novel Method for localized, functional sympathetic nervous-system denervation of peripheral tissue using guanethidine," Journal of Neuroscience Methods. 2001;112:21-28.
Dibona et al., "Translational Medicine: The Antihypertensive Effect of Renal Denervation," American Journal of Physiology—Regulatory, Integrative and Comparative Physiology. Feb. 2010;298(2):R245-253.
Dibona, "Nervous-Kidney: Interaction between renal sympathetic nerves and the renin-angiotensin system in the control of renal function," Hypertension 2000;36:1083-1088; retrieved from the Internet: <http://hyper.ahajournals.org/cgi/reprint/36/6/1083.
Dibona, "The Sympathetic Nervous-System and Hypertension: Recent Developments," Hypertension 2004;43;147-150; retrieved from the Internet: <http://hyper.ahajournals.org/cgi/reprint/43/2/147.
DiBona, G., "Neural Control of the Kidney: Functionally Specific Renal Sympathetic Nerve Fibers," Am J Physiol Regulatory Integrative Comp Physiol, 2000, 279: R1517-R1524, The American Physiological Society, Bethesda, MD.
DiBona, G.F., "Functionally Specific Renal Sympathetic Nerve Fibers: Role in Cardiovascular Regulation," American Journal of Hypertension, Jun. 2001, 14:163S-170S.
DiBona, G.F., "Sympathetic Nervous-System and the Kidney in Hypertension," Current Opinion in Nephrology and Hypertension, 2002, 11:197-200, Lippincott Williams & Wilkins Press.
Dibona, Gerald F. and Linda L. Sawin, "Role of renal nerves in sodium retention of cirrhosis and congestive heart failure," Sep. 27, 1990, Am J Physiol 1991, vol. 260, © 1991 the American Physiological Society, pp. R296-R305.
Dibona, Gerald F. and Ulla C. Kopp, "Neural Control of Renal Function," Physiological Reviews Jan. 1997, vol. 77, No. 1, © 1997 American Physiological Society, pp. 75-197.
Dibona, Gerald F., "Neural Control of the Kidney-Past, Present, and Future," Nov. 4, 2002, Novartis Lecture, Hypertension 2003, vol. 41, part 2, 2002 American Heart Association, pp. 621-624.
Dibona, Gerald F., "Peripheral and Central Interactions between the Renin-Angiotensin System and the Renal Sympathetic Nerves in Control of Renal Function," Annals New York Academy of Sciences, 940:395-406 (2001).
Dibona, Gerald F., "Renal Innervation and Denervation. Lessons from Renal Transplantation Reconsidered," Artificial Organs, vol. 11, No. 6, Raven Press Ltd., © 1987 International Society for Artificial Organs, pp. 457-462.
Dibona, Gerald F., L.L. Sawin, "Effect of renal denervation on dynamic autoregulation of renal blood flow," Feb. 12, 2004, Am J Physiol Renal Physiol 286, pp. F1209-F1218.
Dibona, Gerald F., L.L. Sawin, Effect of renal nerve stimulation on NaCI and H2O transport in Henle's loop of the rat,: (1982), American Physiological Society, F576-F580, 5 pages.
Dibona, Gerald F., Susan Y. Jones, "Dynamic Analysis of Renal Nerve Activity Responses to Baroreceptor Denervation in Hypertensive Rats," Sep. 19, 2000, Hypertension Apr. 2001, © 2001 American Heart Association, pp. 1153-1163.
Diz et al., "Renal Denervation at Weaning Retards Development of Hypertension in New Zealand Genetically Hypertensive Rats," Hypertension, 4: 361-368 (1982).
Doumas, M., et al., "Interventional management of resistant hypertension," Lancet, 2009, 373:1228-1229.
EP 10767782 Search Report dated Sep. 7, 2012.
Erickson et al., "Differential maturation and structure-function relationships in mesenchymal stem cell- and chondrocyte-seeded hydrogels," Tissue Engineering Part A, May 2009, 15(5): 1041-1052.
Farsak et al., "Detection of Chlamydia pneumoniae and Helicobacter pylon DNA in human atherosclerotic plaques by PCR," J Clin Microbiol 2000; 38(12):4408-4411; retrieved from the Internet: <http://jcm.asm.org/cgi/reprint/38/12/4408.
Fassio et al., "Evidence for calcium-dependent vesicular transmitter release insensitive to tetanus-toxin and botulinum toxin type F," Neuroscience 1999;90(3):893-902.
Foran et al., "Botulinum neurotoxin C1 cleaves both syntaxin and SNAP-25 in intact and permeabilized chromaffin cells: correlation with its blockade of catecholamine release," Biochemistry 1996;35(8):2630-6.
Friedman, et al. Differential development of salt-induced and renal hypertension in Dahl hypertension-sensitive rats after neonatal sympathectomy. Clin Exp Hypertens. 1979;1(6):779-99.
Fuchs et al., "Anti-angiogenesis: A new potential strategy to inhibit restenosis," Intl J Cardiovasc Intervent. 2001; 4:3-6.
Gallo et al., "Inhibition of intimal thickening after balloon angioplasty in porcine coronary arteries by targeting regulators of the cell cycle," Circulation. 1999; 99:2164-2170; retrieved from the Internet: <http://circ.ahajournals.org/cgi/reprint/99/16/2164.
Grady et al., "Renal blood flow varies during normal activity in conscious unrestrained rats," Am J Physiol Regul Integr Comp Physiol May 1, 1992, 262:(5) R926-R932.
Grayston, "Antibiotic Treatment of Chlamydia pneumoniae for secondary prevention of cardiovascular events," Circulation. 1998; 97(17):1669-1670.
Grisk, "Sympatho-renal interactions in the determination of arterial pressure: role in hypertension," Experimental Physiology 2004;90(2):183-187; retrieved from the Internet: <http://ep.physoc.org/content/90/2/183.full.pdf+html.
Hansen et al., "Prevalence of renovascular disease in the elderly: A population-based study," Journal of Vascular Surgery, Sep. 2002, vol. 36, No. 3, pp. 443-451.
Hayakawa et al., "Effect of Celiac Plexus Block and Thoracic Epidural Block on Arterial Ketone Body Ratio," Masui, 43(11):1653-8 (1994) (with English Abstract).
Hayakawa et al., "Paraplegia After Intraoperative Celiac Plexus Block," Anesth. Analg., 84:447-448 (1997).
Hayashi et al., "Effect of surugatoxin on celiac ganglia in cats," Folia Pharmacol. Japan, 73, pp. 657-663 (1977) (with English Abstract).
Healey et al., "The management of patients with carotid sinus syndrome: is pacing the answer," Clin Auton Res Oct. 2004;14 Suppl 1:80-6.
Hegedus, "Stenosis of the Celiac Artery," Radiologe 13, pp. 443-447 (1973).
Hengstmann et al., "Disposition of Guanethidone During Chronic Oral Therapy," Europ. Journ. Clin. Pharmacol., vol. 15, pp. 121-125 (1979).
Henriksson et al., "Transplantation of human mesenchymal stems cells into intervertebral discs in a xenogeneic porcine model," Spine Jan. 15, 2009;34(2):141-8.
Herdeg et al., "Local paclitaxel delivery for the prevention of restenosis: biological effects and efficacy in vivo," J Am Coll Cardiol Jun. 2000; 35(7):1969-1976; retrieved from the Internet: <http://content.onlinejacc.org/cgi/reprint/35/7/1969.pdf.
Hill C.E., et al., "Use of tissue culture to examine the actions of guanethidine and 6-hydroxydopamine," European Journal of Pharmacology, 1973; 23:1620-74.
Huang et al., "Renal denervation prevents and reverses hyperinsulinernia-induced hypertension in rats," Hypertension 1998;32:249-254; retrieved from the Internet: <http://hyper.ahajournals.org/cgi/reprint/32/2/249.
Humeau et al., "How botulinum and tetanus neurotoxins block neurotransmitter release," Biochimie 2000;82(5):427-446.
International Search Report and Written Opinion of PCT Application No. PCT/US10/32097, dated Jun. 18, 2010, 8 pages total.
Ischia et al., "Three Posterior Percutaneous Celiac Plexus Block Techniques," Anesthesiology, 76:534-540 (1992).
Ismail et al, "The role of infection in atherosclerosis and coronary artery disease: a new therapeutic target," Heart Dis. 1999; 1(4):233-240.
Janssen et al., "Effects of complete renal denervation and selective afferent renal denervation on the hypertension induced by intrarenal norepinephrine infusion in conscious rats," Journ. Hypertension 7:447-455 (1989).
Johnson EM and Aloe L. "Suppression of the in vitro and in vivo cytotoxic effects of guanethidine in sympathetic neurons by nerve growth factor," Brain Research, 1974; 81:519-532.

(56) References Cited

OTHER PUBLICATIONS

Johnson et al., "Guanethidine-Induced Destruction of Sympathetic Neurons, International Review of Neurobiology," vol. 25, p. 8-9 (Academic Press)(1984).
Joles et al., "Causes and Consequences of Increased Sympathetic Activity in Renal Disease," Hypertension 2004;43:699-706; retrieved from the Internet: <http://hyper.ahajournals.org/cgi/reprint/43/4/699>.
Katholi et al., "Role of the renal nerves in the pathogenesis of one-kidney renal hypertension in the rat," Hypertension 1981;3:404-409; retrieved from the Internet: <http://hyper.ahajournals.org/cgi/reprint/3/4/404.
Katholi et al., "Importance of the Renal Nerve in Established Two-Kidney, One Clip Goldblatt Hypertension," Hypertension, 4, pp. 166-174 (1982).
Kim et al., "A microfluidic platform for 3-dimensional cell culture and cell-based assays," Biomed Microdevices Feb. 2007;9(1):25-34.
Kim et al., "Idiopathic foot dystonia treated with intramuscular phenol injection," Parkinsonism and Related Disorders , 9 (2003) pp. 355-359.
Kol et al., "Chlamydial and human heat shock protein 60s activate human vascular endothelium, smooth muscle cells, and macrophages," J Clin Invest, 1999; 103(4):571-577; retrieved from the Internet: <http://www.jci.org/articles/view/5310.
Kompanowska-Jezierska et al., "Early effects of renal denervation in the anaesthetised rat: natriuresis and increased cortical blood flow," Journ. of Physiol., 531(2), pp. 527-534 (2001).
Koutsopoulos et al., "Controlled release of functional proteins through designer self-assembling peptide nanofiber hydrogel scaffold," Proc Natl Acad Sci 2009;106(12):4623-4628; retrieved from the Internet: <http://www.pnas.org/content/early/2009/03/06/0807506106.full.pdf+html.
Krum et al, "Catheter-based renal sympathetic denervation for resistant hypertension: a multicentre safety and proof-of-principle cohort study," Lancet 2009;373(9671):1228-1230.
Krum et al., "Device-Based Antihypertensive Therapy: Therapeutic Modulation of the Autonomic Nervous System," Circulation 2011; 123;209-215, DOI: 10.1161/CIRCULATIONAHA.110.971580, Downloaded from circ.ahajournals.org at Cons California Dig Lib on May 17, 2011.
Laham et al., Intracoronary and intravenous administration of basic fibroblast growth factor: myocardial and tissue distribution, Drug Met. Disp., (1999) 27:821-826.
Laham et al., Intrapericardial administration of basic fibroblast growth factor: myocardial and tissue distribution and comparison with intracoronary and intravenous administration, Cath Cardio. Interv., (2003) 58:375-381.
Lowe et al., "Coronary in-stent restenosis: Current status and future strategies," J Am Coll Cardiol. Jan. 16, 2002; 39(2):183-93; retrieved from the Internet: <http://content.onlinejacc.org/cgi/reprintframed/39/2/183.
Luippold et al., "Chronic renal denervation prevents glomerular hyperfiltration in diabetic rats," Nephrol Dial Transplant, 19, pp. 342-347 (2004).
Lundemose et al., "Chlamydia trachomatis Mip-like protein has peptidyl-prolyl cis/trans isomerase activity that is inhibited by FK506 and rapamycin and is implicated in initiation of chlamydial infection," Mol Microbiol. 1993; 7(5):777-83.
Manjunath et al., "Management of Lower Limb Complex Regional Pain Syndrome Type 1: An Evaluation of Percutaneous Radiofrequency Thermal Lumber Sympathectomy Versus Phenol Lumbar Sympathetic Neurolysis—A Pilot Study," Anesthesia & Analgesia, vol. 106, No. 2, pp. 647-649, (2008).
Masuoka et al., "Distribution of Internal Elastic Lamina and External Elastic Lamina in the Internal Carotid Artery: Possible Relationship with Atherosclerosis," Neurol. Med. Chir. (Tokyo) , 2010, 50:179-182.
Mercadante et al., "Celiac Plexus Block: A Reappraisal," Regional Anesthesia and Pain Medicine 23(1):37-48 (1998).
Misawa et al., "PuraMatrix facilitates bone regeneration in bone defects of calvaria in mice," Cell Transplant 2006;15(10):903-910.
Mizelle et al, "Role of renal nerves in compensatory adaptation to chronic reductions in sodium uptake," Am J Physiol Renal Physiol, 1987; 252(2): F291-F298.
Moore et al., "An Improved Technique for Celiac Plexus Block May Be More Theoretical Than Real," Anesthesiology, vol. 57, No. 4, pp. 347-348 (1982).
Moore et al., "Celiac Plexus Block: A Roentgenographic, Anatomic Study of Technique and Spread of Solution in Patients and Corpses," Anesth. Analg., vol. 60, No. 6, pp. 369-379 (1981).
Morris et al., "Botulinum neurotoxin A attenuates release of norepinephrine but not NPY from vasoconstrictor neurons," Am J Physiol Heart Circ Physiol 2002;283(6):H2627-H2635; retrieved from the Internet: <http://ajpheart.physiology.org/cgi/reprint/283/6/H2627.
Muhlestein et al., "Infection with Chlamydia pneumoniae accelerates the development of atherosclerosis and treatment with azithromycin prevents it in a rabbit model," Circulation. 1998; 97:633-636; retrieved from the Internet: <http://circ.ahajournals.org/cgi/reprint/97/7/633.
Myhre et al., "Monitoring of Celica Plexus Block in Chronic Pancreatitis," Pain, 38, pp. 269-274 (1989).
Nagai et al., "Slow release of molecules in self-assembling peptide nanofiber scaffold," J Control Rel. 2006;115:18-25.
Norman et al., "Role of renal nerves in onset and maintenance of spontaneous hypertension," Am. J. Physiol., 243(2):H284-8 (1982).
Nozdrachev et al., "The changes in the nervous structures under the chemical sympathectomy with guanethidine," Journal of the Autonomic Nervous System 1998;74(2-3):82-85.
NZ 596041 Exam Report dated Jul. 9, 2013.
NZ 596041 Exam Report dated Nov. 5, 2013.
NZ 596041 Exam Report dated Sep. 3, 2013.
NZ 596041 Exam Report dated Jan. 15, 2014.
Overbeck, "Pressure-independent increases in vascular resistance in hypertension: role of sympathoadrenergic influences," Hypertension, vol. 2, No. 6, pp. 780-786 (1980).
Owitz et al., "Celiac Plexus Block: An Overview," The Mount Sinai Journal of Medicine, vol. 50, No. 6, pp. 486-490 (1983).
Ozkan et al., "Renal artery origins and variations: angiographic evaluation of 855 consecutive patients," Diagn Intery Radiol 12:183-186 (2006).
PCT/US2012/061205 International Search Report dated Feb. 13, 2013.
Pechan et al., "The Effect of Guanethecline and Propranolol on Capillary Blood Flow in Subcutaneous Tissue and Muscle in Essential Hypertension," Cardiology, vol. 59, No. 3, pp. 172-183 (1974).
Peet, "Hypertension and its Surgical Treatment by Bilateral Supradiaphragmatic Splanchnicectomy," Amer. Journ. Surgery, vol. 74, No. 1, pp. 48-68 (1948).
Persell, Stephen D., Prevalence of Resistant Hypertension in the United States, 2003 2008, *Hypertension* published online Apr. 11, 2008; DOI: 10.1161/HYPERTENSIONAHA.111.170308, Downloaded from hyper.ahajournals.org at Cons California Dig Lib on May 15, 2011.
Picklo, "Methods of sympathetic degeneration and alteration," Journal of the Autonomic Nervous System 1997;62:111-125.
Pires et al., "Renal blood flow dynamics and arterial pressure liability in the conscious rat," Hypertension, 38:147-152 (2001).
Rahn, "The influence of renal function on plasma levels, urinary excretion, metabolism, and antihypertensive effect of guanethidine (Ismelin) in man," Clinical Nephrology, vol. 1, No. 1, pp. 14-23 (1973).
Richardson et al., "Mechanisms of Renal Release of Renin by Electrical Stimulation of the Brainstem in the Cat," Circulation Research, 34:425-434 (1974).
Simpson, "Botulinum Toxin: a Deadly Poison Sheds its Negative Image," Annals of Internal Medicine 1996;125(7):616-617.
Skretting, "Hypotension After Intercostal Nerve Block During Thoracotomy Under General Anesthesia," Br. J. Anaesth., 53, pp. 527-529 (1981).

(56) References Cited

OTHER PUBLICATIONS

Smithwick, R.H et al., "Splanchnicectomy for essential hypertension," Journ. Amer. Med. Assn. 1953, 152:1501-1504.
Smithwick, R.H. et al., "Hypertension and associated cardiovascular disease: comparison of male and female mortality rates and their influence on selection of therapy," JAMA, 1956, 160:1023-1033.
Smithwick, R.H., "Surgical treatment of hypertension," Am J Med (1948), 4:744-759.
Smyth et al., "Nicotinamide adenine dinucleotide is released from sympathetic nerve terminals via a botulinum neurotoxin A-mediated mechanism in canine mesenteric artery," Am J Physiol Heart Circ Physiol 2006;290:H1818-H1825; retrieved from the Internet: <http://ajpheart.physiology.org/cgi/reprint/290/5/H1818.
Solomon et al., Sympathetic Blockade in a Canine Model of Gram-Negative Bacterial Peritonitis, Shock, vol. 19, No. 3, pp. 215-222 (2003).
Spencer et al., "Peptide- and collagen-based hydrogel substrates for in vitro culture of chick cochleae," Biomaterials Mar. 2008;29(8):1028-1042; retrieved from the Internet: http://www.ncbi.nlm.nih.gov/pnnc/articles/PMC2424202/pdf/nihms-52789.pdf.
Tay et al., "Computed tomography fluoroscopy-guided chemical lumbar sympathectomy: Simple, safe and effective," Australasian Radiology, 46, pp. 163-166 (2002).
Taylor et al., "The effects of intravenous guanethidine on the systemic and pulmonary circulations in man," American Heart Journal, vol. 63, No. 2, pp. 239-264 (1962).
Thomas et al., "Chemical Sympathectomy Alters the Development of Hypertension in Miniature Swine," Hypertension, 17: 357-362 (1991).
Thonhoff Jr, et al., "Compatibility of human fetal neural stem cells with hydrogel biomaterials in vitro," Brain Res Jan. 2, 2008;1187:42-51; retrieved from the Internet: <http://www.ncbi.nlnn.nih.gov/pmc/articles/PMC2176077/pdf/nihms36277.pdf.
"Adventitial Toorop et al., Stripping for Carotid Sinus Syndrome," Ann Vasc Surg. Jul.-Aug. 2009;23(4):538-47. Epub Jan. 8, 2009.
Toorop et al., "Effective surgical treatment of the carotid sinus syndrome," J Cardiovasc Surg (Torino). Oct. 2009;50(5):683-686. Epub Oct. 24, 2008.
Varenne et al., "Gene Therapy for Coronary Restenosis: A Promising Strategy for the New Millennium?" Current Interventional Cardiology Reports, 2000, 2(4):309-315.
Villanueva et al., "Epinephrine and dopamine colocalization with norepinephrine in various peripheral tissues: guanethidine effects," Life Sci. 2003;73(13)1645-53.
Vincenzi, "Effect of Botulinum Toxin on Autonomic Nerves in a Dually Innervated Tissue," Nature 1967;213:394-395.
Vranken et al., "Neurohistopatholgic findings after a neurolytic celiac plexus block with alcohol in patients with pancreatic cancer pain," Acta Anaesthesiol Strand, 46: 827-830 (2002).
Wahbi, Abdel-Aziz M. et al. "Spectrofluorimetric determination of guanethidine slphate, guanfacine hydrochloride, guanoclor sulphate and guanoxan sulphate in tablets and biological fluids, using benzion," Microchimica Acta 11.1 (1993): 83-91.
Wakshull, E., et al. "Persistance of an amine uptake system in cultured rat sympathetic neurons which use acetylcholine as their transmitter," J. Cell Biology, 1978;79:121-131.
Wang et al., "Three-dimensional primary hepatocyte culture in synthetic self-assembling peptide hydrogel," Tissue Eng Part A Feb. 2008;14(2):227-36.
Winternitz et al., "Role of the Renal Sympathetic Nerves in the Development and Maintenance of Hypertension in the Spontaneously Hypertensive Rat," J. Clin. Invest., vol. 66, pp. 971-978 (1980).
Yamaoka et al., "Cartilage tissue engineering using human auricular chondrocytes embedded in different hydrogel materials," J Biomed Mater Res A Jul. 2006;78(1):1-11; retrieved from the Internet: <http://www.puramatrix.com/publication/YamaokaEtal_BiomedMater.pdf.
Yoshida ,"The use of 3-D culture in peptide hydrogel for analysis of discoidin domain receptor 1-collagen interaction," Cell Adh Migr, Apr. 2007;1(2):92-98; retrieved from the Internet: <http://www.ncbi.nlm.nih.gov/pmc/articles/PMC2633976/pdf/cam0102_0092.pdf.
Zhang et al., "PuraMatrix: Self-assembling Peptide Nanofiber Scaffolds," Chapter 15 in Scaffolding in Tissue Engineering, CRC Press, 2005; retrieved from the Internet: <http://www.3d-matrix.co.jp/dl_file/PuraMatrix_Introduction.pdf.
European search report and opinion dated Jul. 10, 2015 for EP Application No. 12841245.
Canadian Application No. 2,887,597 Office Action dated Apr. 7, 2016.

* cited by examiner

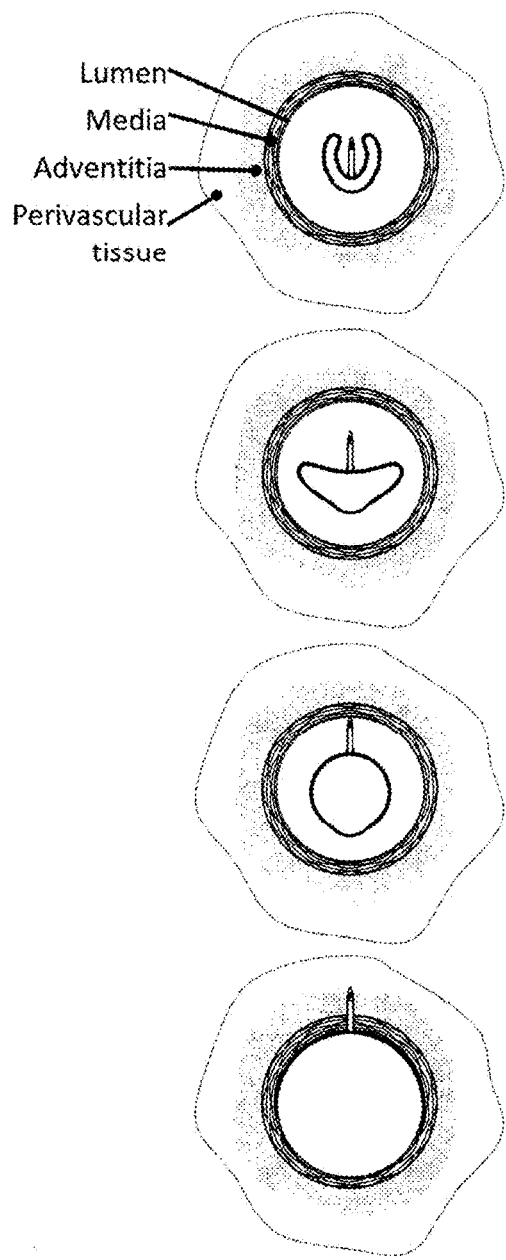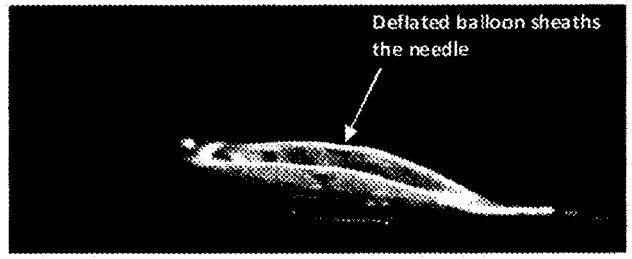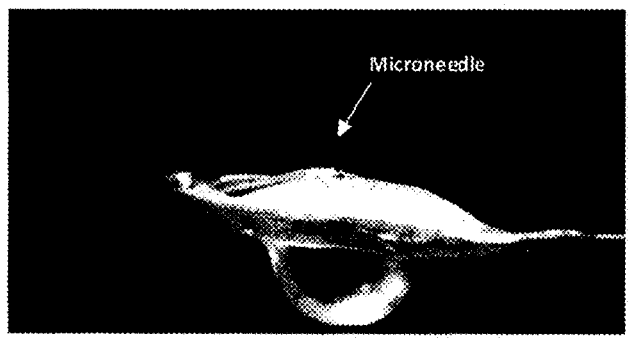

The Bullfrog® Micro-Infusion Catheter: The Bullfrog Catheter is introduced into the artery while deflated and the needle is sheathed within a balloon (top). When the balloon is inflated, the needle is extruded outward, perpendicular to the axis of the catheter. The image above shows the deflated balloon as it is advanced into the artery. The balloon walls sheath the needle and protect the artery wall during introduction or removal of the device. The image below shows the expanded Bullfrog Catheter, with the needle deployed and a backing balloon to provide an opposing force to slide the needle into the bronchial wall. The figures to the left show the cross-sectional balloon profile as it sheaths the needle (top left) and during inflation to push the needle into the artery wall (bottom left).

*FIG. 12*

Guanethidine    Sulfate

Guanethidine    Sulfate

LOCALIZED MODULATION OF TISSUES AND CELLS TO ENHANCE THERAPEUTIC EFFECTS INCLUDING RENAL DENERVATION

CROSS-REFERENCE TO RELATED APPLICATIONS

This application claims the benefit of U.S. Provisional Application No. 61/548,822, filed Oct. 19, 2011, which application is incorporated herein by reference in its entirety.

BACKGROUND AND SUMMARY OF THE INVENTION

Pharmaceutical and biotherapeutic agents interact with cells differently depending on the local physiologic conditions of the tissue in which they are delivered or taken up. For example, pH changes can lead to differences in the uptake of drugs into cells due to membrane permeability or polarization of the pharmaceutical agent, among other reasons.

SUMMARY OF THE INVENTION

While it has been published that pH differences may alter drug effects in cell culture assays, the localized or regionalized modification of pH within the body to enable more rapid drug uptake, more rapid clearance, or improved effect has not been attempted.

Provided herein are compositions, methods, devices, and systems that generate this effect by local administration of the pharmaceutical agent guanethidine monosulfate which is also known as 2-(Octahydro-1-azocinyl)ethyl guanidine sulphate; Heptamethylenimine, 1-(2-guanidinoethyl)-; N-(2-Perhydroazocin-1-ylethyl)guanidine; Azocine, 1-((2-(aminoiminomethyl)amino)ethyl)octahydro-; (2-(Hexahydro-(2H)-azocin-1-yl)ethyl)guanidinium sulphate; Azocine, 1-(2-guanidinoethyl)octahydro-; Guanidine, [2-(hexahydro-1(2H)-azocinyl)-ethyl]-, sulfate (1:1); 2-[2-(azocan-1-yl)ethyl]guanidine; Abapresin; Oktadin; Dopom; N-(2-Guanidino ethyl)heptamethylenimine sulfate; Eutensol; Esimil; Dopam; 2-(1-N,N-Heptamethyleneimino)ethylguanidine; Guanidine, (2-(hexahydro-1(2H)-azocinyl)ethyl)-, sulfate (1:1); Guanethidinum [INN-Latin]; Oktatenzin; Oktatensin; Ismelin™; Guanidine, (2-(hexahydro-1(2H)-azocinyl) ethyl)-; Guanetidina [INN-Spanish]; Octatensine; (2-(Hexahydro-1(2H)-azocinyl)ethyl) guanidine hydrogen sulfate; Sanotensin; 2-[2-(azocan-1-yl)ethyl]guanidine; sulfuric acid; 2-(1-Azacyclooctyl)ethylguanidine; Ismelin sulfate; Guanethidine sulfate; (2-(Octahydro-1-azocinyl)ethyl) guanidine; Ismelin; or (2-(Hexahydro-1(2H)-azocinyl)ethyl) guanidine sulfate (1:1), with the chemical formula $C_{10}H_{22}N_4 \cdot H_2O_4S$ and molecular structure displayed in FIG. 16. Provided herein are also compositions, methods, devices, and systems that generate this effect by local administration of the pharmaceutical agent guanethidine hemisulfate.

The present invention relates generally to pharmaceutical preparations, systems including medical devices and diagnostic or therapeutic agents, and methods to treat disease. More particularly, an embodiment of the present invention relates to modification of local tissue environment to modulate the therapeutic index of locally or systemically delivered therapeutic or diagnostic agents. Even more particularly, an embodiment of the present invention relates to improved ability to reduce sympathetic nerve activity in the adventitia and perivascular tissues around arteries and veins in the body.

A particular aspect of the present invention is the ability to modulate the local tissue environment around a renal artery to enable more effective denervation with pharmaceutical agents in order to treat hypertension, heart failure, sleep apnea, insulin resistance, or inflammation.

Provided herein are methods, systems and compositions for the practice of inventions described in U.S. patent application Ser. Nos. 12/765,708 and 12/765,720, the full disclosures of which are incorporated by reference.

A method for improving pharmaceutical therapy is presented herein. In general, embodiments of the methods include improvements in drug therapeutic index with the modulation of physiologic tissue conditions. In particular, embodiments of the methods comprise modulation of pH in local tissues with local drug or buffer delivery in order to enhance the therapeutic index of agents delivered into tissues or in order to have direct therapeutic effect by virtue of modulating tissue pH locally.

Provided herein are methods including specific improvements to guanethidine neurodegeneration in conditions of elevated pH and the methods with which to create such conditions. These methods are particularly useful in the degeneration of the renal nerves located in the adventitia and perivascular tissue surrounding the renal arteries. These nerves are seminal to the initiation and maintenance of the hypertensive state and the denervation of the renal arteries has shown beneficial effect with respect to reductions in blood pressure, improvements in heart failure, reductions in insulin resistance and sleep apnea, and even speculated improvements in vascular inflammatory diseases.

Guanethidine in vitro studies have described cell culture conditions by which guanethidine monosulfate has been cytotoxic to harvested and cultured rat superior cervical ganglia neurons. (Johnson E M and Aloe L. *Suppression of the in vitro and in vivo cytotoxic effects of guanethidine in sympathetic neurons by nerve growth factor*, Brain Research 1974; 81:519-532; Wakshull E, Johnson M I, Burton H. *Persistence of an amine uptake system in cultured rat sympathetic neurons which use acetylcholine as their transmitter*, J. Cell Biology 1978; 79:121-131). The experiments by Johnson, Wakshull and others found that guanethidine has weak cytotoxic activity at pH of 7.0 to 7.2 and strong cytotoxic activity at pH of 8.0 when exposed to 100 μM concentrations of guanethidine for 40 to 48 hours.

In-vivo testing of guanethidine's neuronal cytotoxicity has shown that perivascular injection of guanethidine hemisulfate in concentrations of 8.3 mg/mL and pH of 8.5 to 9.5 produces a renal denervation in pigs, while perivascular injection of 8.3 mg/mL guanethidine monosulfate at pH of 5.5 to 6.5 does not produce the same denervation.

With injection into the perivascular and adventitial space, injectable agents are tracked by the methods described in U.S. Pat. No. 7,744,584, incorporated herein by reference, and agents are preferably injected by catheters similar to those described in U.S. Pat. No. 7,691,080, incorporated herein by reference. It is recognized, however, that other catheters or needles could be used to inject agents locally within tissues to accomplish similar effects to those described herein.

Provided herein are compositions, devices, systems, and methods that locally modulate of physiologic pH by injection or other means (it is known, for example, that in the presence of electrical signals or certain metallic substances, for example, local pH can be modulated). In some embodiments, the method comprises injecting a composition that exists at pH around 9 into the tissues surrounding nerves that are the target of denervation, during, before, or after the delivery of the therapeutic agent guanethidine monosulfate. The injection or infusion of this composition into the tissue surrounding renal arteries (see FIG. 11 below) displaces interstitial fluids that have neutral physiologic pH of around 7.3 to 7.4.

Other methods of the current invention involve the modulation of local tonicity or osmolarity to achieve enhanced cellular uptake of pharmaceutical agents in formulation with or delivered before or after the agents that modulate local tonicity or osmolarity. For example, delivery of a hypertonic saline causes, through osmosis, the release of liquid by cells. Similarly, delivery of hypotonic solutions can cause cells to swell while they take up additional liquid from their surroundings. Agents instilled into the interestium around cells can potentially have improved uptake depending on the local tissue tonicity. This behavior varies from one therapeutic agent to the next, due to ability for agents to bind membrane receptor proteins or enter cells through channels or pores.

Additional methods of the current invention do not involve application of therapeutic agents in concert with local modification of tissue physiology, but rely directly on the local modulation to accomplish therapeutic goals. For example, hypertonic saline, detergents, solvents such as ethanol, strong acids and strong bases can each lead to cell damage, alteration or destruction with the local modulation of physiology. The delivery of these agents by the methods described in this invention are also useful for accomplishing goals set out here such as localized nerve destruction. Modulation of pH in solutions can be accomplished with alkaline or acidic buffer agents. Buffer agents include but are not limited to sodium hydroxide, sodium bicarbonate, magnesium hydroxide, sulfuric acid, hydrochloric acid, citric acid, acetic acid, sodium citrate, sodium acetate, boric acid, potassium dihydrogen phosphate, diethyl barbituric acid, 3-{[tris(hydroxymethyl)methyl]amino}propanesulfonic acid, N,N-bis(2-hydroxyethyl)glycine, tris(hydroxymethyl)aminomethane, N-tris(hydroxymethyl)methylglycine, 2-[Bis(2-hydroxyethyl)amino]-2-(hydroxymethyl)-1,3-propanediol, 3-[N-Tris(hydroxymethyl)methylamino]-2-hydroxypropanesulfonic acid, 4-2-hydroxyethyl-1-piperazineethanesulfonic acid, 2-{[tris(hydroxymethyl)methyl]amino}ethanesulfonic acid, 3-(N-morpholino) propanesulfonic acid, piperazine-N,N'-bis(2-ethanesulfonic acid), dimethylarsinic acid, saline sodium citrate, 2-(N-morpholino)ethanesulfonic acid, or glycine.

In yet another aspect to this invention, a novel composition is described. In improving the performance of guanethidine in local tissue delivery, a pH adjustment may be required. Compositions of the present invention include the formulation of guanethidine in concentrations ranging from 1 μg/mL to 50 mg/mL at pH of greater than 7. In particular aspects of this invention, concentration of a formulation is between 1 and 30 mg/mL, sodium chloride content is between 0.7% and 0.9%, though greater or lesser concentrations may also be used, and pH is adjusted to about 9.5 but at least between 8 and 11 by buffering with an alkaline buffer such as sodium hydroxide or other buffers described above, until the desirable pH is reached and can be maintained over time.

In addition to the agents described in U.S. patent application Ser. No. 10/765,720, additional agents are useful when delivered with the methods presented in Ser. No. 10/765,720 as well as in this invention. These agents include toxins entering cells through sodium channels, including tetrodotoxin and batrachotoxin, toxins entering cells through potassium channels, including maurotoxin, agitoxin, charybdotoxin, margatoxin, slotoxin, sycllatoxin and hefutoxin, and toxins entering cells through calcium channels, including calciseptine, taicatoxin, calcicludine and PhTx3.

Other agents that benefit from the methods described here and in referenced patent applications include adrenergic blockers and stimulators (e.g., doxazosin, guanadrel, guanethidine, pheoxybenzamine, prazosin plus polythiazide, terazosin, methyldopa, clonidine, guanabenz, guanfacine); Alpha-/beta-adrenergic blockers (e.g., Labetalol); angiotensin converting enzyme (ACE) inhibitors (e.g., benazepril, catopril, enalapril, enalaprilat, fosinopril, lisinopril, moexipril, quinapril, ramipril, and combinations with calcium channel blockers and diuretics; ACE-receptor antagonists (e.g., losartan); Beta blockers (e.g., acebutolol, atenolol, betaxolol, bisoprolol, carteolol, esmolol, fimolol, pindolol, propranolol, penbatolol, metoprolol, nadolol, sotalol); Calcium channel blockers (e.g., Amiloride, amlodipine, bepridil, diltiazem, isradipine, nifedipine, verapamil, felodipine, nicardipine, nimodipine); Antiarrythmics, groups I-IV (e.g., bretylium, disopyramide, encamide, flecamide, lidocaine, mexiletine, moricizine, propafenone, procainamide, quinidine, tocamide, esmolol, propranolol, acebutolol, amiodarone, sotalol, verapamil, diltiazem, pindolol, bupranolol hydrochloride, trichlormethiazide, furosemide, prazosin hydrochloride, metoprolol tartrate, carteolol hydrochloride, oxprenolol hydrochloride, and propranolol hydrochloride); and miscellaneous antiarrythmics and cardiotonics (e.g., adenosine, digoxin; metildigoxin, caffeine, dopamine hydrochloride, dobutamine hydrochloride, octopamine hydrochloride, diprophylline, ubidecarenon, digitalis), and sensory denervation agents including capsaicin.

Other agents have been shown to create partial or complete sympathectomy as well, and may be used as the therapeutic agent as described herein. These include an immunosympathectomy agent such as anti-nerve growth factor (anti-NGF); auto-immune sympathectomy agents such as anti-dopamine beta-hydroxylase (anti-D.beta.H) and anti-acetylcholinesterase (anti-AChe); chemical sympathectomy agents such as 6-hydroxydopamine (6-OHDA), bretylium tosylate, guanacline, and N-(2-chloroethyl)-N-ethyl-2-bromobenzylamine (DSP4); and immunotoxin sympathectomy agents such as OX7-SAP, 192-SAP, anti-dopamine beta-hydroxylase saporin (DBH-SAP), and anti-dopamine beta-hydroxylase immunotoxin (DHIT). A full description of these agents is found in Picklo M J, J Autonom Nery Sys 1997; 62:111-125. Phenol and ethanol have also been used to produce chemical sympathectomy and are also useful in the methods of this invention. Other sympatholytic agents include alpha-2-agonists such as clonidine, guanfacine, methyldopa, guanidine derivatives like betanidine, guanethidine, guanoxan, debrisoquine, guanoclor, guanazodine, guanoxabenz and the like; imadazoline receptor agonists such as moxonidine, relmenidine and the like; ganglion-blocking or nicotinic antagonists such as mecamylamine, trimethaphan and the like; MAOI inhibitors such as pargyline and the like; adrenergic uptake inhibitors such as rescinnamine, reserpine and the like; tyrosine hydroxylase inhibitors such as metirosine and the like; alpha-1 blockers such as prazosin, indoramin, trimazosin, doxazosin, urapidil and the like; non-selective alpha blockers such as phentolamine and the like; serotonin antagonists such as ketanserin and the like; and endothelin antagonists such as bosentan, ambrisentan, sitaxentan, and the like.

Additionally, agents that sclerose nerves can be used to create neurolysis or sympatholysis. Sclerosing agents that lead to the perivascular lesioning of nerves include quinacrine, chloroquine, sodium tetradecyl sulfate, ethanolamine oleate, sodium morrhuate, polidocanol, phenol, ethanol, or hypertonic solutions.

Such agents may be used for denervation in a variety of locations in a subject. While much description herein is directed to renal denervation, the inventions herein are not meant to be limited to this location or these nerves. Other target nerves are contemplated, such as bronchial nerve denervation, or transbronchoscopic denervation, at least.

Agent Delivery, Modulator Delivery (Any Order):

Provided herein is a method of delivering a therapeutic agent to a subject that locally denervates nerves comprising delivering the therapeutic agent to the subject and delivering a modulator or composition that is effective to modulate the local pH of the tissue surrounding the nerves that are the target of denervation. The delivery of the therapeutic agent and/or of the modulator or composition may be transluminal using one or more device as described herein, for example. Such delivery of said composition may be during, before, or after the delivery of the agent. The therapeutic agent may be guanethidine, or another therapeutic agent noted herein. The modulation may change the pH of the tissue to at least 7, to between 7 and 11, or between 8 and 10, or to between 8.5 and 9.5, for non-limiting example. In some embodiments, the modulator is a buffer or a buffer agent. In some embodiment the composition comprises a buffer or a buffer agent. In some embodiments, delivering the therapeutic agent and delivering the modulator or composition is done simultaneously, concurrently, or sequentially, using the same injection devices or using separate injection devices.

Modulator Delivery Alone

In another embodiment, the method comprises delivery of a composition that locally modulates the pH of the tissue surrounding the nerves that are the target of denervation without the need for a therapeutic agent. In such an embodiment, the composition itself achieves the therapeutic goal of denervating the target nerves.

Buffered Agent Delivery

In another embodiment, the method comprises delivery of a composition that has been pH-modulated prior to delivery to the tissue surrounding the nerve. Such composition may comprise a pH modulator and the therapeutic agent. In some embodiments, a composition comprises a therapeutic agent and a pH modulator. In some embodiments, a composition comprises a therapeutic agent at a pH of at least 7, between 7 and 11, between 8 and 10, or between 8.5 and 9.5, for non-limiting example. In some embodiments an aqueous solution comprising the therapeutic agent alone (without the modulator) is more acidic than the composition comprising the aqueous solution of therapeutic agent and the modulator. In some embodiments an aqueous solution comprising the therapeutic agent alone (without the modulator) is more alkaline than the composition comprising the aqueous solution of therapeutic agent and the modulator. The pH modulator may be a buffer, an alkaline buffer, such as NaOH, or another buffer that adjusts the composition to a target pH, to at least 7, to between 7 and 11, to between 8 and 10, or to between 8.5 and 9.5, for non-limiting example. The pH modulator may be an acid, an acidic agent, or a salt of an acid or acidic agent. In such embodiment, the composition comprises a therapeutic agent and a pH modulator that modulates the pH of the composition to at least 7, to between 7 and 11, to between 8 and 10, or to between 8.5 and 9.5, for non-limiting example. Such composition may be delivered to the tissue surrounding the nerves that are the target of denervation. A single injection of said composition, in some embodiments, may be effective in denervating the target nerve or nerves. In some embodiments, the therapeutic agent comprises guanethidine, guanethidine monosulfate, or guanethidine hemisulfate, or any agent (i.e. therapeutic agent) noted elsewhere herein. In some embodiments, the modulator is a buffer or a buffer agent. In some embodiments the buffer comprises sodium hydroxide.

Guanethidine Hemisulfate Agent Delivery

In some embodiments, the method comprises delivery of a composition comprising a therapeutic agent in an aqueous solution having a pH that is alkaline. In some embodiments, the method comprises delivery of a composition comprising a therapeutic agent in an aqueous solution having a pH that is acidic. In such embodiments, a pH modulator is not necessary to achieve the pH that enhances the effectiveness of the therapeutic agent in denervating a nerve in the tissue to which the composition is delivered. Such a composition may comprise a therapeutic agent in an aqueous solution having a pH of at least 7, between 7 and 11, between 8 and 10, or between 8.5 and 9.5, for non-limiting example. Provided herein is a composition comprising a guanidine with pH>8. In some embodiments, the guanidine is guanethidine. In some embodiments, the guanethidine includes monosulfate. In some embodiments, the guanethidine includes hemisulfate in a solution configured for denervation. In some embodiments, the guanethidine includes hemisulfate in a solution suitable for denervation. In some embodiments, the pH>9. In some embodiments, the pH>10.

In some embodiments, the composition further comprises an alkaline buffer. In some embodiments, the alkaline buffer comprises NaOH. In some embodiments, the alkaline buffer comprises NaOH in a molar ratio to the guanidine concentration of 50% or greater. In some embodiments, the alkaline buffer comprises NaOH in an equimolar or greater concentration to the guanidine.

In some embodiments, the composition further comprises a contrast medium. In some embodiments, the composition further comprises sodium chloride. In some embodiments, the sodium chloride is 0.7% to 0.9% of the solution. In some embodiments, the guanethidine monosulfate is in concentration of 0.1 mg/mL to 50 mg/Mr. In some embodiments, the guanethidine monosulfate is in concentration of 1 mg/mL to 20 mg/mL.

Provided herein is a method for modulating local tissue physiology comprising the delivery of preparation comprising a liquid, gel, or semisolid into the tissue. In some embodiments, the preparation buffers the local tissue physiology by raising or lowering the pH of the local tissue. In some embodiments, the preparation comprises a therapeutic agent that has its index effect at a physiological condition modulated by the delivery of such preparation, but not having an index effect at neutral physiological condition. In some embodiments, the preparation further includes a therapeutic agent that has additional or enhanced index effect at a physiological condition modulated by the delivery of such preparation, but not having such additional or enhanced index effect at neutral physiological condition. In some embodiments, the gel comprises a hydrogel. In some embodiments, the hydrogel consumes protons as it resorbs in the tissue. In some embodiments, the hydrogel is alkaline. In some embodiments, the preparation includes guanethidine monosulfate. In some embodiments, the preparation has a pH>8. In some embodiments, the preparation includes a contrast medium.

Provided herein is a method of creating renal denervation comprising the localized delivery of an acid or base with sufficiently low or high pH to create localized nerve damage or destruction.

Provided herein is a method of creating renal denervation comprising the localized delivery of a non-isotonic or non-isoosmolar solution that creates neuronal destruction while sparing other local tissues.

Provided herein is a method of treating hypertension comprising the delivery of a preparation of guanethidine monosulfate at pH>8 or guanethidine hemisulfate at pH>8 into the renal artery adventitia and perivascular tissues.

In some embodiments, the method further comprises delivery from an intravascular aspect.

Provided herein is a method of treating heart failure comprising the delivery of a preparation of guanethidine monosulfate at pH>8 or guanethidine hemisulfate at pH>8 into the renal artery adventitia and perivascular tissues.

Provided herein is a method of treating insulin resistance comprising the delivery of a preparation of guanethidine monosulfate at pH>8 or guanethidine hemisulfate at pH>8 into the renal artery adventitia and perivascular tissues.

Provided herein is a method of treating systemic inflammation comprising the delivery of a preparation of guanethidine monosulfate at pH>8 or guanethidine hemisulfate at pH>8 into the renal artery adventitia and perivascular tissues.

Provided herein is a method of treating sleep apnea comprising the delivery of a preparation of guanethidine monosulfate at pH>8 or guanethidine hemisulfate at pH>8 into the renal artery adventitia and perivascular tissues.

Provided herein is a method of creating renal denervation comprising the localized delivery of an agent chosen from the following: a hypertonic saline, a detergent, a solvent, ethanol, a strong acid, a strong base, a buffer agent, an alkaline buffer agent, an acidic buffer agent, a composition having a sodium chloride content between 0.7% and 0.9%, a composition having pH of about 9.5, a composition having pH that is adjusted to about 9.5 by buffering with an alkaline buffer agent, a composition having pH that is adjusted to about 9.5 by buffering with sodium hydroxide, or a composition having pH of between 8 and 11.

In some embodiments, the buffer agent comprises one or more of sodium hydroxide, sodium bicarbonate, magnesium hydroxide, sulfuric acid, hydrochloric acid, citric acid, acetic acid, sodium citrate, sodium acetate, boric acid, potassium dihydrogen phosphate, diethyl barbituric acid, 3-{[tris(hydroxymethyl)methyl]amino}propanesulfonic acid, N,N-bis (2-hydroxyethyl)glycine, tris(hydroxymethyl)aminomethane, N-tris(hydroxymethyl)methylglycine, 2-[Bis(2-hydroxyethyl)amino]-2-(hydroxymethyl)-1,3-propanediol, 3-[N-Tris(hydroxymethyl)methylamino]-2-hydroxypropanesulfonic acid, 4-2-hydroxyethyl-1-piperazineethanesulfonic acid, 2-{[tris(hydroxymethyl)methyl] amino}ethanesulfonic acid, 3-(N-morpholino) propanesulfonic acid, piperazine-N,N'-bis(2-ethanesulfonic acid), dimethylarsinic acid, saline sodium citrate, 2-(N-morpholino)ethanesulfonic acid, and glycine.

Provided herein is a method of creating renal denervation comprising the localized delivery of an agent chosen from the following: guanethidine in a concentration ranging from 1 µg/mL to 50 mg/mL at pH of greater than 7, guanethidine in a concentration ranging from 1 mg/mL to 30 mg/mL at pH of greater than 7, a composition comprising guanethidine having a sodium chloride content between 0.7% and 0.9%, a composition comprising guanethidine having pH of about 9.5, a composition comprising guanethidine having pH that is adjusted to about 9.5 by buffering with an alkaline buffer agent, a composition comprising guanethidine having pH that is adjusted to about 9.5 by buffering with sodium hydroxide, or a composition comprising guanethidine having pH of between 8 and 11.

Provided herein is a method of creating renal denervation comprising the localized delivery of a first toxin entering cells through sodium channels, wherein such first toxin comprises one or more of: tetrodotoxin and batrachotoxin, a second toxin entering cells through potassium channels, wherein such second toxin comprises one or more of: aurotoxin, agitoxin, charybdotoxin, margatoxin, slotoxin, sycllatoxin and hefutoxin, and/or a third toxin entering cells through calcium channels, wherein such third toxin comprises one or more of: calciseptine, taicatoxin, calcicludine and PhTx3.

Provided herein is a method of creating renal denervation comprising the localized delivery of an agent comprising an adrenergic blocker, an androgenic inhibitor, an adrenergic stimulator, an Alpha-/beta-adrenergic blocker, an angiotensin converting enzyme (ACE) inhibitor, an ACE-receptor antagonist, a Beta blocker, a calcium channel blocker, an antiarrythmic of groups I-IV, an antiarrythmic, a cardiotonic, an alpha-2-agonists, a guanidine derivative, an imadazoline receptor agonist, a ganglion-blocking agent, nicotinic antagonist, ganglion-blocking agents, nicotinic antagonist, a MAOI inhibitor, an adrenergic uptake inhibitor, a tyrosine hydroxylase inhibitors, an alpha-1 blocker, a non-selective alpha blocker, a serotonin antagonist, an endothelin antagonist, a sclerosing agent, or a sensory denervation agent.

Provided herein is a method of creating renal denervation comprising the localized delivery of an agent comprising doxazosin, guanadrel, guanethidine, pheoxybenzamine, prazosin plus polythiazide, terazosin, methyldopa, clonidine, guanabenz, guanfacine, Labetalol, benazepril, catopril, enalapril, enalaprilat, fosinopril, lisinopril, moexipril, quinapril, ramipril, and combinations with calcium channel blockers and diuretics, losartan, acebutolol, atenolol, betaxolol, bisoprolol, carteolol, esmolol, fimolol, pindolol, propranolol, penbatolol, metoprolol, nadolol, sotalol, Amiloride, amlodipine, bepridil, diltiazem, isradipine, nifedipine, verapamil, felodipine, nicardipine, nimodipine, bretylium, disopyramide, encamide, flecamide, lidocaine, mexiletine, moricizine, propafenone, procainamide, quinidine, tocamide, esmolol, propranolol, acebutolol, amiodarone, sotalol, verapamil, diltiazem, pindolol, bupranolol hydrochloride, trichlormethiazide, furosemide, prazosin hydrochloride, metoprolol tartrate, carteolol hydrochloride, oxprenolol hydrochloride, and propranolol hydrochloride, adenosine, digoxin; metildigoxin, caffeine, dopamine hydrochloride, dobutamine hydrochloride, octopamine hydrochloride, diprophylline, ubidecarenon, digitalis, capsaicin, anti-nerve growth factor, anti-dopamine beta-hydroxylase, anti-acetylcholinesterase, 6-hydroxyldopamine (6-OHDA), bretylium tosylate, guanacline, and N-(2-chloroethyl)-N-ethyl-2-bromobenzylamine (DSP4), OX7-SAP, 192-SAP, anti-dopamine beta-hydroxylase saporin (DBH-SAP), and anti-dopamine beta-hydroxylase immunotoxin (DHIT), phenol, ethanol, clonidine, guanfacine, methyldopa, betanidine, guanoxan, debrisoquine, guanoclor, guanazodine, guanoxabenz, moxonidine, relmenidine, mecamylamine, trimethaphan, pargyline, rescinnamine, reserpine, metirosine, prazosin, indoramin, trimazosin, doxazosin, urapidil, phentolamine, ketanserin, bosentan, ambrisentan, sitaxentan, quinacrine, chloroquine, sodium tetradecyl sulfate, ethanolamine oleate, sodium morrhuate, polidocanol, or a hypertonic solution.

In some embodiments, the agent itself or a composition comprising such agent has a pH of at least 7, a pH of at most 11, a pH of at least 7 and at most 11, a pH of at least 8 and at most 10, a pH that is effective to denervate nerves to which such agent is delivered, or a pH that is adjusted to a level that is effective to denervate nerves to which such agent is delivered.

Provided herein is a method for enhancing the uptake of therapeutic agents into tissue comprising modulating pH of the tissue by creating a zone of the tissue having a center and an outer edge, wherein the zone comprises a modulated pH as compared to a pre-modulation pH of the tissue prior to modulation or as compared to a neutral pH, wherein zone comprises a gradient of pH that is most modulated at the center of the zone and reduces to the pre-modulation pH of the tissue or to neutral pH at the outer edge of the zone, and wherein enhanced uptake of a therapeutic agent occurs in the zone as compared to uptake that would occur into tissue at the pre-modulation pH or at neutral pH.

Provided herein is a method for enhancing the uptake of therapeutic agents into tissue comprising—modulating pH of the tissue by creating a zone of the tissue having a center and an outer edge, and—delivering a therapeutic agent into the zone; wherein the zone comprises a modulated pH as compared to a pre-modulation pH of the tissue prior to modulation or as compared to a neutral pH, wherein zone comprises a gradient of pH that is most modulated at the center of the zone and reduces to the pre-modulation pH of the tissue or to neutral pH at the outer edge of the zone, and wherein enhanced uptake of the therapeutic agent occurs in the zone as compared to uptake that would occur into tissue at the pre-modulation pH or at neutral pH.

In some embodiments, the method comprises delivering the therapeutic agent into the zone. In some embodiments, the therapeutic agent is delivered systemically and modulating the tissue pH enhances a buildup of the therapeutic agent in the zone or improves a therapeutic index in the zone.

In some embodiments, the enhanced uptake occurs within a portion of the zone having the modulated pH that is modulated from the pre-modulation pH by a preselected amount. In some embodiments, the enhanced uptake occurs within a portion of the zone having the modulated pH that is modulated from a neutral pH by a preselected amount. In some embodiments, the preselected amount is a difference of pH between the modulated pH and the pre-modulation pH or between the modulated pH and the neutral pH of one or more of: 0.5, 1.0, 1.5, 2.0, 2.5, 3.0, 3.5, 4.0, 4.5, −0.5, −1.0, −1.5, −2.0, −2.5, −3.0, −3.5, −4.0, −4.5, from 0.5 to 5.0, from 1.5 to 4.5, from 2.0 to 4.0, about 0.5, from −0.5 to −5.0, from −1.5 to −4.5, from −2.0 to −4.0, about 0.5, about 1.0, about 1.5, about 2.0, about 2.5, about 3.0, about 3.5, about 4.0, about 4.5, about −0.5, about −1.0, about −1.5, about −2.0, about −2.5, about −3.0, about −3.5, about −4.0, and about −4.5. In some embodiments, the modulated pH is a pH that is lower than the tissue outside the zone, which is higher than the tissue outside the zone, that is lower than the pH of the tissue prior to modulation, or that is higher than the pH of the tissue prior to modulation. In some embodiments, the modulated pH is more acidic than the pH of tissue outside the zone, or is more alkaline than the pH of tissue outside the zone. The method of Claim 42, wherein the modulated pH at least 7, at most 11, at least 7 and at most 11, at least 8 and at most 10, or a predetermined pH that is effective to denervate nerves to which such therapeutic agent is delivered. In some embodiments, the therapeutic agent comprises guanethidine. In some embodiments, the guanethidine includes monosulfate or hemisulfate. In some embodiments, the modulated pH at least 7, at most 11, at least 7 and at most 11, at least 8 and at most 10, or a predetermined pH that is effective to denervate nerves to which such therapeutic agent is delivered.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

A better understanding of the features and advantages of the compositions, systems, devices, and methods provided will be obtained by reference to the following detailed description that sets forth illustrative embodiments and the accompanying drawings of which:

FIG. 12 depicts an embodiment catheter that can be used to accomplish the methods of the invention being deployed from a sheathed and deflated configuration in cross-section view to an inflated and deployed configuration in cross-section view successively from top to bottom on the left of the figure, and showing a picture of such embodiment in the right images of the figure.

DETAILED DESCRIPTION OF THE INVENTION

This application incorporates FIGS. 1-8 and all text from commonly owned prior application Ser. No. 12/765,708, filed on Apr. 22, 2010, and published as US 2011/0104060, the full disclosure of which is incorporated herein by reference. The description and FIGS. 1-8 below provide three representative embodiments of catheters having microneedles suitable for the delivery of a neuromodulating agent into a perivascular space or adventitial tissue. A more complete description of the catheters and methods for their fabrication is provided in U.S. Pat. Nos. 7,141,041; 6,547,803; 7,547,294; 7,666,163 and 7,691,080, the full disclosures of which have been incorporated herein by reference.

Figure 1A:
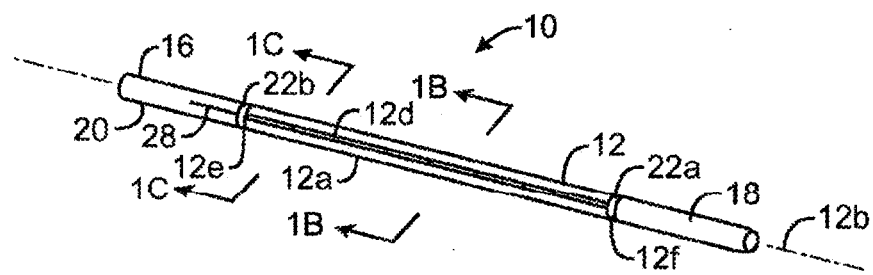
FIG. 1A is a schematic, perspective view of an intraluminal injection catheter suitable for use in the methods and systems of the present invention.
Figure 1B:
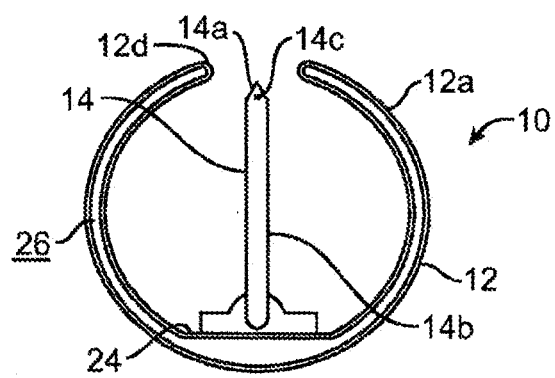
FIG. 1B is a cross-sectional view along line 1B-1B of FIG. 1A.
Figure 1C:
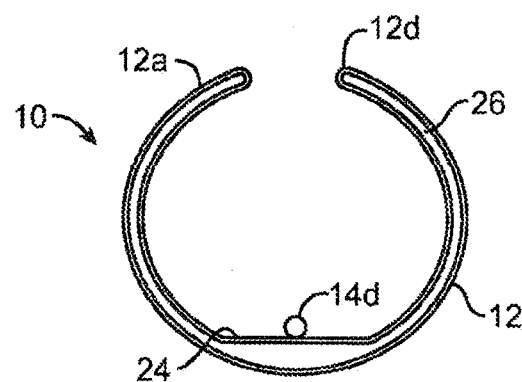
FIG. 1C is a cross-sectional view along line 1C-1C of FIG. 1A.
Figure 2A:
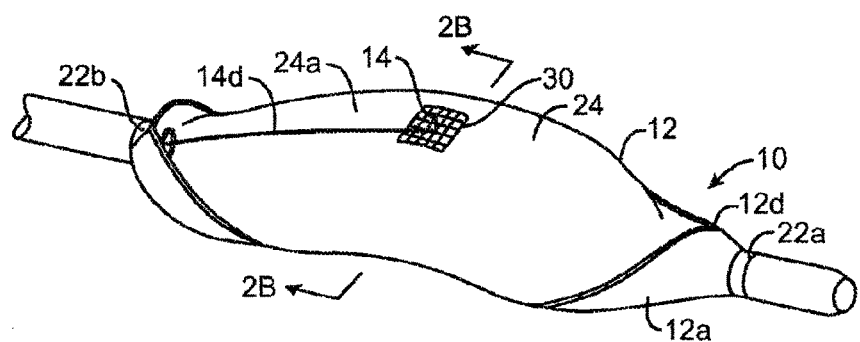
FIG. 2A is a schematic, perspective view of the catheter of FIGS. 1A-1C shown with the injection needle deployed.
Figure 2B:
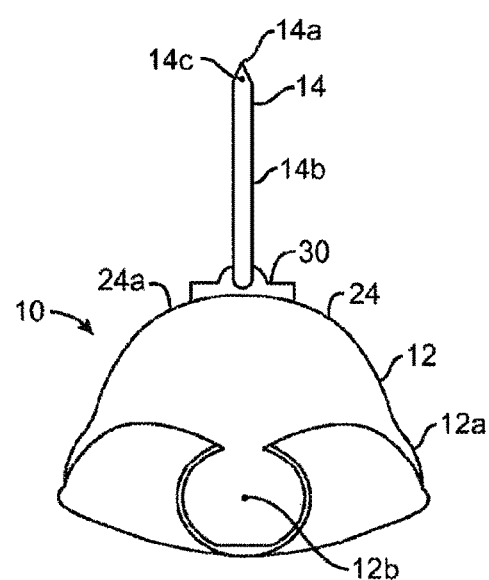
FIG. 2B is a cross-sectional view along line 2B-2B of FIG. 2A.

As shown in FIGS. 1A-2B, a microfabricated intraluminal catheter 10 includes an actuator 12 having an actuator body 12a and central longitudinal axis 12b. The actuator body more or less forms a U-shaped or C-shaped outline having an opening or slit 12d extending substantially along its length. A microneedle 14 is located within the actuator body, as discussed in more detail below, when the actuator is in its unactuated condition (furled state) (FIG. 1B). The microneedle is moved outside the actuator body when the actuator is operated to be in its actuated condition (unfurled state) (FIG. 2B).

The actuator may be capped at its proximal end 12e and distal end 12f by a lead end 16 and a tip end 18, respectively, of a therapeutic catheter 20. The catheter tip end serves as a means of locating the actuator inside a body lumen by use of a radio opaque coatings or markers. The catheter tip also forms a seal at the distal end 12f of the actuator. The lead end of the catheter provides the necessary interconnects (fluidic, mechanical, electrical or optical) at the proximal end 12e of the actuator.

Retaining rings 22a and 22b are located at the distal and proximal ends, respectively, of the actuator. The catheter tip is joined to the retaining ring 22a, while the catheter lead is joined to retaining ring 22b. The retaining rings are made of a thin, on the order of 10 to 100 microns (μm), substantially flexible but relatively non-distensible material, such as Parylene (types C, D or N), or a metal, for example, aluminum, stainless steel, gold, titanium or tungsten. The retaining rings form a flexible but relatively non-distensible substantially "U"-shaped or "C"-shaped structure at each end of the actuator. The catheter may be joined to the retaining rings by, for example, a butt-weld, an ultra sonic weld, integral polymer encapsulation or an adhesive such as an epoxy or cyanoacrylate.

The actuator body further comprises a central, expandable section 24 located between retaining rings 22a and 22b. The expandable section 24 includes an interior open area 26 for rapid expansion when an activating fluid is supplied to that area. The central section 24 is made of a thin, semi-flexible but relatively non-distensible or flexible but relatively non-distensible, expandable material, such as a polymer, for instance, Parylene (types C, D or N), silicone, polyurethane or polyimide. The central section 24, upon actuation, is expandable somewhat like a balloon-device.

The central section is capable of withstanding pressures of up to about 200 psi upon application of the activating fluid to the open area 26. The material from which the central section is made of is flexible but relatively non-distensible or semi-flexible but relatively non-distensible in that the central section returns substantially to its original configuration and orientation (the unactuated condition) when the activating fluid is removed from the open area 26. Thus, in this sense, the central section is very much unlike a balloon which has no inherently stable structure.

The open area 26 of the actuator is connected to a delivery conduit, tube or fluid pathway 28 that extends from the catheter's lead end to the actuator's proximal end. The activating fluid is supplied to the open area via the delivery tube. The delivery tube may be constructed of Teflon©. or other inert plastics. The activating fluid may be a saline solution or a radio-opaque dye.

The microneedle 14 may be located approximately in the middle of the central section 24. However, as discussed below, this is not necessary, especially when multiple microneedles are used. The microneedle is affixed to an exterior surface 24a of the central section. The microneedle is affixed to the surface 24a by an adhesive, such as cyanoacrylate. Alternatively, the microneedle maybe joined to the surface 24a by a metallic or polymer mesh-like structure 30 (See FIG. 2A), which is itself affixed to the surface 24a by an adhesive. The mesh-like structure may be-made of, for instance, steel or nylon.

The microneedle includes a sharp tip 14a and a shaft 14b. The microneedle tip can provide an insertion edge or point. The shaft 14b can be hollow and the tip can have an outlet port 14c, permitting the injection of a neuromodulating agent or drug into a patient. The microneedle, however, does not need to be hollow, as it may be configured like a neural probe to accomplish other tasks. As shown, the microneedle extends approximately perpendicularly from surface 24a. Thus, as described, the microneedle will move substantially perpendicularly to an axis of a lumen into which has been inserted, to allow direct puncture or breach of body lumen walls.

The microneedle further includes a neuromodulating agent or drug supply conduit, tube or fluid pathway 14d which places the microneedle in fluid communication with the appropriate fluid interconnect at the catheter lead end. This supply tube may be formed integrally with the shaft 14b, or it may be formed as a separate piece that is later joined to the shaft by, for example, an adhesive such as an epoxy. The microneedle 14 may be bonded to the supply tube with, for example, an adhesive such as cyanoacrylate.

The needle 14 may be a 30-gauge, or smaller, steel needle. Alternatively, the microneedle may be microfabricated from polymers, other metals, metal alloys or semiconductor materials. The needle, for example, may be made of Parylene, silicon or glass. Microneedles and methods of fabrication are described in U.S. application Ser. No. 09/877,653, filed Jun. 8, 2001, entitled "Microfabricated Surgical Device", the entire disclosure of which is incorporated herein by reference.

Figure 3:
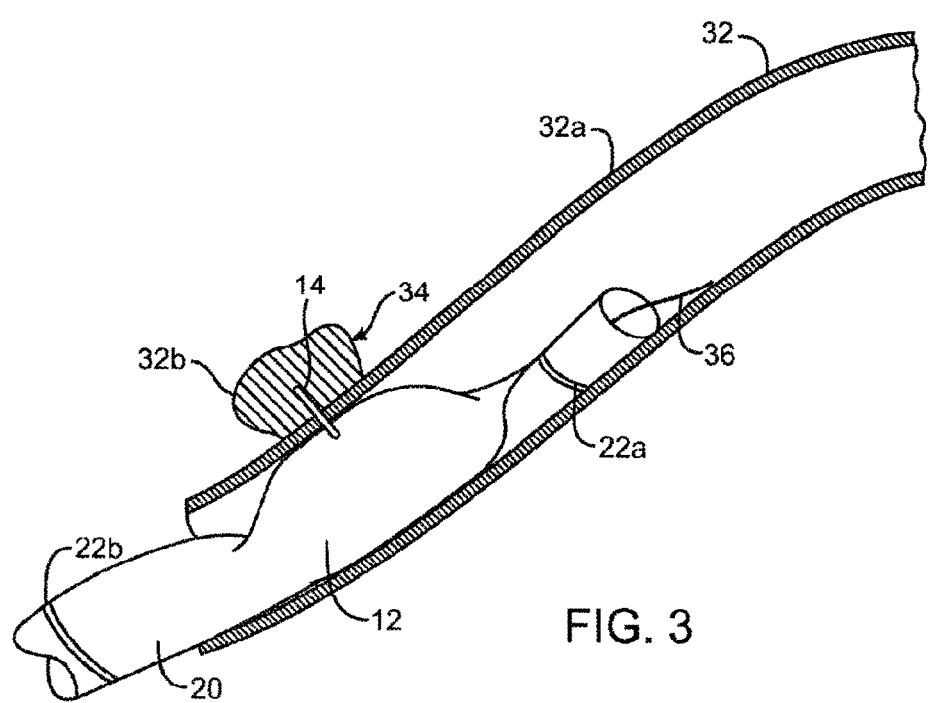
FIG. 3 is a schematic, perspective view of the intraluminal catheter of FIGS. 1A-1C injecting therapeutic agents into an adventitial space surrounding a body lumen in accordance with the methods of the present invention.

The catheter 20, in use, is inserted through an opening in the body (e.g. for bronchial or sinus treatment) or through a percutaneous puncture site (e.g. for artery or venous treatment) and moved within a patient's body passageways 32, until a specific, targeted region 34 is reached (see FIG. 3). The targeted region 34 may be the site of tissue damage or more usually will be adjacent the sites typically being within 100 mm or less to allow migration of the therapeutic or diagnostic agent. As is well known in catheter-based interventional procedures, the catheter 20 may follow a guide wire 36 that has previously been inserted into the patient. Optionally, the catheter 20 may also follow the path of a previously-inserted guide catheter (not shown) that encompasses the guide wire or endoscope that has been inserted into the body through a natural orifice.

During maneuvering of the catheter 20, well-known methods of x-ray fluoroscopy or magnetic resonance imaging (MRI) can be used to image the catheter and assist in positioning the actuator 12 and the microneedle 14 at the target region. As the catheter is guided inside the patient's body, the microneedle remains furled or held inside the actuator body so that no trauma is caused to the body lumen walls.

After being positioned at the target region 34, movement of the catheter is terminated and the activating fluid is supplied to the open area 26 of the actuator, causing the expandable section 24 to rapidly unfurl, moving the microneedle 14 in a substantially perpendicular direction, relative to the longitudinal central axis 12b of the actuator body 12a, to puncture a body lumen wall 32a. It may take only between approximately 100 milliseconds and five seconds for the microneedle to move from its furled state to its unfurled state.

The microneedle aperture, may be designed to enter body lumen tissue 32b as well as the adventitia, media, or intima surrounding body lumens. Additionally, since the actuator is "parked" or stopped prior to actuation, more precise placement and control over penetration of the body lumen wall are obtained.

After actuation of the microneedle and delivery of the agents to the target region via the microneedle, the activating fluid is exhausted from the open area 26 of the actuator, causing the expandable section 24 to return to its original, furled state. This also causes the microneedle to be withdrawn from the body lumen wall. The microneedle, being withdrawn, is once again sheathed by the actuator.

Various microfabricated devices can be integrated into the needle, actuator and catheter for metering flows, capturing samples of biological tissue, and measuring pH. The device 10, for instance, could include electrical sensors for measuring the flow through the microneedle as well as the pH of the neuromodulating agent being deployed. The device 10 could also include an intravascular ultrasonic sensor (IVUS) for locating vessel walls, and fiber optics, as is well known in the art, for viewing the target region. For such complete systems, high integrity electrical, mechanical and fluid connections are provided to transfer power, energy, and neuromodulating agents or biological agents with reliability.

By way of example, the microneedle may have an overall length of between about 200 and 3,000 microns (μm). The interior cross-sectional dimension of the shaft 14b and supply tube 14d may be on the order of 20 to 250 μm, while the tube's and shaft's exterior cross-sectional dimension may be between about 100 and 500 μm. The overall length of the actuator body may be between about 5 and 50 millimeters (mm), while the exterior and interior cross-sectional dimensions of the actuator body can be between about 0.4 and 4 mm, and 0.5 and 5 mm, respectively. The gap or slit through which the central section of the actuator unfurls may have a length of about 4-40 mm, and a cross-sectional dimension of about 50 µm to 4 mm. The diameter of the delivery tube for the activating fluid may be between 100 and 500 µm. The catheter size may be between 1.5 and 15 French (Fr).

Figure 4A:
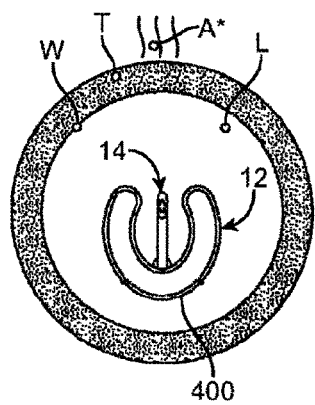
FIGS. 4A-4D are cross-sectional views of the inflation process of an intraluminal injection catheter useful in the methods of the present invention.

Referring to FIGS. 4A-4D, an elastomeric component is integrated into the wall of the intraluminal catheter of FIG. 1-3. In FIG. 4A-D, the progressive pressurization of such a structure is displayed in order of increasing pressure. In FIG. 4A, the balloon is placed within a body lumen L. The lumen wall W divides the lumen from periluminal tissue T, or adventitia A*, depending on the anatomy of the particular lumen. The pressure is neutral, and the non-distensible structure forms a U-shaped involuted balloon 12 similar to that in FIG. 1 in which a needle 14 is sheathed. While a needle is displayed in this diagram, other working elements including cutting blades, laser or fiber optic tips, radiofrequency transmitters, or other structures could be substituted for the needle. For all such structures, however, the elastomeric patch 400 will usually be disposed on the opposite side of the involuted balloon 12 from the needle 14.

Figure 4B:
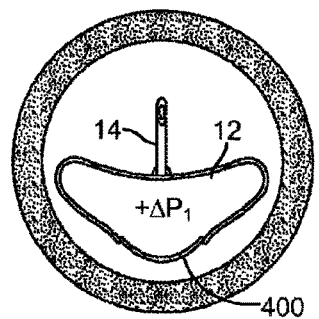
Figure 4C:
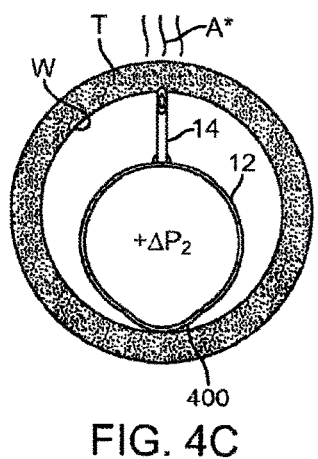
Figure 4D:
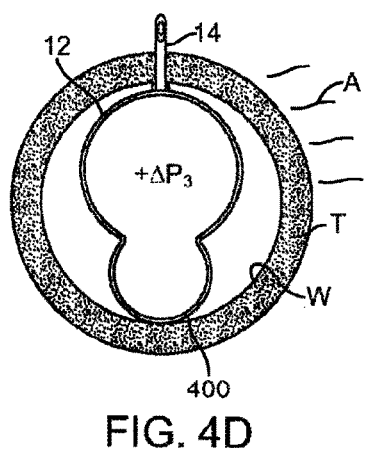

Actuation of the balloon 12 occurs with positive pressurization. In FIG. 4B, pressure ($+\Delta P_1$) is added, which begins to deform the flexible but relatively non-distensible structure, causing the balloon involution to begin its reversal toward the lower energy state of a round pressure vessel. At higher pressure $+\Delta P_2$ in FIG. 4C, the flexible but relatively non-distensible balloon material has reached its rounded shape and the elastomeric patch has begun to stretch. Finally, in FIG. 4D at still higher pressure $+\Delta P_3$, the elastomeric patch has stretched out to accommodate the full lumen diameter, providing an opposing force to the needle tip and sliding the needle through the lumen wall and into the adventitia A. Typical dimensions for the body lumens contemplated in this figure are between 0.1 mm and 50 mm, more often between 0.5 mm and 20 mm, and most often between 1 mm and 10 mm. The thickness of the tissue between the lumen and adventitia is typically between 0.001 mm and 5 mm, more often between 0.01 mm and 2 mm and most often between 0.05 mm and 1 mm. The pressure $+\Delta P$ useful to cause actuation of the balloon is typically in the range from 0.1 atmospheres to 20 atmospheres, more typically in the range from 0.5 to 20 atmospheres, and often in the range from 1 to 10 atmospheres.

Figure 5A:
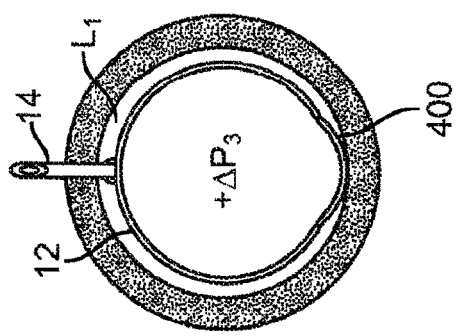
FIGS. 5A-5C are cross-sectional views of the inflated intraluminal injection catheter useful in the methods of the present invention, illustrating the ability to treat multiple lumen diameters.
Figure 5B:
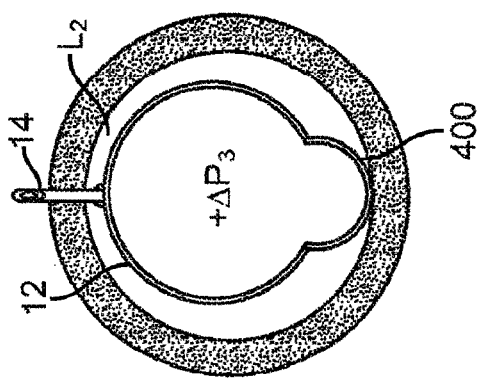
Figure 5C:
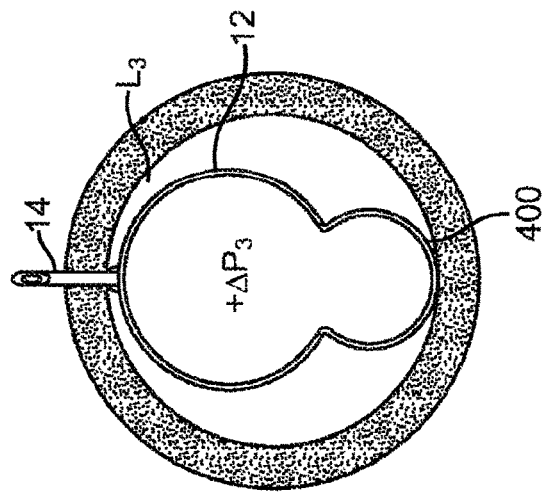

As illustrated in FIGS. 5A-5C, the dual modulus structure shown in FIGS. 4A-4D provides for low-pressure (i.e., below pressures that may damage body tissues) actuation of an intraluminal medical device to place working elements such as needles in contact with or through lumen walls. By inflation of a constant pressure, and the elastomeric material will conform to the lumen diameter to provide full apposition. Dual modulus balloon 12 is inflated to a pressure $+\Delta P_3$ in three different lumen diameters in FIGS. 5A, 5B, and 5C for the progressively larger inflation of patch 400 provides optimal apposition of the needle through the vessel wall regardless of diameter. Thus, a variable diameter system is created in which the same catheter may be employed in lumens throughout the body that are within a range of diameters. This is useful because most medical products are limited to very tight constraints (typically within 0.5 mm) in which lumens they may be used. A system as described in this invention may accommodate several millimeters of variability in the luminal diameters for which they are useful.

The above catheter designs and variations thereon, are described in published U.S. Pat. Nos. 6,547,803; 6,860,867; 7,547,294; 7,666,163 and 7,691,080, the full disclosures of which are incorporated herein by reference. Co-pending application Ser. No. 10/691,119, assigned to the assignee of the present application, describes the ability of substances delivered by direct injection into the adventitial and pericardial tissues of the heart to rapidly and evenly distribute within the heart tissues, even to locations remote from the site of injection. The full disclosure of that co-pending application is also incorporated herein by reference. An alternative needle catheter design suitable for delivering the therapeutic or diagnostic agents of the present invention will be described below. That particular catheter design is described and claimed in U.S. Pat. No. 7,141,041, the full disclosure of which is incorporated herein by reference.

Figure 6:
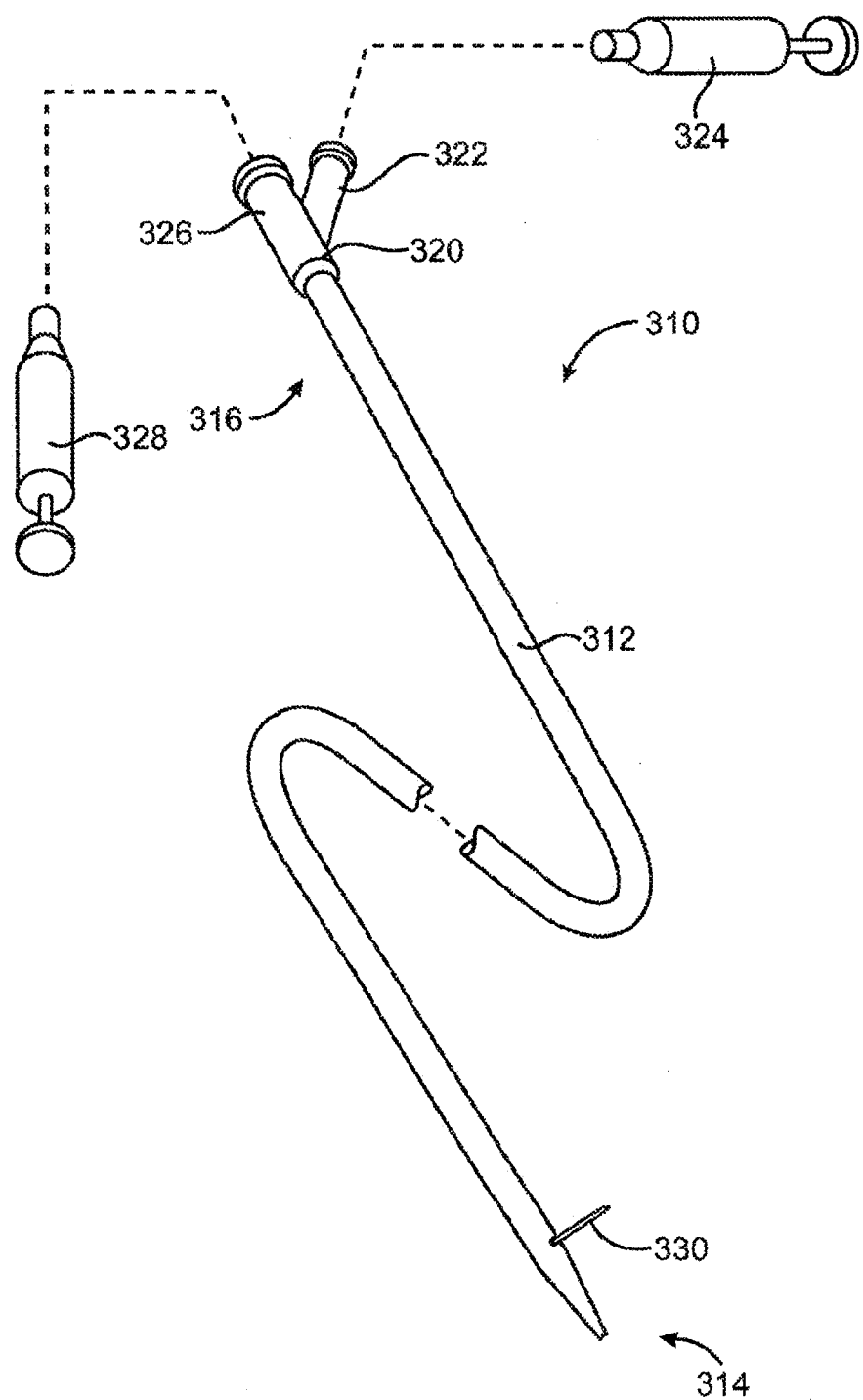
FIG. 6 is a perspective view of a needle injection catheter useful in the methods and systems of the present invention.

Referring now to FIG. 6, a needle injection catheter 310 constructed in accordance with the principles of the present invention comprises a catheter body 312 having a distal end 314 and a proximal 316. Usually, a guide wire lumen 313 will be provided in a distal nose 352 of the catheter, although over-the-wire and embodiments which do not require guide wire placement will also be within the scope of the present invention. A two-port hub 320 is attached to the proximal end 316 of the catheter body 312 and includes a first port 322 for delivery of a hydraulic fluid, e.g., using a syringe 324, and a second port 326 for delivering the neuromodulating agent, e.g., using a syringe 328. A reciprocatable, deflectable needle 330 is mounted near the distal end of the catheter body 312 and is shown in its laterally advanced configuration in FIG. 6.

Figure 7:
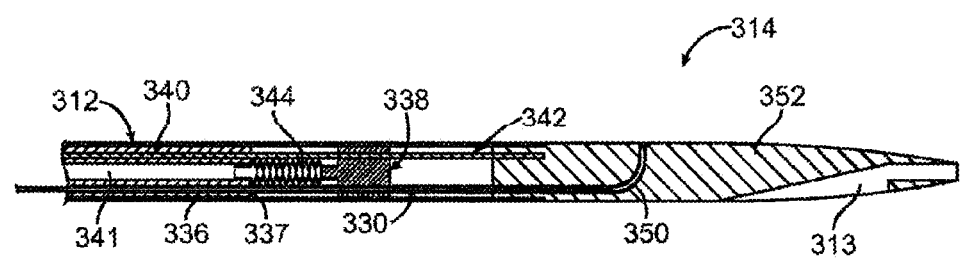
FIG. 7 is a cross-sectional view of the catheter FIG. 6 shown with the injection needle in a retracted configuration.

Referring now to FIG. 7, the proximal end 314 of the catheter body 312 has a main lumen 336 which holds the needle 330, a reciprocatable piston 338, and a hydraulic fluid delivery tube 340. The piston 338 is mounted to slide over a rail 342 and is fixedly attached to the needle 330. Thus, by delivering a pressurized hydraulic fluid through a lumen 341 tube 340 into a bellows structure 344, the piston 338 may be advanced axially toward the distal tip in order to cause the needle to pass through a deflection path 350 formed in a catheter nose 352.

Figure 8:
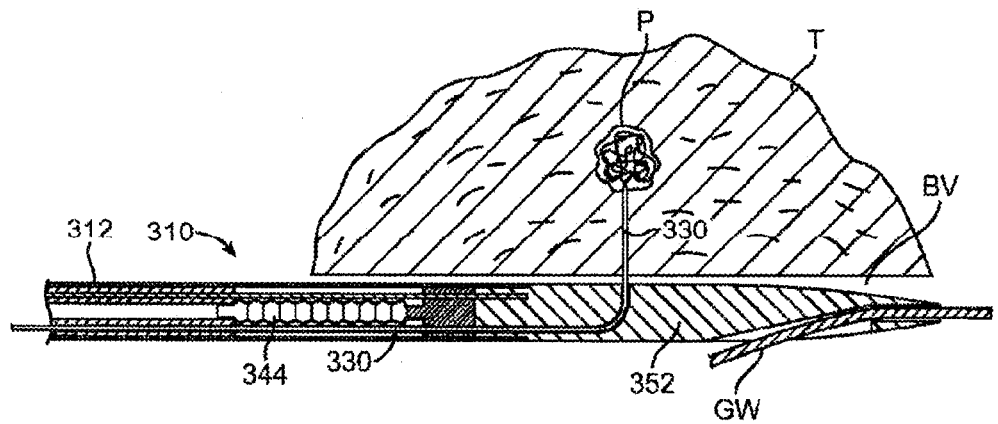
FIG. 8 is a cross-sectional view similar to FIG. 7, shown with the injection needle laterally advanced into luminal tissue for the delivery of therapeutic or diagnostic agents according to the present invention.

As can be seen in FIG. 8, the catheter 310 may be positioned in a blood vessel BV, over a guide wire GW in a conventional manner. Distal advancement of the piston 338 causes the needle 330 to advance into tissue T surrounding the lumen adjacent to the catheter when it is present in the blood vessel. The therapeutic or diagnostic agents may then be introduced through the port 326 using syringe 328 in order to introduce a plume P of agent in the cardiac tissue, as illustrated in FIG. 8. The plume P will be within or adjacent to the region of tissue damage as described above.

The needle 330 may extend the entire length of the catheter body 312 or, more usually, will extend only partially into the therapeutic or diagnostic agents delivery lumen 337 in the tube 340. A proximal end of the needle can form a sliding seal with the lumen 337 to permit pressurized delivery of the agent through the needle.

The needle 330 will be composed of an elastic material, typically an elastic or super elastic metal, typically being nitinol or other super elastic metal. Alternatively, the needle 330 could be formed from a non-elastically deformable or malleable metal which is shaped as it passes through a deflection path. The use of non-elastically deformable metals, however, is less preferred since such metals will generally not retain their straightened configuration after they pass through the deflection path.

The bellows structure 344 may be made by depositing by parylene or another conformal polymer layer onto a mandrel and then dissolving the mandrel from within the polymer shell structure. Alternatively, the bellows 344 could be made from an elastomeric material to form a balloon structure. In a still further alternative, a spring structure can be utilized in, on, or over the bellows in order to drive the bellows to a closed position in the absence of pressurized hydraulic fluid therein.

After the therapeutic material is delivered through the needle 330, as shown in FIG. 8, the needle is retracted and the catheter either repositioned for further agent delivery or withdrawn. In some embodiments, the needle will be retracted simply by aspirating the hydraulic fluid from the bellows 344. In other embodiments, needle retraction may be assisted by a return spring, e.g., locked between a distal face of the piston 338 and a proximal wall of the distal tip 352 (not shown) and/or by a pull wire attached to the piston and running through lumen 341.

Figure 9:
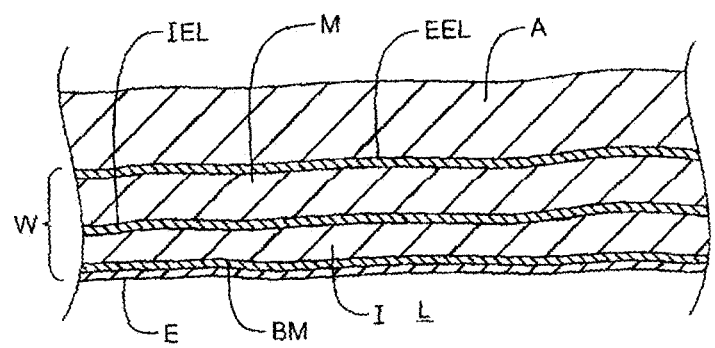
FIG. 9 is a schematic illustration of an artery together with surrounding tissue illustrating the relationship between the perivascular tissue, the adventitia, and the blood vessel wall components.

The perivascular space is the potential space over the outer surface of a "vascular wall" of either an artery or vein. Referring to FIG. 9, a typical arterial wall is shown in cross-section where the endothelium E is the layer of the wall which is exposed to the blood vessel lumen L. Underlying the endothelium is the basement membrane BM which in turn is surrounded by the intima I. The intima, in turn, is surrounded by the internal elastic lamina IEL over which is located the media M. In turn, the media is covered by the external elastic lamina (EEL) which acts as the outer barrier separating the arterial wall, shown collectively as W, from the adventitial layer A. Usually, the perivascular space will be considered anything lying beyond the external elastic lamina EEL, including regions within the adventitia and beyond.

Figure 10A:
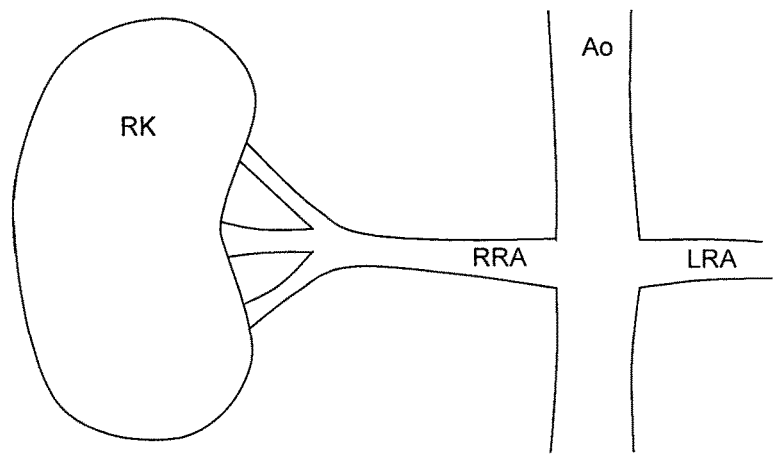
FIG. 10A is a schematic illustration of the kidney and arterial structure that brings blood to the kidney.
Figure 10B:
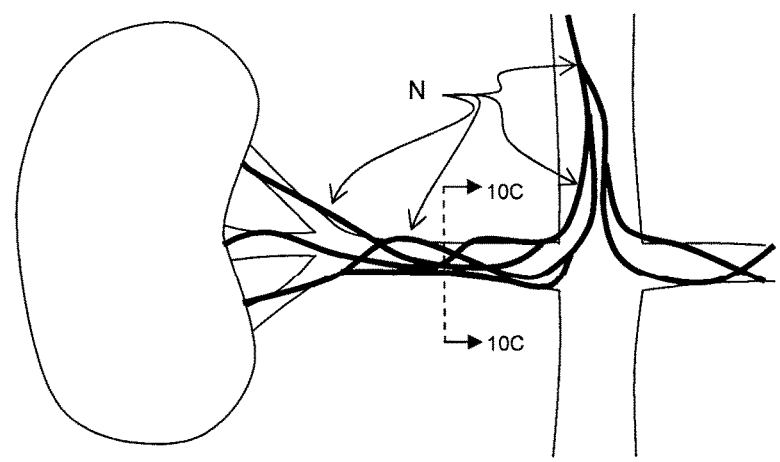
FIG. 10B is a schematic illustration of FIG. 10A with sympathetic nerves shown leading from the nerve plexi or ganglia proximate to the aorta around the renal artery and terminating in the kidney.
Figure 10C:
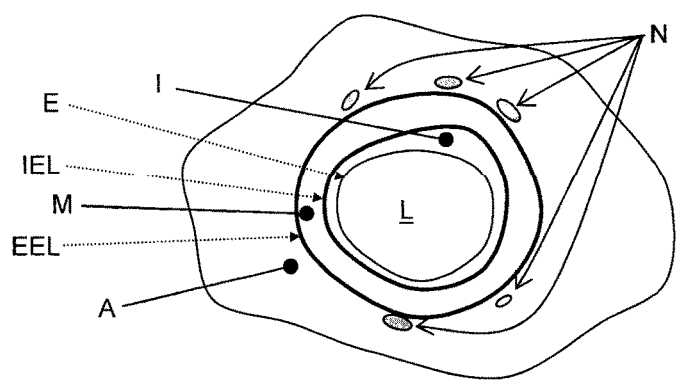
FIG. 10C is a cross-sectional view along line 10C-10C of FIG. 10B.

Turning now to FIG. 10A-C, the renal arterial location and structure are shown. In FIG. 10A, the aorta (Ao) is shown as the central artery of the body, with the right renal artery (RRA) and left renal artery (LRA) branching from the aorta to lead blood into the kidneys. For example, the right renal artery leads oxygenated blood into the right kidney (RK). In FIG. 10B, the nerves (N) that lead from the aorta to the kidney are displayed. The nerves are shown to surround the renal artery, running roughly parallel but along a somewhat tortuous and branching route from the aorta to the kidney. The cross-section along line 10C-10C of FIG. 10B is then shown in FIG. 10C. As seen in this cross-sectional representation of a renal artery, the nerves (N) that lead from aorta to kidney run through the arterial adventitia (A) and in close proximity but outside the external elastic lamina (EEL). The entire arterial cross section is shown in this FIG. 10C, with the lumen (L) surrounded by, from inside to outside, the endothelium (E), the intima (I), the internal elastic lamina (IEL), the media (M), the external elastic lamina (EEL), and finally the adventitia (A).

Figure 11A:
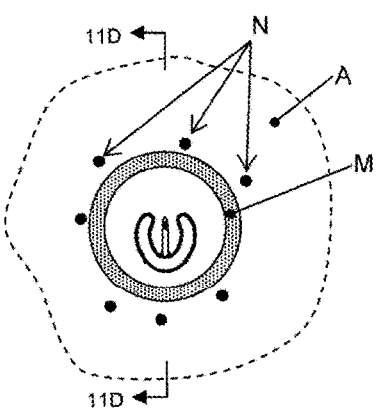
FIGS. 11A-11C are cross-sectional views similar to FIGS. 4A and 4D, shown with the injection needle advanced into the adventitia for progressive delivery of agents to sympathetic nerves according to the present invention.
Figure 11D:
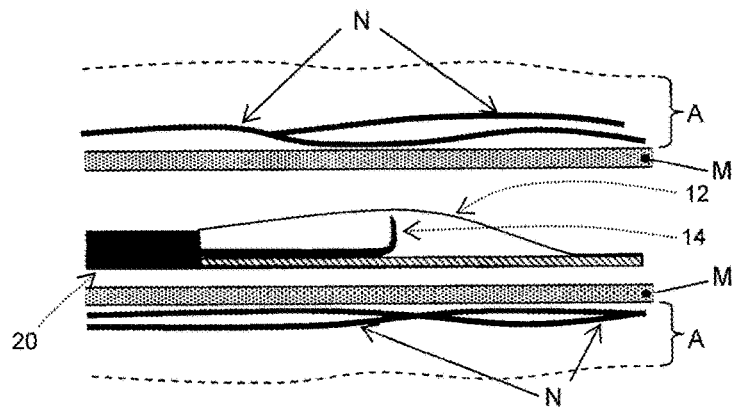
FIG. 11D is a cross-sectional view along line 11D-11D of FIG. 11A.

As illustrated in FIG. 11A-F, the methods of the present invention may be used to place an injection or infusion catheter similar to those illustrated by FIGS. 1-5 into a vessel as illustrated in FIG. 10C and to inject a plume (P) of neuromodulating agent into the adventitia (A) such that the agent comes in contact with the nerves (N) that innervate the adventitia of the renal artery. As can be seen in FIG. 11A, a catheter in the same state as FIG. 4A, wherein an actuator is shielding a needle so that the actuator can be navigated through the vessels of the body without scraping the needle against the vessel walls and causing injury, is inserted into an artery that has a media (M), an adventitia (A), and nerves (N) within the adventitia and just outside the media. A cross-section along line 11D-11D from FIG. 11A is shown in FIG. 11D. It can be seen from this cross section that a therapeutic instrument comprised similarly to those in FIGS. 1-3, with an actuator (12) attached to a catheter (20) and a needle (14) disposed within the actuator.

Figure 11B:
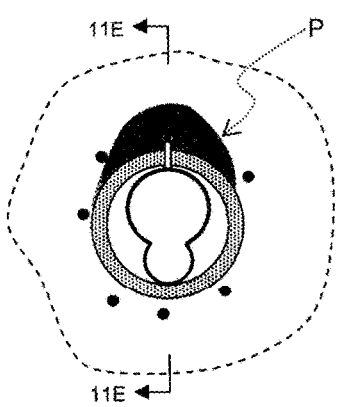
Figure 11E:
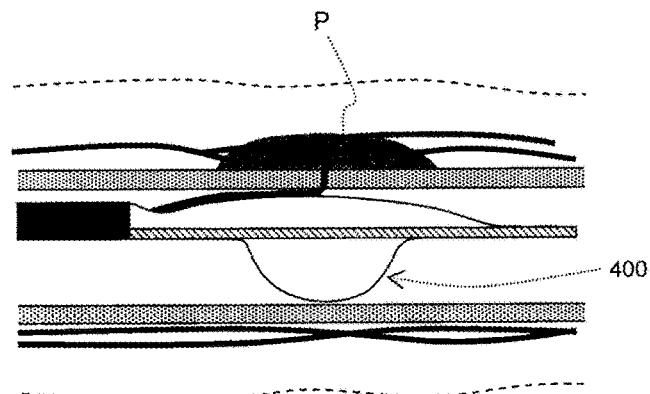
FIG. 11E is a cross-sectional view along line 11E-11E of FIG. 11B.

Turning to FIGS. 11B and 11E, we see the same system as that in FIGS. 11A and 11D, again where FIG. 11E is a view of the cross-section along line 11E-11E from FIG. 11B. In FIGS. 11B and 11E, however, the actuator that has been filled with a fluid, causing the actuator to unfurl and expand, and the needle aperture to penetrate the media and into the adventitia where nerves are located. After the needle penetrates to the adventitia, a plume (P) that consists of either diagnostic agent such as radio-opaque contrast medium or neuromodulating agent such as guanethidine or a combination of the diagnostic and therapeutic agents is delivered beyond the EEL and into the adventitia. The plume (P) begins to migrate circumferentially and longitudinally within the adventitia and begins to come into contact with the nerve fibers that run through the adventitia. At this point, the physician may begin to notice the therapeutic effects. Usually, the plume P that is used to diagnose the presence of the injection and the location of the injection is in the range from 10 to 100 µl, more often around 50 µl. The plume will usually indicate one of four outcomes: (1) that the needle has penetrated into the adventitia and the plume begins to diffuse in a smooth pattern around and along the outside of the vessel, (2) that the plume follows the track of a sidebranch artery, in which case the needle aperture has been located into the sidebranch rather than in the adventitia, (3) that the plume follows the track of the artery in which the catheter is located, indicating that the needle has not penetrated the vessel wall and fluid is escaping back into the main vessel lumen, or (4) that a tightly constricted plume is forming and not diffusing longitudinally or cyndrically around the vessel, indicating that the needle aperture is located inward from the EEL and inside the media or intima. The plume is therefore useful to the operating physician to determine the appropriateness of continued injection versus deflation and repositioning of the actuator at a new treatment site.

Figure 11C:
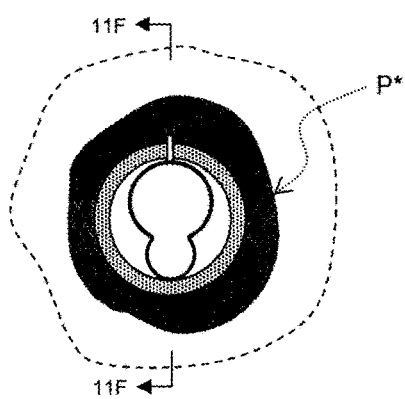
Figure 11F:
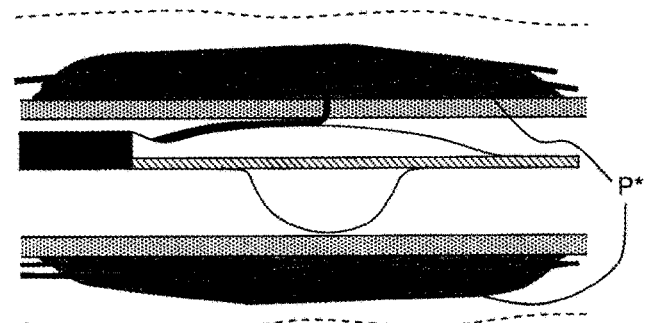
FIG. 11F is a cross-sectional view along line 11F-11F of FIG. 11C.

In FIGS. 11C and 11F, where FIG. 11F is a cross-sectional view across the line 11F-11F from FIG. 11C, one can see that after the plume is used to diagnose the appropriate tissue location of injection, further injection can be performed to surround the vessel with the neuromodulating agent. The extent of the final plume P* is usually fully circumferential around the artery and usually travels longitudinally by at least 1 cm when the injection volume is between 300 µl and 3 mL. In many cases, less than these volumes may be required in order to observe a therapeutic benefit to the patient's hypertension. In some embodiments, more or less than this volume is used to achieve the final therapeutic benefit desired. In some embodiments the total amount of neuromodulating agent per artery is from 2 µg to 750 mg. In some embodiments the total amount of neuromodulating agent per artery is from 10 µg to 500 mg. In some embodiments the total amount of neuromodulating agent per artery is from 10 µg to 200 mg. In some embodiments the total amount of neuromodulating agent per artery is from 100 µg to 200 mg. In some embodiments the total amount of neuromodulating agent per artery is from 500 µg to 200 mg. In some embodiments the total amount of neuromodulating agent per artery is from 500 µg to 200 mg. In some embodiments the total amount of neuromodulating agent per artery is from 1 mg to 200 mg. In some embodiments the total amount of neuromodulating agent per artery is from 1 mg to 100 mg. In some embodiments the total amount of neuromodulating agent per artery is from about 10 mg to about 100 mg. In some embodiments the total amount of neuromodulating agent per artery is from about 20 mg to about 80 mg. In some embodiments the total amount of neuromodulating agent per artery is from about 40 mg to about 80 mg. In some embodiments the total amount of neuromodulating agent per artery is from about 45 mg to about 75 mg. In some embodiments the total amount of neuromodulating agent per artery is from about 50 mg to about 60 mg. As used herein, the term "about" when used in reference to the total amount of agent delivered means variations of +/−5%, +/−10%, +/−15%, +/−25%, +/−50%, +/−0.5 µg, +/−1 µg, +/−10 µg, +/−50 µg, +/−1 mg, +/−3 mg, or +/−5 mg, depending on the amount delivered.

In some embodiments from about 2 mL to about 8 mL of a solution of neuromodulating agent, such as guanethidine, is delivered per artery at a concentration of from about 5 mg/mL to about 15 mg/mL. At this point, the neuromodulating agent has penetrated the nerves around the entire artery, blocking the transmission of nerve signals and thereby creating chemical, neuromodulating, or biological denervation. As used herein, the term "about" when used in reference to the total volume of agent delivered means variations of +/−5%, +/−10%, +/−15%, +/−25%, +/−50%, +/−0.5 mL, +/−1 mL, or +/−2 mL. As used herein, the term "about" when used in reference to the concentration of agent delivered means variations of +/−1%, +/−5%, +/−10%, +/−15%, +/−25%, or +/−50%.

Figure 16:
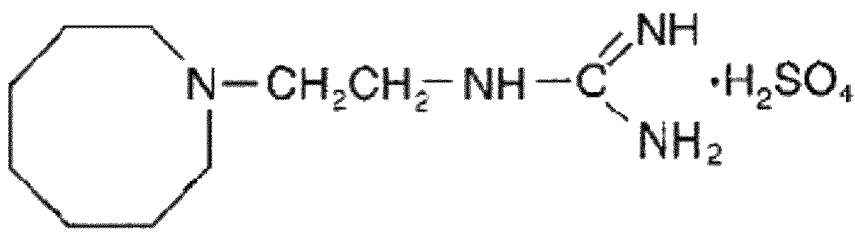
FIG. 16 depicts the chemical structure of Guanethidine Sulfate.

Provided herein are compositions, methods, devices, and systems that generate this effect by local administration of the pharmaceutical agent guanethidine monosulfate which is also known as 2-(Octahydro-1-azocinyl)ethyl guanidine sulphate; Heptamethylenimine, 1-(2-guanidinoethyl)-; N-(2-Perhydroazocin-1-ylethyl)guanidine; Azocine, 1-((2-(aminoiminomethyl)amino)ethyl)octahydro-; (2-(Hexahydro-(2H)-azocin-1-yl)ethyl)guanidinium sulphate; Azocine, 1-(2-guanidinoethyl)octahydro-; Guanidine, [2-(hexahydro-1(2H)-azocinyl)-ethyl]-, sulfate (1:1); 2-[2-(azocan-1-yl)ethyl]guanidine; Abapresin; Oktadin; Dopom; N-(2-Guanidino ethyl)heptamethylenimine sulfate; Eutensol; Esimil; Dopam; 2-(1-N,N-Heptamethyleneimino)ethylguanidine; Guanidine, (2-(hexahydro-1(2H)-azocinyl)ethyl)-, sulfate (1:1); Guanethidinum [INN-Latin]; Oktatenzin; Oktatensin; Ismelin™; Guanidine, (2-(hexahydro-1(2H)-azocinyl) ethyl)-; Guanetidina [INN-Spanish]; Octatensine; (2-(Hexahydro-1(2H)-azocinyl)ethyl) guanidine hydrogen sulfate; Sanotensin; 2-[2-(azocan-1-yl)ethyl]guanidine; sulfuric acid; 2-(1-Azacyclooctyl)ethylguanidine; Ismelin sulfate; Guanethidine sulfate; (2-(Octahydro-1-azocinyl)ethyl) guanidine; Ismelin; or (2-(Hexahydro-1(2H)-azocinyl)ethyl) guanidine sulfate (1:1), with the chemical formula $C_{10}H_{22}N_4 \cdot H_2O_4S$ and molecular structure displayed in FIG. 16. Provided herein are compositions, methods, devices, and systems that generate this effect by local administration of the pharmaceutical agent guanethidine hemisulfate.

The present invention relates generally to pharmaceutical preparations, systems including medical devices and diagnostic or therapeutic agents, and methods to treat disease. More particularly, an embodiment of the present invention relates to modification of local tissue environment to modulate the therapeutic index of locally or systemically delivered therapeutic or diagnostic agents. Even more particularly, an embodiment of the present invention relates to improved ability to reduce sympathetic nerve activity in the adventitia and perivascular tissues around arteries and veins in the body.

A particular aspect of the present invention is the ability to modulate the local tissue environment around a renal artery to enable more effective denervation with pharmaceutical agents in order to treat hypertension, heart failure, sleep apnea, insulin resistance, or inflammation.

Provided herein are methods, systems and compositions for the practice of inventions described in U.S. patent application Ser. Nos. 12/765,708 and 12/765,720, the full disclosures of which are incorporated by reference.

A method for improving pharmaceutical therapy is presented herein. In general, embodiments of the methods include improvements in drug therapeutic index with the modulation of physiologic tissue conditions. In particular, embodiments of the methods comprise modulation of pH in local tissues with local drug or buffer delivery in order to enhance the therapeutic index of agents delivered into tissues or in order to have direct therapeutic effect by virtue of modulating tissue pH locally. This effect may be based upon the ability for agents to cross cell membranes more effectively at a higher or lower pH depending on the protonation of the agent's molecular structure and the cell's increased or decreased affinity for the protonated or unprotonated moiety.

Provided herein are methods including specific improvements to guanethidine neurodegeneration in conditions of elevated pH and the methods with which to create such conditions. These methods are particularly useful in the degeneration of the renal nerves located in the adventitia and perivascular tissue surrounding the renal arteries. These nerves are seminal to the initiation and maintenance of the hypertensive state and the denervation of the renal arteries has shown beneficial effect with respect to reductions in blood pressure, improvements in heart failure, reductions in insulin resistance and sleep apnea, and even speculated improvements in vascular inflammatory diseases.

Guanethidine in vitro studies have described cell culture conditions by which guanethidine monosulfate has been cytotoxic to harvested and cultured rat superior cervical ganglia neurons. (Johnson E M and Aloe L. *Suppression of the in vitro and in vivo cytotoxic effects of guanethidine in sympathetic neurons by nerve growth factor*, Brain Research 1974; 81:519-532; Wakshull E, Johnson M I, Burton H. *Persistence of an amine uptake system in cultured rat sympathetic neurons which use acetylcholine as their transmitter*, J. Cell Biology 1978; 79:121-131). The experiments by Johnson, Wakshull and others found that guanethidine has weak cytotoxic activity at pH of 7.0 to 7.2 and strong cytotoxic activity at pH of 8.0 when exposed to 100 µM concentrations of guanethidine for 40 to 48 hours.

In-vivo testing of guanethidine's neuronal cytotoxicity has shown that perivascular injection of guanethidine hemisulfate in concentrations of 8.3 mg/mL and pH of 8.5 to 9.5 produces a renal denervation in pigs, while perivascular injection of 8.3 mg/mL guanethidine monosulfate at pH of 5.5 to 6.5 does not produce the same denervation.

With injection into the perivascular and adventitial space, injectable agents are tracked by the methods described in U.S. Pat. No. 7,744,584, incorporated herein by reference, and agents are preferably injected by catheters similar to those described in U.S. Pat. No. 7,691,080, incorporated herein by reference. It is recognized, however, that other catheters or needles could be used to inject agents locally within tissues to accomplish similar effects to those described herein.

Provided herein are compositions, devices, systems, and methods that locally modulate of physiologic pH by injection or other means (it is known, for example, that in the presence of electrical signals or certain metallic substances, for example, local pH can be modulated). In some embodiments, the method comprises injecting a composition that exists at pH around 9 into the tissues surrounding nerves that are the target of denervation, during, before, or after the delivery of the therapeutic agent guanethidine monosulfate. The injection or infusion of this composition into the tissue surrounding renal arteries (see FIG. 11 below) displaces interstitial fluids that have neutral physiologic pH of around 7.3 to 7.4.

Other methods of the current invention involve the modulation of local tonicity or osmolarity to achieve enhanced cellular uptake of pharmaceutical agents in formulation with or delivered before or after the agents that modulate local tonicity or osmolarity. For example, delivery of a hypertonic saline causes, through osmosis, the release of liquid by cells. Similarly, delivery of hypotonic solutions can cause cells to swell while they take up additional liquid from their surroundings. Agents instilled into the interestium around cells can potentially have improved uptake depending on the local tissue tonicity. This behavior varies from one therapeutic agent to the next, due to ability for agents to bind membrane receptor proteins or enter cells through channels or pores.

Additional methods of the current invention do not involve application of therapeutic agents in concert with local modification of tissue physiology, but rely directly on the local modulation to accomplish therapeutic goals. For example, hypertonic saline, detergents, solvents such as ethanol, strong acids and strong bases can each lead to cell damage, alteration or destruction with the local modulation of physiology. The delivery of these agents by the methods described in this invention are also useful for accomplishing goals set out here such as localized nerve destruction. Modulation of pH in solutions can be accomplished with alkaline or acidic buffer agents. Buffer agents include but are not limited to sodium hydroxide, sodium bicarbonate, magnesium hydroxide, sulfuric acid, hydrochloric acid, citric acid, acetic acid, sodium citrate, sodium acetate, boric acid, potassium dihydrogen phosphate, diethyl barbituric acid, 3-{[tris(hydroxymethyl)methyl]amino}propanesulfonic acid, N,N-bis(2-hydroxyethyl)glycine, tris(hydroxymethyl) aminomethane, N-tris(hydroxymethyl)methylglycine, 2-[Bis(2-hydroxyethyl)amino]-2-(hydroxymethyl)-1,3-propanediol, 3-[N-Tris(hydroxymethyl)methylamino]-2-hydroxypropanesulfonic acid, 4-2-hydroxyethyl-1-piperazineethanesulfonic acid, 2-{[tris(hydroxymethyl)methyl]amino}ethanesulfonic acid, 3-(N-morpholino) propanesulfonic acid, piperazine-N,N'-bis(2-ethanesulfonic acid), dimethylarsinic acid, saline sodium citrate, 2-(N-morpholino)ethanesulfonic acid, or glycine.

In yet another aspect to this invention, a novel composition is described. In improving the performance of guanethidine in local tissue delivery, a pH adjustment may be required. Compositions of the present invention include the formulation of guanethidine in concentrations ranging from 1 µg/mL to 50 mg/mL at pH of greater than 7. In particular aspects of this invention, concentration of a formulation is between 1 and 30 mg/mL, sodium chloride content is between 0.7% and 0.9%, though greater or lesser concentrations may also be used, and pH is adjusted to about 9.5 but at least between 8 and 11 by buffering with an alkaline buffer such as sodium hydroxide or other buffers described above, until the desirable pH is reached and can be maintained over time.

In addition to the agents described in U.S. patent application Ser. No. 10/765,720, additional agents are useful when delivered with the methods presented in Ser. No. 10/765,720 as well as in this invention. These agents include toxins entering cells through sodium channels, including tetrodotoxin and batrachotoxin, toxins entering cells through potassium channels, including maurotoxin, agitoxin, charybdotoxin, margatoxin, slotoxin, syellatoxin and hefutoxin, and toxins entering cells through calcium channels, including calciseptine, taicatoxin, calcicludine and PhTx3.

Other agents that benefit from the methods described here and in referenced patent applications include adrenergic blockers and stimulators (e.g., doxazosin, guanadrel, guanethidine, pheoxybenzamine, prazosin plus polythiazide, terazosin, methyldopa, clonidine, guanabenz, guanfacine); Alpha-/beta-adrenergic blockers (e.g., Labetalol); angiotensin converting enzyme (ACE) inhibitors (e.g., benazepril, catopril, enalapril, enalaprilat, fosinopril, lisinopril, moexipril, quinapril, ramipril, and combinations with calcium channel blockers and diuretics; ACE-receptor antagonists (e.g., losartan); Beta blockers (e.g., acebutolol, atenolol, betaxolol, bisoprolol, carteolol, esmolol, fimolol, pindolol, propranolol, penbatolol, metoprolol, nadolol, sotalol); Calcium channel blockers (e.g., Amiloride, amlodipine, bepridil, diltiazem, isradipine, nifedipine, verapamil, felodipine, nicardipine, nimodipine); Antiarrythmics, groups I-IV (e.g., bretylium, disopyramide, encamide, flecamide, lidocaine, mexiletine, moricizine, propafenone, procainamide, quinidine, tocamide, esmolol, propranolol, acebutolol, amiodarone, sotalol, verapamil, diltiazem, pindolol, bupranolol hydrochloride, trichlormethiazide, furosemide, prazosin hydrochloride, metoprolol tartrate, carteolol hydrochloride, oxprenolol hydrochloride, and propranolol hydrochloride); and miscellaneous antiarrythmics and cardiotonics (e.g., adenosine, digoxin; metildigoxin, caffeine, dopamine hydrochloride, dobutamine hydrochloride, octopamine hydrochloride, diprophylline, ubidecarenon, digitalis), and sensory denervation agents including capsaicin.

Other agents have been shown to create partial or complete sympathectomy as well, and may be used as the therapeutic agent as described herein. These include an immunosympathectomy agent such as anti-nerve growth factor (anti-NGF); auto-immune sympathectomy agents such as anti-dopamine beta-hydroxylase (anti-D.beta.H) and anti-acetylcholinesterase (anti-AChe); chemical sympathectomy agents such as 6-hydroxyldopamine (6-OHDA), bretylium tosylate, guanacline, and N-(2-chloroethyl)-N-ethyl-2-bromobenzylamine (DSP4); and immunotoxin sympathectomy agents such as OX7-SAP, 192-SAP, anti-dopamine beta-hydroxylase saporin (DBH-SAP), and anti-dopamine beta-hydroxylase immunotoxin (DHIT). A full description of these agents is found in Picklo M J, J Autonom Nery Sys 1997; 62:111-125. Phenol and ethanol have also been used to produce chemical sympathectomy and are also useful in the methods of this invention. Other sympatholytic agents include alpha-2-agonists such as clonidine, guanfacine, methyldopa, guanidine derivatives like betanidine, guanethidine, guanoxan, debrisoquine, guanoclor, guanazodine, guanoxabenz and the like; imadazoline receptor agonists such as moxonidine, relmenidine and the like; ganglion-blocking or nicotinic antagonists such as mecamylamine, trimethaphan and the like; MAOI inhibitors such as pargyline and the like; adrenergic uptake inhibitors such as rescinnamine, reserpine and the like; tyrosine hydroxylase inhibitors such as metirosine and the like; alpha-1 blockers such as prazosin, indoramin, trimazosin, doxazosin, urapidil and the like; non-selective alpha blockers such as phentolamine and the like; serotonin antagonists such as ketanserin and the like; and endothelin antagonists such as bosentan, ambrisentan, sitaxentan, and the like.

Additionally, agents that sclerose nerves can be used to create neurolysis or sympatholysis. Sclerosing agents that lead to the perivascular lesioning of nerves include quinacrine, chloroquine, sodium tetradecyl sulfate, ethanolamine oleate, sodium morrhuate, polidocanol, phenol, ethanol, or hypertonic solutions.

In FIG. 12, a catheter that can be used to accomplish the methods of this invention is displayed. On the right side of FIG. 12, the catheter is shown in photographs in its sheathed configuration (top) with a microneedle held within a sheathing envelope of the catheter. The catheter is introduced into the artery while deflated and the needle is sheathed within a balloon. The balloon walls sheath the needle (microneedle) and protect the artery wall during introduction or removal of the device. When the catheter balloon is inflated, the microneedle is pushed out from the sheathing envelope and can be deployed through a vessel wall, as is shown on the left side of FIG. 12 in cross-section. The figures on the left side in FIG. 12 show the cross sectional balloon profile as it sheaths the needle (top left) and during inflation to push the needle into the artery wall (bottom left). The needle is extruded outward when the balloon is inflated, generally perpendicular to the long axis of the catheter (i.e. generally perpendicular to the axis along the catheter's length). The image on the right side of FIG. 12 (bottom) shows the expanded catheter, with the needle deployed and a backing balloon that provides an opposing force to slide the needle into the wall (for example, a bronchial or other lumen wall, such as an artery wall). In the case of denervation, particularly renal denervation, the ideal location for delivery of therapeutic agents is beyond the external elastic lamina, since the renal nerves lie within the adventitia and perivascular tissue.

Figure 13:
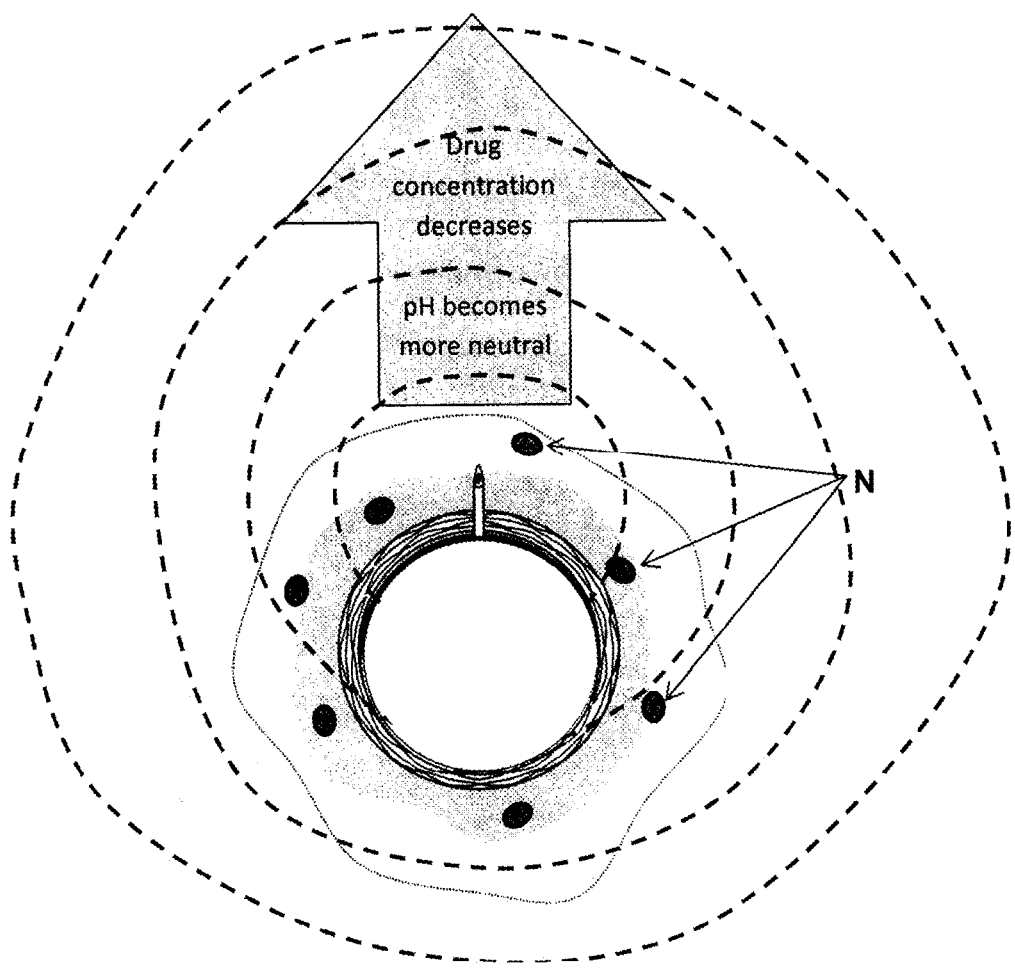
FIG. 13 depicts a cross-section of a vessel having an embodiment catheter deployed through a lumen or vessel wall and shows an agent delivery into tissue and shows that in some embodiments the drug concentration decreases and the pH of the agent delivered becomes more neutral as the distance from the agent delivery location increases.

Moving now to FIG. 13, a similar cross-section of vessel is seen as in FIGS. 11 and 12. A microneedle such as that described above is deployed through the wall of a vessel such as a renal artery or renal vein. Of course, the renal artery or vein adventitia and perivascular space could be reached via other percutaneous means, but not as precisely as with a catheter as described herein. Regardless of how the adventitia and perivascular tissues are accessed, a therapeutic agent may be delivered in concert with, before or after the delivery of a medium that affects the local tissue physiology. A particular embodiment of the methods described here involves the injection of a high-pH solution, with pH in the range of 8 to 10, or with pH in the range of 7 to 13, or with a pH of about 8 to about 10, or with a pH of about 8.5 to about 9.5, or with a pH of about 8.3, or with a pH of about 9.3, into the perivascular space along with the denervating agent, guanethidine. Guanethidine is preferably delivered in aqueous form as its salt, guanethidine monosulfate. In some embodiments, the guanethidine is delivered in aqueous form as guanethidine hemisulfate. The composition delivered in this embodiment preferably contains approximately 10 mg/mL guanethidine monosulfate, but may contain within the range of 1 mg/mL and 30 mg/mL, or even within the range of 1 μg/mL to 50 mg/mL. The composition further contains sodium chloride preferably in the range of 0.7% to 0.9%, but could contain anywhere from 0% to 3% sodium chloride. Furthermore, the composition preferably has a pH of 8 to 10, or any of the other pH ranges noted herein above about the pH of 7, and may also contain a radio-opaque contrast medium such as Omnipaque, Visipaque, or Isovue (though other well-known contrast agents could also be used in the composition). As used herein, the term "about" when referring to a pH means +/−0.5 pH, +/−0.3 pH, +/−0.2 pH, or +/−0.1 pH.

Figure 14:
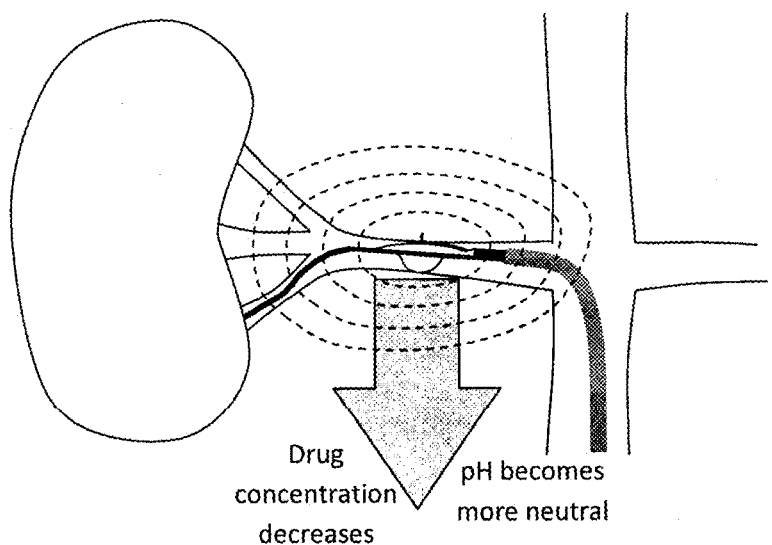
FIG. 14 depicts another embodiment view of how drug concentration may decrease and pH may become more neutral as the distance from the point of agent delivery increases, similar to that depicted in cross-section in FIG. 13.

In FIGS. 13 and 14, the dashed lines represent consistent levels of drug concentration or consistent levels of tissue pH. As an agent is delivered in tissue, the concentration of the agent decreases from the point at which it is being delivered to a point far from the delivery location. Thus, the concentration is higher at the infusion site and lower at a point several centimeters from the infusion site, for example if several milliliters are being infused. Similarly, in the case that an alkaline composition is delivered through the needle, the local tissue pH is higher at the infusion site and drops toward a neutral pH of 7.0 to 7.3 in more distant tissue. The dashed lines in FIGS. 13 and 14 can also represent a consistent tissue pH, with the lines further from the injection site nearing neutrality and the lines closer to the injection site representing elevated pH.

Figure 15:
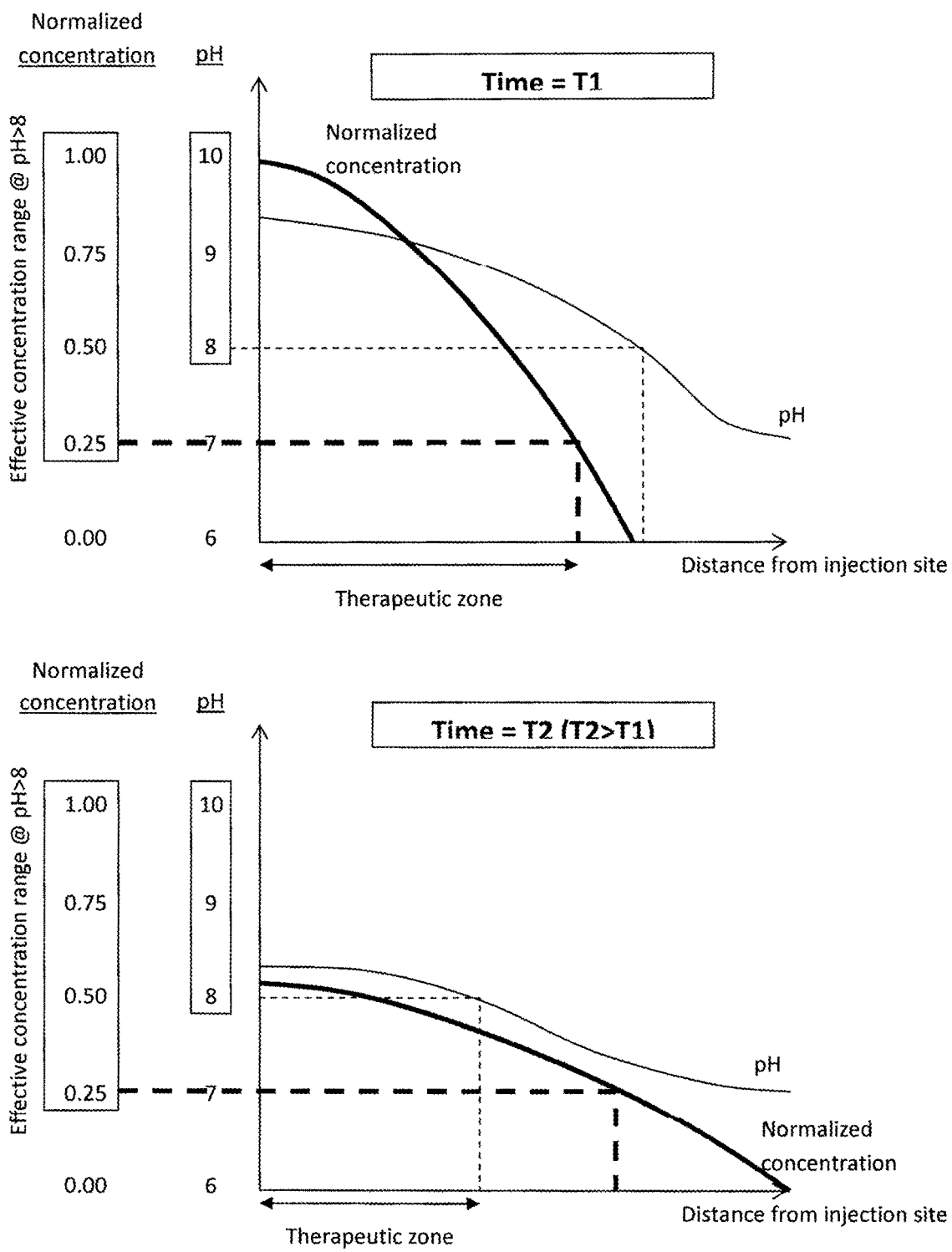
FIG. 15 is a series of two plots at two times: time 1 (T1) in the top plot, and time 2 (after time 1) in the bottom plot (T2) showing the normalized concentration and the pH as the distance from the injection site increases along the x-axis, wherein the pH and the concentration are both depicted on the y-axis, and depicting a therapeutic zone that exists where the concentration is at least 0.25 of some maximal normalized concentration and a pH of at least 8.

Turning now to FIG. 15, a series of two plots are displayed at times T1 and T2, where T2 is some time greater than T1. At time T1 following injection of the therapeutic agent at a normalized concentration of 1.0 (for example, 100 μg/mL) and pH of 10, the agent concentration declines toward zero with distance from the injection site and the pH of the local tissue declines toward neutral pH with distance from the injection site. For the purposes of illustration, an effective concentration of at least 0.25 (for example, 25 μg/mL) in an area of tissue that has pH greater than 8 defines the therapeutic zone. As can be seen in the illustration plots of FIG. 15, this therapeutic zone changes with time, since the local concentration drops and the distant concentration rises as drug distributes away from the injection site; while pH slowly approaches neutral pH as physiologic drainage and replacement of interstitial fluids neutralizes the tissue. As an example, in the case of guanethidine, a concentration of 20-30 μg/mL at pH 8 is effective in destroying nerves, but at pH 7, nerves are maintained even at concentrations of 100 μg/mL. This is most likely due to an enhanced ability for guanethidine to enter nerves when it is unprotonated as compared to its protonated state. Thus, nerves in the therapeutic zone (where guanethidine is in an alkaline environment and is more likely to be unprotonated or singly protonated) are destroyed while nerves outside of the therapeutic zone (where guanethidine is in a more neutral environment and is more likely to be singly or doubly pronated) are maintained. Furthermore, other tissues in the therapeutic zone are not sacrificed, since guanethidine specifically targets nerves and the pH is not great enough to cause caustic effects to the other tissues.

Provided herein is a method for enhancing the uptake of therapeutic agents into tissue comprising modulating pH of the tissue by creating a zone of the tissue having a center and an outer edge, wherein the zone comprises a modulated pH as compared to a pre-modulation pH of the tissue prior to modulation or as compared to a neutral pH, wherein zone comprises a gradient of pH that is most modulated at the center of the zone and reduces to the pre-modulation pH of the tissue or to neutral pH at the outer edge of the zone, and wherein enhanced uptake of a therapeutic agent occurs in the zone as compared to uptake that would occur into tissue at the pre-modulation pH or at neutral pH. In some embodiments, the zone comprises a therapeutic zone. In some embodiments a portion of the zone is the therapeutic zone as shown in FIG. 15. Such a method is depicted in FIGS. 13-15, as described herein.

Provided herein is a method for enhancing the uptake of therapeutic agents into tissue comprising—modulating pH of the tissue by creating a zone of the tissue having a center and an outer edge, and—delivering a therapeutic agent into the zone; wherein the zone comprises a modulated pH as compared to a pre-modulation pH of the tissue prior to modulation or as compared to a neutral pH, wherein zone comprises a gradient of pH that is most modulated at the center of the zone and reduces to the pre-modulation pH of the tissue or to neutral pH at the outer edge of the zone, wherein enhanced uptake of the therapeutic agent occurs in the zone as compared to uptake that would occur into tissue at the pre-modulation pH or at neutral pH. In some embodiments, the zone comprises a therapeutic zone. In some embodiments a portion of the zone is the therapeutic zone as shown in FIG. 15. Such a method is depicted in FIGS. 13-15, as described herein.

In some embodiments, the method comprises delivering the therapeutic agent into the zone. In some embodiments, the therapeutic agent is delivered systemically and modulating the tissue pH enhances a buildup of the therapeutic agent in the zone or improves a therapeutic index in the zone.

In some embodiments, the enhanced uptake occurs within a portion of the zone having the modulated pH that is modulated from the pre-modulation pH by a preselected amount. In some embodiments, the enhanced uptake occurs within a portion of the zone having the modulated pH that is modulated from a neutral pH by a preselected amount. In some embodiments, the portion of the zone is the therapeutic zone, as shown in FIG. 15 and descriptions thereof. In some embodiments, the preselected amount is a difference of pH between the modulated pH and the pre-modulation pH or between the modulated pH and the neutral pH of one or more of: 0.5, 1.0, 1.5, 2.0, 2.5, 3.0, 3.5, 4.0, 4.5, −0.5, −1.0, −1.5, −2.0, −2.5, −3.0, −3.5, −4.0, −4.5, from 0.5 to 5.0, from 1.5 to 4.5, from 2.0 to 4.0, about 0.5, from −0.5 to −5.0, from −1.5 to −4.5, from −2.0 to −4.0, about 0.5, about 1.0, about 1.5, about 2.0, about 2.5, about 3.0, about 3.5, about 4.0, about 4.5, about −0.5, about −1.0, about −1.5, about −2.0, about −2.5, about −3.0, about −3.5, about −4.0, and about −4.5. In some embodiments, the modulated pH is a pH that is lower than the tissue outside the zone that is higher than the tissue outside the zone, that is lower than the pH of the tissue prior to modulation, or that is higher than the pH of the tissue prior to modulation. In some embodiments, the modulated pH is more acidic than the pH of tissue outside the zone, or is more alkaline than the pH of tissue outside the zone. The method of Claim 42, wherein the modulated pH at least 7, at most 11, at least 7 and at most 11, at least 8 and at most 10, or a predetermined pH that is effective to denervate nerves to which such therapeutic agent is delivered. In some embodiments, the therapeutic agent comprises guanethidine. In some embodiments, the guanethidine includes monosulfate or hemisulfate. In some embodiments, the modulated pH at least 7, at most 11, at least 7 and at most 11, at least 8 and at most 10, or a predetermined pH that is effective to denervate nerves to which such therapeutic agent is delivered.

Another point of the preceding paragraph illustrates an important aspect of this invention: that by modulating the local physiology (pH) and delivering a therapeutic agent (guanethidine), a specific effect can be localized to the borders to which the tissue modulation and drug concentration are effective. As is the case with guanethidine denervation of renal arteries for the treatment of hypertension, it is desirable to create a localized and focused denervation of the nerves that surround the renal artery, without affecting distant nerves such as those leading to the mesenteric, hepatic, or other systems in the body. This remains true even though the drug eventually distributes through the bloodstream and urinary system, reaching distant tissues, because the drug does not cause permanent nerve destruction at physiologic pH. Thus, with the novel compositions and novel methods described here, permanent effects can be focused to the local tissue of interest without the complication of far-field effects.

Provided herein is a method of priming tissue surrounding a nerve by adjusting the pH to enhance the effectiveness of a denervation composition or therapeutic agent delivered to said nerve or delivered to said tissue surrounding such nerve. Provided herein is a method of adjusting the pH of tissue surrounding a nerve in order to enhance the effectiveness of a denervation composition or therapeutic agent delivered to said nerve or delivered to said tissue surrounding such nerve. In some embodiments, the pH of the tissue is adjusted to be alkaline. In some embodiments, the pH of the tissue is adjusted to be acidic. In some embodiments, the pH of the tissue is adjusted to be neutral pH. There are multiple ways such pH of the tissue can be adjusted, any of which are intended to be covered herein, and of which several examples are discussed in more detail herein without intention to limit coverage to such examples.

Agent Delivery, Modulator Delivery (Any Order):

Provided herein is a method of delivering a therapeutic agent to a subject that locally denervates nerves comprising delivering the therapeutic agent to the subject and delivering a modulator or composition that is effective to modulate the local pH of the tissue surrounding the nerves that are the target of denervation. The delivery of the therapeutic agent and/or of the modulator or composition may be transluminal using one or more device as described herein, for example. Such delivery of said composition may be during, before, or after the delivery of the agent. The therapeutic agent may be guanethidine, or another therapeutic agent noted herein. The modulation may change the pH of the tissue to at least 7, to between 7 and 11, or between 8 and 10, or to between 8.5 and 9.5, for non-limiting example. In some embodiments, the modulator is a buffer or a buffer agent. In some embodiment the composition comprises a buffer or a buffer agent. In some embodiments, delivering the therapeutic agent and delivering the modulator or composition is done simultaneously, concurrently, or sequentially, using the same injection devices or using separate injection devices.

Modulator Delivery Alone

In another embodiment, the method comprises delivery of a composition that locally modulates the pH of the tissue surrounding the nerves that are the target of denervation without the need for a therapeutic agent. In such an embodiment, the composition itself achieves the therapeutic goal of denervating the target nerves.

Buffered Agent Delivery

In another embodiment, the method comprises delivery of a composition that has been pH-modulated prior to delivery to the tissue surrounding the nerve. Such composition may comprise a pH modulator and the therapeutic agent. In some embodiments, a composition comprises a therapeutic agent and a pH modulator. In some embodiments, a composition comprises a therapeutic agent at a pH of at least 7, between 7 and 11, between 8 and 10, or between 8.5 and 9.5, for non-limiting example. In some embodiments an aqueous solution comprising the therapeutic agent alone (without the modulator) is more acidic than the composition comprising the aqueous solution of therapeutic agent and the modulator. In some embodiments an aqueous solution comprising the therapeutic agent alone (without the modulator) is more alkaline than the composition comprising the aqueous solution of therapeutic agent and the modulator. The pH modulator may be a buffer, an alkaline buffer, such as NaOH, or another buffer that adjusts the composition to a target pH, to at least 7, to between 7 and 11, to between 8 and 10, or to between 8.5 and 9.5, for non-limiting example. The pH modulator may be an acid, an acidic agent, or a salt of an acid or acidic agent. In such embodiment, the composition comprises a therapeutic agent and a pH modulator that modulates the pH of the composition to at least 7, to between 7 and 11, to between 8 and 10, or to between 8.5 and 9.5, for non-limiting example. Such composition may be delivered to the tissue surrounding the nerves that are the target of denervation. A single injection of said composition, in some embodiments, may be effective in denervating the target nerve or nerves. In some embodiments, the therapeutic agent comprises guanethidine, guanethidine monosulfate, or guanethidine hemisulfate, or any agent (i.e. therapeutic agent) noted elsewhere herein. In some embodiments, the modulator is a buffer or a buffer agent. In some embodiments the buffer comprises sodium hydroxide.

Guanethidine Hemisulfate Agent Delivery

In some embodiments, the method comprises delivery of a composition comprising a therapeutic agent in an aqueous solution having a pH that is alkaline. In some embodiments, the method comprises delivery of a composition comprising a therapeutic agent in an aqueous solution having a pH that is acidic. In such embodiments, a pH modulator is not necessary to achieve the pH that enhances the effectiveness of the therapeutic agent in denervating a nerve in the tissue to which the composition is delivered. Such a composition may comprise a therapeutic agent in an aqueous solution having a pH of at least 7, between 7 and 11, between 8 and 10, or between 8.5 and 9.5, for non-limiting example.

Provided herein is a composition comprising a guanidine with pH>8. In some embodiments, the guanidine is guanethidine. In some embodiments, the guanethidine includes monosulfate. In some embodiments, the guanethidine includes hemisulfate in a solution configured for denervation. In some embodiments, the guanethidine includes hemisulfate in a solution suitable for denervation. In some embodiments, the pH>9. In some embodiments, the pH>10.

In some embodiments, the composition further comprises an alkaline buffer. In some embodiments, the alkaline buffer comprises NaOH. In some embodiments, the alkaline buffer comprises NaOH in a molar ratio to the guanidine concentration of 50% or greater. In some embodiments, the alkaline buffer comprises NaOH in an equimolar or greater concentration to the guanidine.

In some embodiments, the composition further comprises a contrast medium. In some embodiments, the composition further comprises sodium chloride. In some embodiments, the sodium chloride is 0.7% to 0.9% of the solution. In some embodiments, the guanethidine monosulfate is in concentration of 0.1 mg/mL to 50 mg/mL. In some embodiments, the guanethidine monosulfate is in concentration of 1 mg/mL to 20 mg/mL.

Provided herein is a method for modulating local tissue physiology comprising the delivery of preparation comprising a liquid, gel, or semisolid into the tissue. In some embodiments, the preparation buffers the local tissue physiology by raising or lowering the pH of the local tissue. In some embodiments, the preparation comprises a therapeutic agent that has its index effect at a physiological condition modulated by the delivery of such preparation, but not having an index effect at neutral physiological condition. In some embodiments, the preparation further includes a therapeutic agent that has additional or enhanced index effect at a physiological condition modulated by the delivery of such preparation, but not having such additional or enhanced index effect at neutral physiological condition. In some embodiments, the therapeutic agent is delivered systemically and the tissue is modulated with local pH change to affect an enhanced buildup of therapeutic agent or improved therapeutic index in the locally modulated tissue. In some embodiments, the gel comprises a hydrogel. In some embodiments, the hydrogel consumes protons as it resorbs in the tissue. In some embodiments, the hydrogel is alkaline. In some embodiments, the preparation includes guanethidine monosulfate. In some embodiments, the preparation has a pH>8. In some embodiments, the preparation includes a contrast medium. In some embodiment the preparation is the composition as described herein. In some embodiments the preparation comprises the composition described herein.

Provided herein is a method of creating renal denervation comprising the localized delivery of an acid or base with sufficiently low or high pH to create localized nerve damage or destruction.

Provided herein is a method of creating renal denervation comprising the localized delivery of a non-isotonic or non-isoosmolar solution that creates neuronal destruction while sparing other local tissues.

Provided herein is a method of treating hypertension comprising the delivery of a preparation of guanethidine monosulfate at pH>8 or guanethidine hemisulfate at pH>8 into the renal artery adventitia and perivascular tissues.

In some embodiments, the method further comprises delivery from an intravascular aspect. A delivery device as described herein may be used, or another delivery device may be used. The delivery may be transluminal.

Provided herein is a method of treating heart failure comprising the delivery of a preparation of guanethidine monosulfate at pH>8 or guanethidine hemisulfate at pH>8 into the renal artery adventitia and perivascular tissues.

Provided herein is a method of treating insulin resistance comprising the delivery of a preparation of guanethidine monosulfate at pH>8 or guanethidine hemisulfate at pH>8 into the renal artery adventitia and perivascular tissues.

Provided herein is a method of treating systemic inflammation comprising the delivery of a preparation of guanethidine monosulfate at pH>8 or guanethidine hemisulfate at pH>8 into the renal artery adventitia and perivascular tissues.

Provided herein is a method of treating sleep apnea comprising the delivery of a preparation of guanethidine monosulfate at pH>8 or guanethidine hemisulfate at pH>8 into the renal artery adventitia and perivascular tissues.

Provided herein is a method of creating denervation comprising the localized delivery of an agent chosen from the following: a hypertonic saline, a detergent, a solvent, ethanol, a strong acid, a strong base, a buffer agent, an alkaline buffer agent, an acidic buffer agent, a composition having a sodium chloride content between 0.7% and 0.9%, a composition having pH of about 9.5, a composition having pH that is adjusted to about 9.5 by buffering with an alkaline buffer agent, a composition having pH that is adjusted to about 9.5 by buffering with sodium hydroxide, or a composition having pH of between 8 and 11. In some embodiments, the denervation is of a renal nerve. In some embodiments, the method creates renal denervation. In some embodiment the denervation is of a non-renal nerve, such as a nerve near a lung.

In some embodiments, the buffer agent comprises one or more of sodium hydroxide, sodium bicarbonate, magnesium hydroxide, sulfuric acid, hydrochloric acid, citric acid, acetic acid, sodium citrate, sodium acetate, boric acid, potassium dihydrogen phosphate, diethyl barbituric acid, 3-{[tris(hydroxymethyl)methyl]amino}propanesulfonic acid, N,N-bis(2-hydroxyethyl)glycine, tris(hydroxymethyl)aminomethane, N-tris(hydroxymethyl)methylglycine, 2-[Bis(2-hydroxyethyl)amino]-2-(hydroxymethyl)-1,3-propanediol, 3-[N-Tris(hydroxymethyl)methylamino]-2-hydroxypropanesulfonic acid, 4-2-hydroxyethyl-1-piperazineethanesulfonic acid, 2-{[tris(hydroxymethyl)methyl]amino}ethanesulfonic acid, 3-(N-morpholino) propanesulfonic acid, piperazine-N,N'-bis(2-ethanesulfonic acid), dimethylarsinic acid, saline sodium citrate, 2-(N-morpholino)ethanesulfonic acid, and glycine.

Provided herein is a method of creating denervation comprising the localized delivery of an agent chosen from the following: guanethidine in a concentration ranging from 1 µg/mL to 50 mg/mL at pH of greater than 7, guanethidine in a concentration ranging from 1 mg/mL to 30 mg/mL at pH of greater than 7, a composition comprising guanethidine having a sodium chloride content between 0.7% and 0.9%, a composition comprising guanethidine having pH of about 9.5, a composition comprising guanethidine having pH that is adjusted to about 9.5 by buffering with an alkaline buffer agent, a composition comprising guanethidine having pH that is adjusted to about 9.5 by buffering with sodium hydroxide, or a composition comprising guanethidine having pH of between 8 and 11. In some embodiments, the denervation is of a renal nerve. In some embodiments, the method creates renal denervation. In some embodiment the denervation is of a non-renal nerve, such as a nerve near a lung.

Provided herein is a method of creating denervation comprising the localized delivery of a first toxin entering cells through sodium channels, wherein such first toxin comprises one or more of: tetrodotoxin and batrachotoxin, a second toxin entering cells through potassium channels, wherein such second toxin comprises one or more of: aurotoxin, agitoxin, charybdotoxin, margatoxin, slotoxin, sycllatoxin and hefutoxin, and/or a third toxin entering cells through calcium channels, wherein such third toxin comprises one or more of: calciseptine, taicatoxin, calcicludine and PhTx3. In some embodiments, the denervation is of a renal nerve. In some embodiments, the method creates renal denervation. In some embodiment the denervation is of a non-renal nerve, such as a nerve near a lung.

Provided herein is a method of creating denervation comprising the localized delivery of an agent comprising an adrenergic blocker, an androgenic inhibitor, an adrenergic stimulator, an Alpha-/beta-adrenergic blocker, an angiotensin converting enzyme (ACE) inhibitor, an ACE-receptor antagonist, a Beta blocker, a calcium channel blocker, an antiarrythmic of groups I-IV, an antiarrythmic, a cardiotonic, an alpha-2-agonists, a guanidine derivative, an imadazoline receptor agonist, a ganglion-blocking agent, nicotinic antagonist, ganglion-blocking agents, nicotinic antagonist, a MAOI inhibitor, an adrenergic uptake inhibitor, a tyrosine hydroxylase inhibitors, an alpha-1 blocker, a non-selective alpha blocker, a serotonin antagonist, an endothelin antagonist, a sclerosing agent, or a sensory denervation agent. In some embodiments, the denervation is of a renal nerve. In some embodiments, the method creates renal denervation. In some embodiment the denervation is of a non-renal nerve, such as a nerve near a lung.

Provided herein is a method of creating denervation comprising the localized delivery of an agent comprising doxazosin, guanadrel, guanethidine, pheoxybenzamine, prazosin plus polythiazide, terazosin, methyldopa, clonidine, guanabenz, guanfacine, Labetalol, benazepril, catopril, enalapril, enalaprilat, fosinopril, lisinopril, moexipril, quinapril, ramipril, and combinations with calcium channel blockers and diuretics, losartan, acebutolol, atenolol, betaxolol, bisoprolol, carteolol, esmolol, fimolol, pindolol, propranolol, penbatolol, metoprolol, nadolol, sotalol, Amiloride, amlodipine, bepridil, diltiazem, isradipine, nifedipine, verapamil, felodipine, nicardipine, nimodipine, bretylium, disopyramide, encamide, flecamide, lidocaine, mexiletine, moricizine, propafenone, procainamide, quinidine, tocamide, esmolol, propranolol, acebutolol, amiodarone, sotalol, verapamil, diltiazem, pindolol, bupranolol hydrochloride, trichlormethiazide, furosemide, prazosin hydrochloride, metoprolol tartrate, carteolol hydrochloride, oxprenolol hydrochloride, and propranolol hydrochloride, adenosine, digoxin; metildigoxin, caffeine, dopamine hydrochloride, dobutamine hydrochloride, octopamine hydrochloride, diprophylline, ubidecarenon, digitalis, capsaicin, anti-nerve growth factor, anti-dopamine beta-hydroxylase, anti-acetylcholinesterase, 6-hydroxyldopamine (6-OHDA), bretylium tosylate, guanacline, and N-(2-chloroethyl)-N-ethyl-2-bromobenzylamine (DSP4), OX7-SAP, 192-SAP, anti-dopamine beta-hydroxylase saporin (DBH-SAP), and anti-dopamine beta-hydroxylase immunotoxin (DHIT), phenol, ethanol, clonidine, guanfacine, methyldopa, betanidine, guanoxan, debrisoquine, guanoclor, guanazodine, guanoxabenz, moxonidine, relmenidine, mecamylamine, trimethaphan, pargyline, rescinnamine, reserpine, metirosine, prazosin, indoramin, trimazosin, doxazosin, urapidil, phentolamine, ketanserin, bosentan, ambrisentan, sitaxentan, quinacrine, chloroquine, sodium tetradecyl sulfate, ethanolamine oleate, sodium morrhuate, polidocanol, or a hypertonic solution. In some embodiments, the denervation is of a renal nerve. In some embodiments, the method creates renal denervation. In some embodiment the denervation is of a non-renal nerve, such as a nerve near a lung.

In some embodiments, the agent itself or a composition comprising such agent has a pH of at least 7, a pH of at most 11, a pH of at least 7 and at most 11, a pH of at least 8 and at most 10, a pH that is effective to denervate nerves to which such agent is delivered, or a pH that is adjusted to a level that is effective to denervate nerves to which such agent is delivered.

EXAMPLES

Example 1

In Vitro Response of Nerve and Smooth Muscle Cells to pH and Guanethidine Monosulfate Concentration Guanethidine Monosulfate and pH interaction studies were performed on sympathetic neuronal and perivascular and vascular cell types. The following cell types were examined:

SH-SY5Y: Human neuroblastoma line SH-SY5Y, plated but uninduced

Induced SH-SY5Y: SH-SY5Y induced with retinoic acid to differentiate into neurite growing sympathetic nerve cells rPC-12: Adherent-type rat PC-12 cells, plated but uninduced Induced rPC-12: PC-12 induced with NGF to differentiate into neurite growing sympathetic nerve cells Rat SCG: Primary rat superior cervical ganglia cells hAoSMC: Primary human aortic smooth muscle cells Cells were treated with 0, 1, 10, 100 or 1000 µg/mL guanethidine monosulfate (GNT), or 10 µg/mL GNT and 17% IsoVUE370, at pH 6.3 and pH 9.3. At 4 h and in replicate cultures at 24 h, the medium was replaced with regular growth medium with the same drug concentrations. Stepwise, the test method was as follows: treat the cells with the composition of guanethidine monosulfate at either pH 6.3 or pH 9.3 (at concentration 0, 1, 10, 100 or 1000 μg/mL guanethidine monosulfate or 10 μg/mL GNT and 17% IsoVUE370); wait 4 hours or 24 hours, then replace the medium with a composition of guanethidine monosulfate without pH modulation (at concentration 0, 1, 10, 100 or 1000 μg/mL guanethidine monosulfate or 10 μg/mL GNT and 17% IsoVUE370); at 48 hours test cells for viability by Alamar blue (~4 h incubation); replace the guanethidine monosulfate without pH modulation with standard growth medium; at 7 days, test cells for viability by Alamar blue (~4 h incubation). The data for the 10 μg/mL GNT and 17% IsoVUE370 is presented in FIGS. 17A-17L labeled on the x-axis as 10+IV. With Rat SCG cells, further testing was carried out to examine the effect of pH 9.3 exposure for 1 hour or pH 7.3 (normal growth medium) for 24 hours. These cells were examined at 24 hours only. Cells were examined microscopically just before pH or drug additions and again at 48 hours. Observations were noted and photographed.

Cells were tested for viability by Alamar blue in ~4 hour incubation at 48 hours (2 days) and 7 days, as noted above. Toxicity of drug and pH conditioning were compared against negative controls of growth medium only and positive controls of 1% Triton (TX-100) in normal growth medium. All conditions were run in triplicate. Guanethidine samples were prepared from USP guanethidine monosulfate reference standard (CAS 645-43-2).

Radiofrequency ablation of renal artery sympathetic nerves has been shown to reduce blood pressure in drug-resistant hypertension. (Doumas M, Douma S. *Interventional management of resistant hypertension*, Lancet, 2009; 373:1228-1229.) The physiologic mechanism linking renal denervation and hypertension is the reduction of norepinephrine (NE) production by the renal sympathetic nerves. (DiBona G F, Esler M. *Translational medicine: the antihypertensive effect of renal denervation*, Am J Physiol Regul Integr Comp Physiol. 2010 February; 298(2):R245-53. Epub 2009 Dec. 2.) Complete renal denervation creates a ~90% decrease in renal tissue NE content in pigs (reduced from 452±83 to 15±27 ng/g and dogs (reduced from 260±19 to 24±12 ng/g). (Connors B A, Evan A P, Willis L R, Simon J R, Fineberg N S, Lifshitz D A, Shalhav A L, Paterson R F, Kuo R L, Lingeman J E. *Renal nerves mediate changes in contralateral renal blood flow after extracorporeal shock-wave lithotripsy*, Nephron Physiol. 2003; 95(4):p67-75; Mizelle H L, Hall J E, Woods L L, Montani J P, Dzielak D J, Pan Y J. *Role of renal nerves in compensatory adaptation to chronic reductions in sodium intake*, Am J. Physiol. 1987 February; 252(2 Pt 2):F291-8.)

There have been reductions in pressure reported, and NE spillover from denervated renal arteries was reported to drop by an average of 47% (N=10 patients) in the 15 to 30 days after the procedure. (Doumas 2009.) The renal sympathetic nerves are located in the renal artery adventitia.

Certain experiments have shown that guanethidine denervation in porcine renal artery adventitia through kidney cortex NE drops of 49-58% and histological evidence of nerve deterioration and fibrosis there is shown herein pH dependency of this effect based on a lack of denervation with guanethidine +IsoVUE with pH of 6.3 as compared to guanethidine +IsoVUE with pH of 9.3.

Guanethidine Monosulfate has a molecular weight of 296.39 g/mol. The concentration of 10 mg/mL results in a molar concentration of 33.7 mmol/L (33.7 mM). Concentrations at or above 0.2 mM (60 μg/mL) have been shown to produce axon retraction in vitro. (Hill C E et al. *Use of tissue culture to examine the actions of guanethidine and 6-hydroxydopamine*, European Journal of Pharmacology 1973; 23:1620-74.)

Guanethidine has been shown to have pH dependent effects on primary rat superior cervical ganglia neurons in culture, with cytotoxicity of 100 ng/mL at pH of 8.0 and a lack of cytotoxicity at pH of 7.2 (Johnson E M and Aloe L. *Suppression of the in vitro and in vivo cytotoxic effects of guanethidine in sympathetic neurons by nerve growth factor*, Brain Research 1974; 81:519-532; Wakshull E, Johnson M I, Burton H. *Persistence of an amine uptake system in cultured rat sympathetic neurons which use acetylcholine as their transmitter*, J. Cell Biology 1978; 79:121-131.)

Alamar blue is proven cell viability indicator that uses the natural reducing power of living cells to convert resazurin to the fluorescent molecule, resorufin. The active ingredient of Alamar blue (resazurin) is a nontoxic, cell permeable compound that is blue in color and virtually nonfluorescent. Upon entering cells, resazurin is reduced to resorufin, which produces very bright red fluorescence. Viable cells continuously convert resazurin to resorufin, thereby generating a quantitative measure of viability—and cytotoxicity.

In an attempt to replicate behavior of post-ganglionic sympathetic neurons, rat pheochromocytoma cells (PC-12), human neuroblastoma cells (SH-SY5Y) and primary rat superior cervical ganglion (rat SCG) cells were used in these experiments. Each cell type was able to be propagated to form neurites in these experiments. After Alamar blue incubation, fluorescence units (FU) were measured in all samples.

Figure 17A:
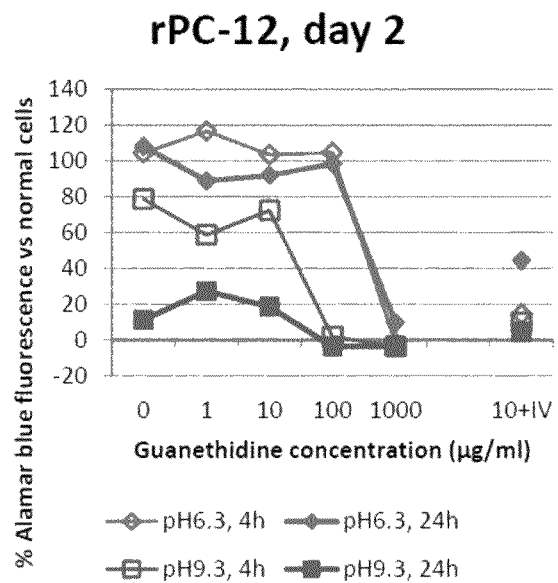
FIGS. 17A-17L show the results of the viability testing run in triplicate by Alamar blue in about 4 or 24 hours of incubation at 48 hours i.e. 2 days (left column including FIGS. 17A, 17C, 17E, 17G, 17I and 17K plots) and at 7 days (right column including FIGS. 17B, 17D, 17F, 17H, 17J and 17L plots)

FIGS. 17A-17L show the results of the viability testing run in triplicate by Alamar blue in about 4 hours of incubation at 48 hours i.e. 2 days (left column including FIGS. 17A, 17C, 17E, 17G, 17I and 17K plots) and at 7 days (right column including FIGS. 17B, 17D, 17F, 17H, 17J and 17L plots) Data presented below and in FIGS. 17A through 17L were calculated with the following equation, where sample fluorescence minus background is $FU_{sample}$, fluorescence of cells in growth medium minus background is $FU_{negative\ control}$, and fluorescence of cells after exposure to 1% Triton (killing all cells) minus background fluorescence is $FU_{positive\ control}$. The equation is: $\% = 100 \times ((FU_{sample} - FU_{positive\ control})/(FU_{negative\ control} - FU_{positive\ control}))$ FIG. 17A shows % Alamar blue fluorescence versus normal cells in rPC-12 at day 2, for guanethidine at pH 6.3 for 4 hours (top line having an open diamond marker at 1 μg/mL guanethidine concentration), for guanethidine at pH 6.3 for 24 hours (second line from the top having a solid diamond marker at 1 μg/mL guanethidine concentration), for guanethidine at pH 9.3 for 4 hours (third line from the top having an open square marker at 1 μg/mL guanethidine concentration), and for guanethidine at pH 9.3 for 24 hours (bottom line having a solid square marker at 1 μg/mL guanethidine concentration).

Figure 17B:
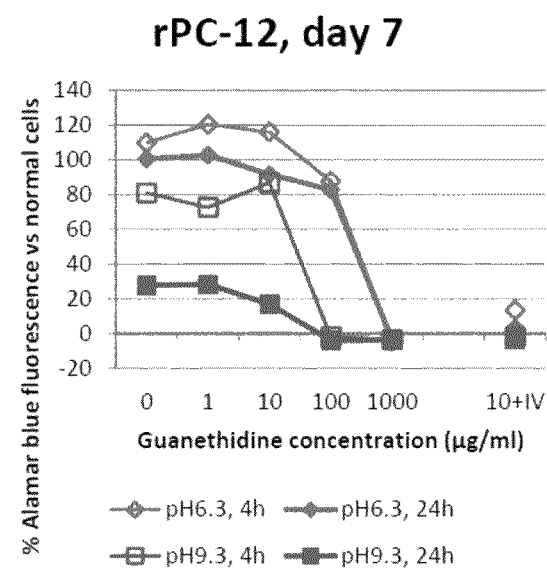

FIG. 17B shows % Alamar blue fluorescence versus normal cells in rPC-12 at day 7, for guanethidine at pH 6.3 for 4 hours (top line having an open diamond marker at 1 μg/mL guanethidine concentration), for guanethidine at pH 6.3 for 24 hours (second line from the top having a solid diamond marker at 1 μg/mL guanethidine concentration), for guanethidine at pH 9.3 for 4 hours (third line from the top having an open square marker at 1 μg/mL guanethidine concentration), and for guanethidine at pH 9.3 for 24 hours (bottom line having a solid square marker at 1 μg/mL guanethidine concentration).

Figure 17C:
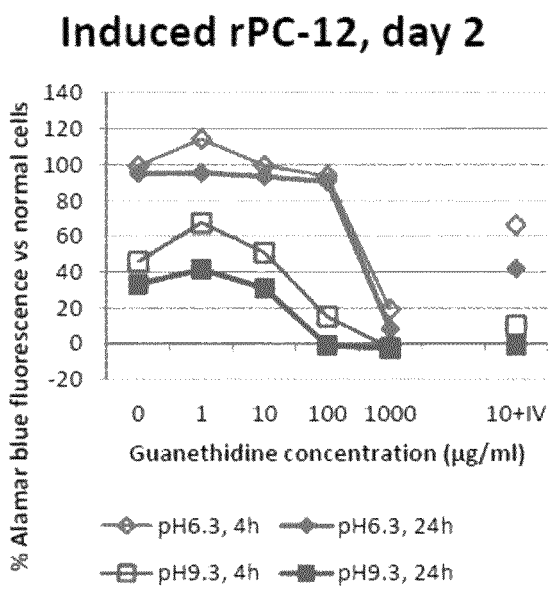

FIG. 17C shows % Alamar blue fluorescence versus normal cells in induced rPC-12 at day 2, for guanethidine at pH 6.3 for 4 hours (top line having an open diamond marker at 1 µg/mL guanethidine concentration), for guanethidine at pH 6.3 for 24 hours (second line from the top having a solid diamond marker at 1 µg/mL guanethidine concentration), for guanethidine at pH 9.3 for 4 hours (third line from the top having an open square marker at 1 µg/mL guanethidine concentration), and for guanethidine at pH 9.3 for 24 hours (bottom line having a solid square marker at 1 µg/mL guanethidine concentration).

Figure 17D:
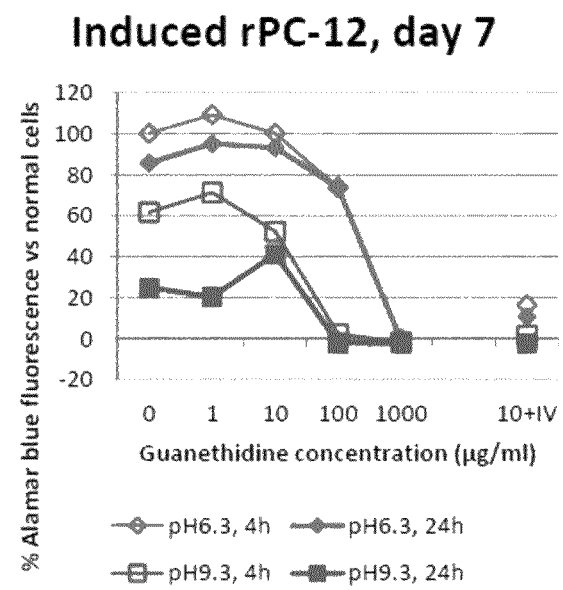

FIG. 17D shows % Alamar blue fluorescence versus normal cells in induced rPC-12 at day 7, for guanethidine at pH 6.3 for 4 hours (top line having an open diamond marker at 1 µg/mL guanethidine concentration), for guanethidine at pH 6.3 for 24 hours (second line from the top having a solid diamond marker at 1 µg/mL guanethidine concentration), for guanethidine at pH 9.3 for 4 hours (third line from the top having an open square marker at 1 µg/mL guanethidine concentration), and for guanethidine at pH 9.3 for 24 hours (bottom line having a solid square marker at 1 µg/mL guanethidine concentration).

Figure 17E:
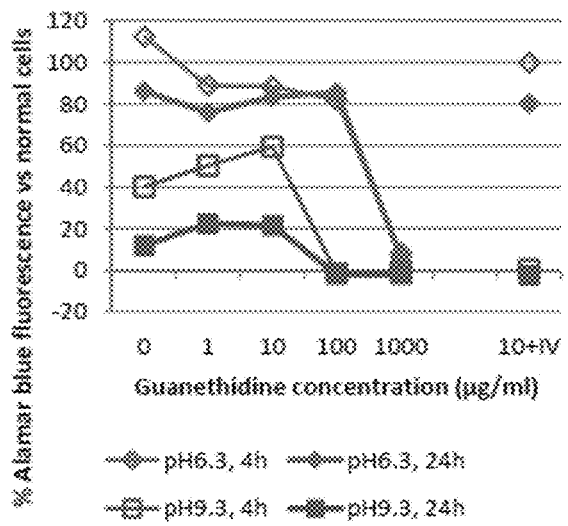

FIG. 17E shows % Alamar blue fluorescence versus normal cells in SH-SY5Y at day 2, for guanethidine at pH 6.3 for 4 hours (top line having an open diamond marker at 1 µg/mL guanethidine concentration), for guanethidine at pH 6.3 for 24 hours (second line from the top having a solid diamond marker at 1 µg/mL guanethidine concentration), for guanethidine at pH 9.3 for 4 hours (third line from the top having an open square marker at 1 µg/mL guanethidine concentration), and for guanethidine at pH 9.3 for 24 hours (bottom line having a solid square marker at 1 µg/mL guanethidine concentration).

Figure 17F:
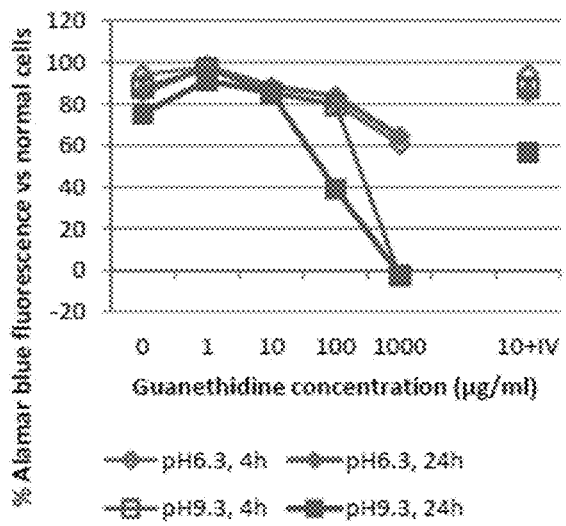

FIG. 17F shows % Alamar blue fluorescence versus normal cells in SH-SY5Y at day 7, for guanethidine at pH 6.3 for 4 hours (top line having an open diamond marker at 0 µg/mL guanethidine concentration), for guanethidine at pH 6.3 for 24 hours (second line from the top having a solid diamond marker at 0 µg/mL guanethidine concentration), for guanethidine at pH 9.3 for 4 hours (overlapping the solid diamond marker and line from the top and having an open square marker at 0 µg/mL guanethidine concentration), and for guanethidine at pH 9.3 for 24 hours (bottom line having a solid square marker at 0 µg/mL guanethidine concentration.

Figure 17G:
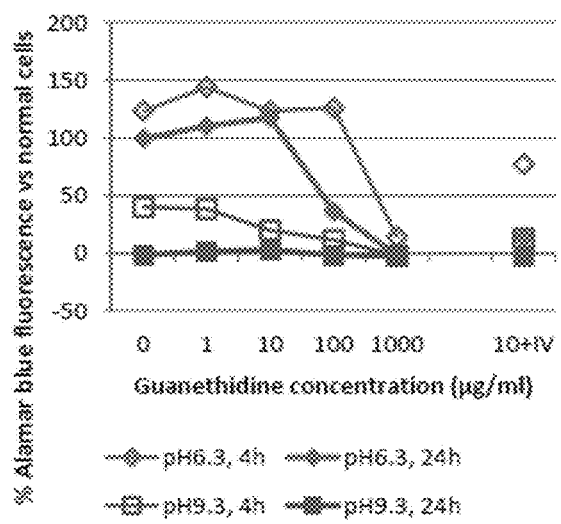

FIG. 17G shows % Alamar blue fluorescence versus normal cells in induced SH-SY5Y at day 2, for guanethidine at pH 6.3 for 4 hours (top line having an open diamond marker at 1 µg/mL guanethidine concentration), for guanethidine at pH 6.3 for 24 hours (second line from the top having a solid diamond marker at 1 µg/mL guanethidine concentration), for guanethidine at pH 9.3 for 4 hours (third line from the top having an open square marker at 1 µg/mL guanethidine concentration), and for guanethidine at pH 9.3 for 24 hours (bottom line having a solid square marker at 1 µg/mL guanethidine concentration).

Figure 17H:
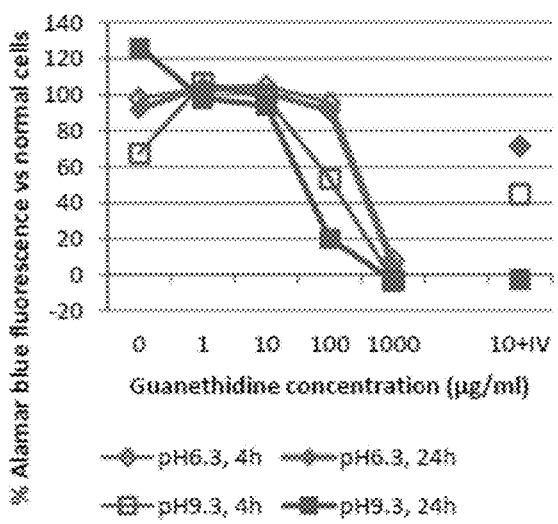

FIG. 17H shows % Alamar blue fluorescence versus normal cells in induced SH-SY5Y at day 7, for guanethidine at pH 6.3 for 4 hours (second line from the top having an open diamond marker at 0 µg/mL guanethidine concentration), for guanethidine at pH 6.3 for 24 hours (third line from the top having a solid diamond marker at 0 µg/mL guanethidine concentration), for guanethidine at pH 9.3 for 4 hours (bottom line having an open square marker at 0 µg/mL guanethidine concentration), and for guanethidine at pH 9.3 for 24 hours (top line having a solid square marker at 0 µg/mL guanethidine concentration).

Figure 17I:
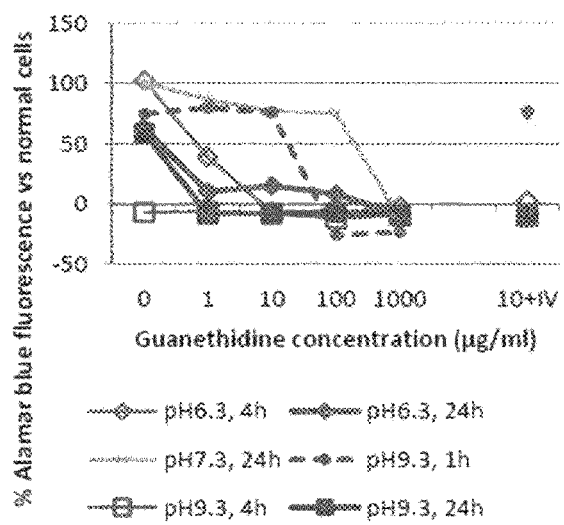

FIG. 17I shows % Alamar blue fluorescence versus normal cells in Rat SCG at day 2, for guanethidine at pH 6.3 for 4 hours (third line from the top having an open diamond marker at 1 µg/mL guanethidine concentration), for guanethidine at pH 6.3 for 24 hours (fourth line from the top having a solid diamond marker at 1 µg/mL guanethidine concentration), for guanethidine at pH 9.3 for 4 hours (bottom line from the top having an open square marker at 1 µg/mL guanethidine concentration—overlapping with the 24 hour pH 9.3 data), for guanethidine at pH 9.3 for 24 hours (bottom line having a solid square marker at 1 µg/mL guanethidine concentration—overlapping with the pH 9.3 at 4 hours), for guanethidine at pH 7.3 (neutral) for 24 hours (top line having an asterisk marker at 1 µg/mL guanethidine concentration), and guanethidine at pH 9.3 for 1 hour (second line from the top having a solid circle marker at 1 µg/mL guanethidine concentration).

Figure 17J:
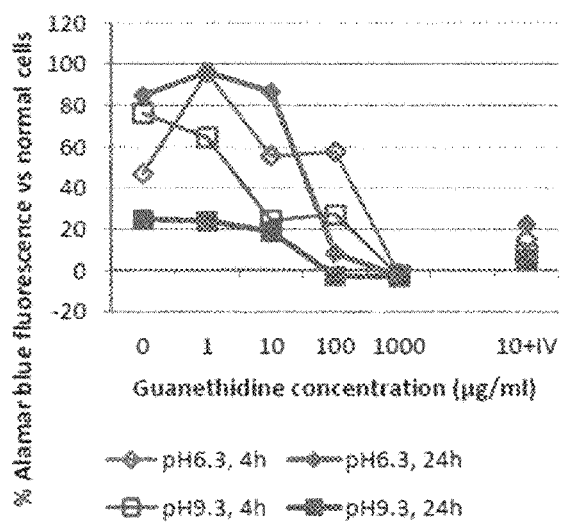

FIG. 17J shows % Alamar blue fluorescence versus normal cells in Rat SCG at day 7, for guanethidine at pH 6.3 for 4 hours (third line from the top having an open diamond marker at 0 µg/mL guanethidine concentration), for guanethidine at pH 6.3 for 24 hours (top line having a solid diamond marker at 0 µg/mL guanethidine concentration), for guanethidine at pH 9.3 for 4 hours (second line from the top having an open square marker at 0 µg/mL guanethidine concentration), and for guanethidine at pH 9.3 for 24 hours (bottom line having a solid square marker at 1 µg/mL guanethidine concentration).

Figure 17K:
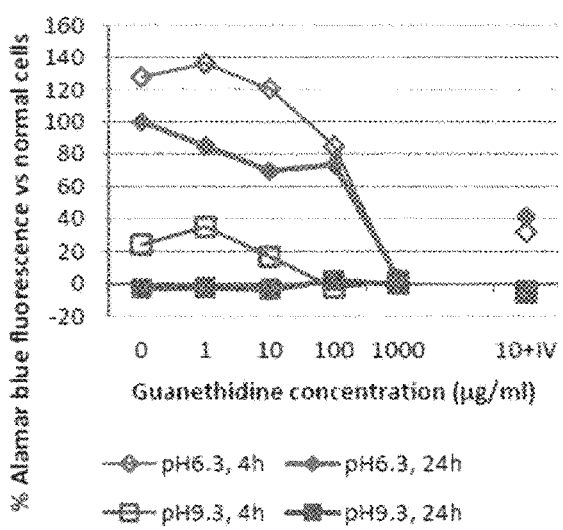

FIG. 17K shows % Alamar blue fluorescence versus normal cells in hAoSMC at day 2, for guanethidine at pH 6.3 for 4 hours (top line having an open diamond marker at 1 µg/mL guanethidine concentration), for guanethidine at pH 6.3 for 24 hours (second line from the top having a solid diamond marker at 1 µg/mL guanethidine concentration), for guanethidine at pH 9.3 for 4 hours (third line from the top having an open square marker at 1 µg/mL guanethidine concentration), and for guanethidine at pH 9.3 for 24 hours (bottom line having a solid square marker at 1 µg/mL guanethidine concentration).

Figure 17L:
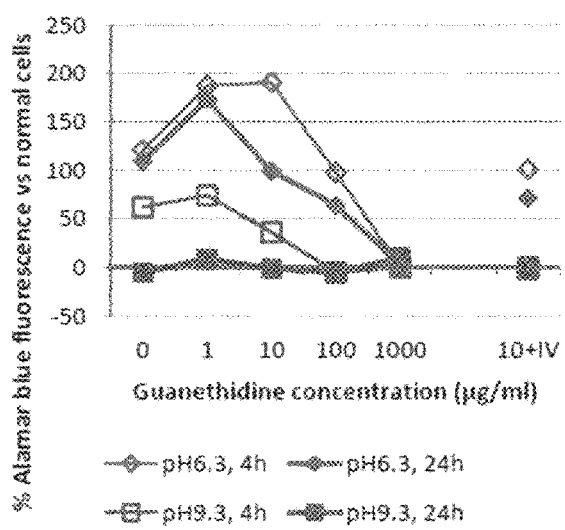

FIG. 17L shows % Alamar blue fluorescence versus normal cells in hAoSMC at day 7, for guanethidine at pH 6.3 for 4 hours (top line having an open diamond marker at 1 µg/mL guanethidine concentration), for guanethidine at pH 6.3 for 24 hours (second line from the top having a solid diamond marker at 1 µg/mL guanethidine concentration), for guanethidine at pH 9.3 for 4 hours (third line from the top having an open square marker at 1 µg/mL guanethidine concentration), and for guanethidine at pH 9.3 for 24 hours (bottom line having a solid square marker at 1 µg/mL guanethidine concentration).

The LC50 is the concentration of drug that is lethal to 50% of cells. Calculation from the data shown above and as shown in FIGS. 17A through 17L yielded the LC50 values as shown in Table 1. If pH effects led to <50% surviving cells without drug addition, a "0" is found in the LC50 chart. If the LC50 was between zero and the lowest dose (1 µg/mL), the LC50 value is listed as "<1". Calculations were not performed for pH exposures of 24 hours, since LC50 was often zero with such extended exposure and since 24 hour pH exposure is unlikely in vivo, where pH would likely neutralize in the injected tissue much more rapidly than 24 hours.

TABLE 1

| LC50 Values (μg/mL) Cell type | 2-day examination | | | | 7-day examination | |
|---|---|---|---|---|---|---|
| | Neutral pH | 1 h @ pH 9.3 | 4 h @ pH 6.3 | 4 h @ pH 9.3 | 4 h @ pH 6.3 | 4 h @ pH 9.3 |
| SH-SY5Y | NT | NT | 271 | 14.3 | >1000 | 229 |
| Induced SH-SY5Y | NT | NT | 477 | 0 | 334 | 114 |
| PC-12 | NT | NT | 326 | 20.8 | 257 | 26.0 |
| Induced PC-12 | NT | NT | 385 | 10.6 | 210 | 11.2 |
| SCG | 195 | 17.8 | <1 | 0 | 134 | 2.3 |

NT: Not Tested

Figure 19A:
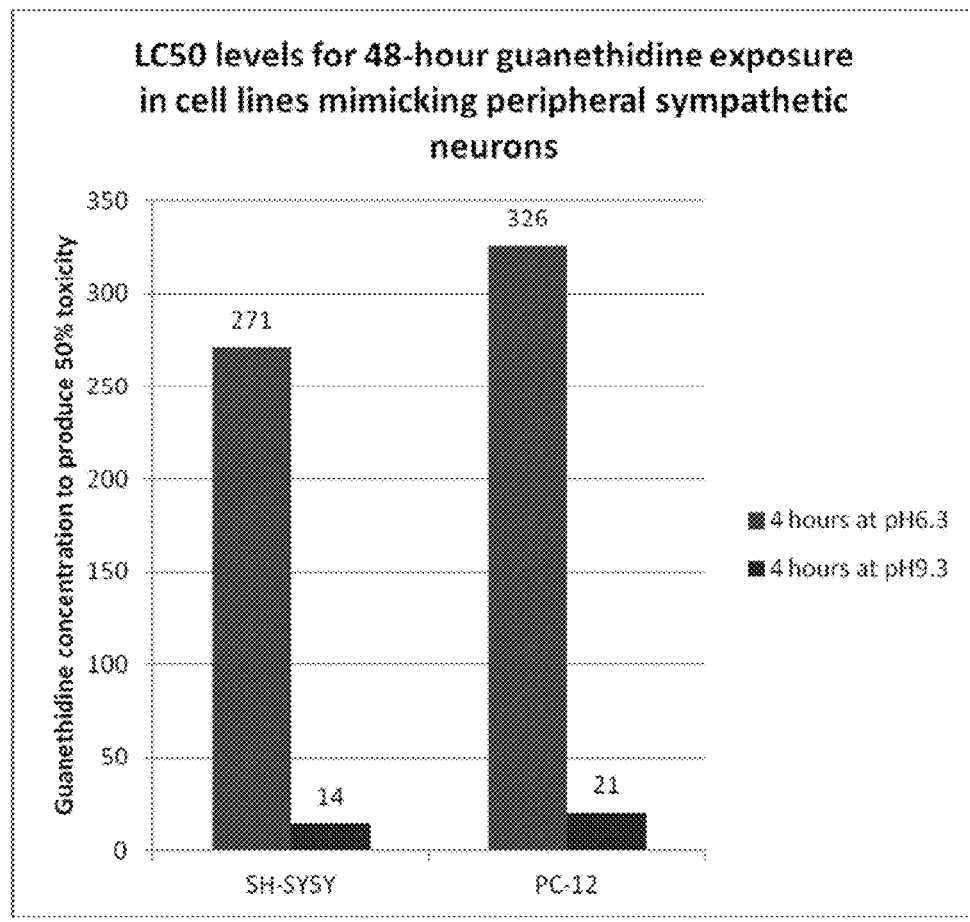
FIG. 19A provides in vitro confirmation of high-pH guanethidine effects showing the LC50 levels for 48 hour guanethidine exposure in cell lines mimicking peripheral sympathetic neurons, in the first column SH-SY5Y cells were tested at 4-hours at pH 6.3, in the second column SH-SY5Y cells were tested at 4-hours at pH 9.3, in the third column PC-12 cells were tested at 4-hours at pH 6.3, and in the fourth column PC-12 cells were tested at 4-hours at pH 9.3.
Figure 19B:
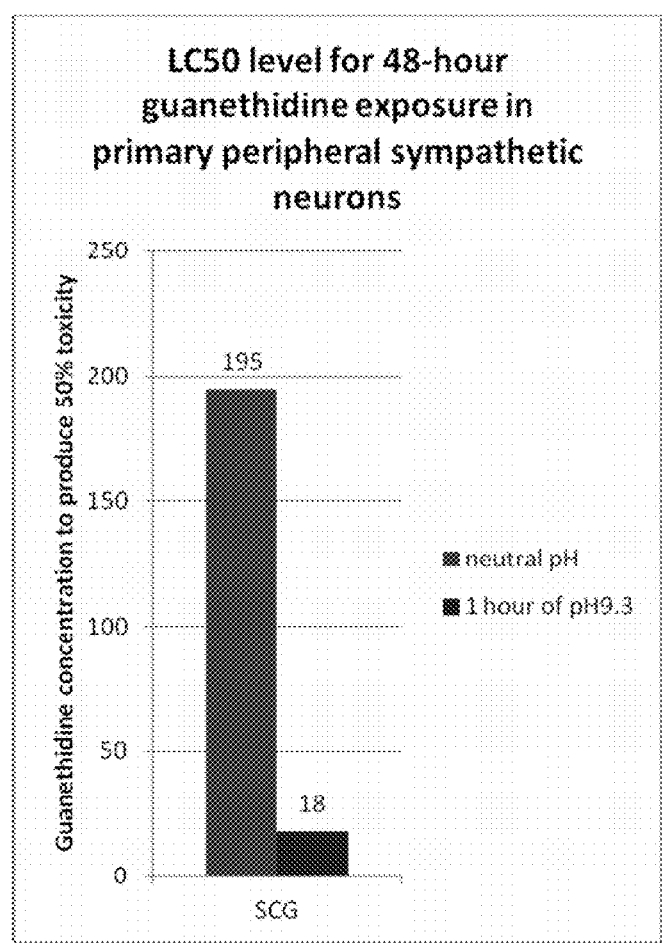
FIG. 19B provides in vitro confirmation of high-pH guanethidine effects showing the LC50 levels for 48 hour guanethidine exposure in primary peripheral sympathetic neurons, in the first column SCG cells were tested at a neutral pH, in the second column SCG cells were tested at 1 hours at pH 9.3.

FIG. 19A provides in vitro confirmation of high-pH guanethidine effects showing the LC50 levels for 48 hour guanethidine exposure in cell lines mimicking peripheral sympathetic neurons, in the first column SH-SY5Y cells were tested at 4-hours at pH 6.3, in the second column SH-SY5Y cells were tested at 4-hours at pH 9.3, in the third column PC-12 cells were tested at 4-hours at pH 6.3, and in the fourth column PC-12 cells were tested at 4-hours at pH 9.3. FIG. 19B provides in vitro confirmation of high-pH guanethidine effects showing the LC50 levels for 48 hour guanethidine exposure in primary peripheral sympathetic neurons, in the first column SCG cells were tested at a neutral pH, in the second column SCG cells were tested at 1 hours at pH 9.3. In FIGS. 19A and 19B, the y-axis is in units of μg/mL.

Extended exposure (24 hours) to pH 9.3 causes some amount of degradation of most of the cell types studied, while 24 hours of exposure to pH 6.3 has limited effect on the cells. With 4 hours of exposure to pH 9.3 or pH 6.3, apparent differences are seen in the toxic concentrations of guanethidine to each of the neuronal cell lines studied in these experiments. This observation holds true whether cells are examined directly after 48 hours of drug exposure or at 7 days. In every cell type studied, guanethidine was toxic to cells with an order of magnitude less concentration at pH 9.3 than at pH 6.3.

Follow-up study with pH 9.3 in the rat SCG cells for 1 hour of exposure showed a guanethidine dose-dependent toxicity.

In vivo experiments with pH 9.3 guanethidine resulted in significant observable neurotoxicity with pH 9.3 guanethidine administered at 10 mg/mL at 28 and 60 days, while in vivo experiments with pH 6.3 guanethidine administered at 10 mg/mL resulted in no significant alteration of the renal sympathetic nerves at 90 days.

This would indicate that in vivo, following injections of pH 9.3 guanethidine, the pH of the tissue remains alkaline for long enough to enhance the uptake and/or cytotoxic effects of guanethidine on neurons. It should be noted, however, that the cytotoxicity of guanethidine in vivo with pH 9.3 was not apparent in non-neuronal cell types.

Finally, in vivo experiments with injection of pH 9.3 administered at 10 mg/mL guanethidine in 50 mg dose per artery resulted in tissue guanethidine concentrations of 4.3±2.9 μg/g (expressed in amount of guanethidine per weight of tissue) in renal artery and 1.9±1.0 μg/g in renal perivascular tissues at 24 hours. These concentrations compare well to the LC50 levels reported above. While these average tissue concentrations are slightly lower than the observed LC50 values, there is likely an averaging effect from the in vivo studies since guanethidine is known to concentrate in nerve cells, but nerve cells are only a small portion of the total tissue mass evaluated in those earlier concentration studies.

In summary, these studies show that Guanethidine has improved neuronal cell toxicity at pH 9.3 as compared with pH 6.3. Toxicity in response to guanethidine showed dose-dependent effects at both pH 6.3 and pH 9.3, with LC50 at least 10× higher with pH 6.3 than pH 9.3 in the majority of cell lines studied. Additionally, Time of exposure to pH 6.3 had less of an effect than time of exposure to pH 9.3, with increased exposure times to pH 9.3 causing toxic effects at low or no guanethidine concentrations.

Example 2

Animal Study and Follow Up Studies

Guanethidine tested in certain preclinical studies showed that there was nerve damage, however the form of the guanethidine tested in these studies was guanethidine hemisulfate. Later testing in an animal study using guanethidine monosulfate at an unbuffered pH (6.3 or less) produced safe results, but failed to show significant denervation. Buffering of guanethidine monosulfate to a pH in the ranges successfully shown to denervate using guanethidine hemisulfate is possible. Titration experiments as shown in FIG. 20B depict how guanethidine monosulfate can be buffered with sodium hydroxide to achieve the same pH as the guanethidine hemisulfate used in the studies with successful denervation. This alkaline buffered form of guanethidine monosulfate may be used to denervate nerves by delivery of such composition to tissue surrounding such nerves. Such delivery may be transluminal, for example using devices noted herein, or may be delivered in another way to the tissue surrounding the nerve (or nerves) to be denervated. Guanethidine effect is pH dependent such that there is increased neurotoxicity at higher pH. Guanethidine at a neutral pH can block nerves, but does not denervate. Locally elevated pH of guanethidine (whether buffered monosulfate or hemisulfate) destroys nerves and spares surrounding tissues. Thus, a composition that comprises guanethidine hemisulfate, or one that alternatively comprises buffered guanethidine monosulfate having an elevated pH would be effective in denervation, as well as be safe. This effect allows for precise local denervation without regional or systemic effects of the drug.

Aqueous monosulfate form has two free hydrogen ions for each guanethidine molecule (the free hydrogen comes from the sulfate molecule, which breaks into $SO_4^{2-}$ and $2H^+$. However, the hemisulfate aqueous form has only one free hydrogen ion for each guanethidine molecule. This leads to a predominantly dual protonated form (and thus acidic pH) of an aqueous solution of the monosulfate, but a predominantly single protonated form (thus alkaline pH) of the hemisulfate. Removal of hydrogen ions from the aqueous solution leads to higher pH and less protonation of the guanethidine.

Figure 18A:
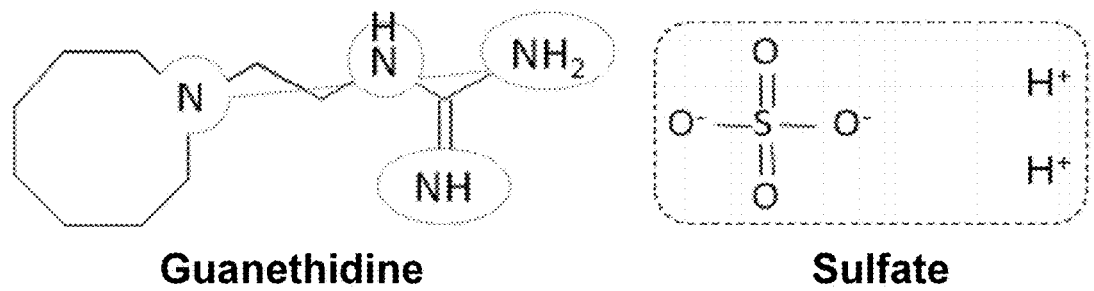
FIGS. 18A-18D depict the differences between guanethidine monosulfate in FIG. 18D and guanethidine hemisulfate in FIG. 18C, the monosulate having a lower pH and found in certain preclinical studies to have inconclusive or null results and the hemisulfate having a higher pH and found in certain preclinical studies to have good preclinical results.
Figure 18B:
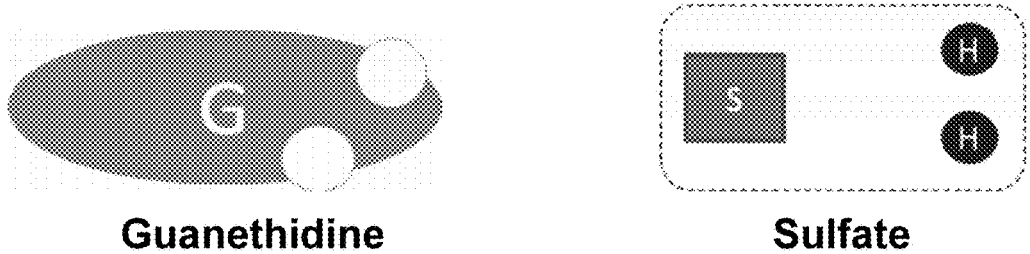
Figure 18C:
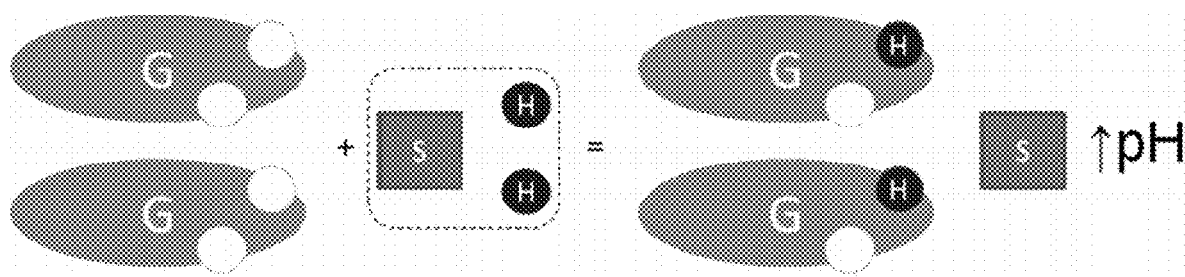
Figure 18D:
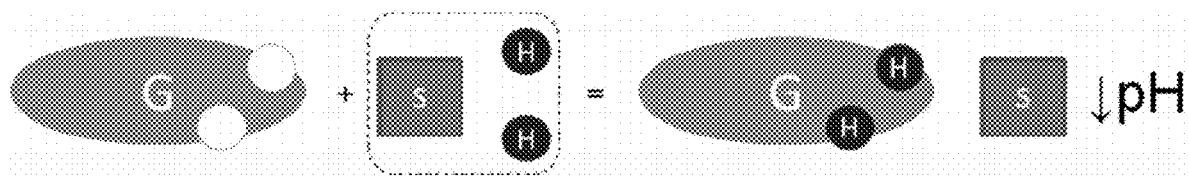

FIGS. 18A-18D depict the differences between guanethidine monosulfate in FIG. 18D and guanethidine hemisulfate in FIG. 18C, the monosulfate salt form having a lower pH in aqueous solution and found in certain preclinical studies to have inconclusive or null results and the hemisulfate salt form having a higher pH in aqueous solution and found in certain preclinical studies to have positive preclinical results.

Figure 20A:
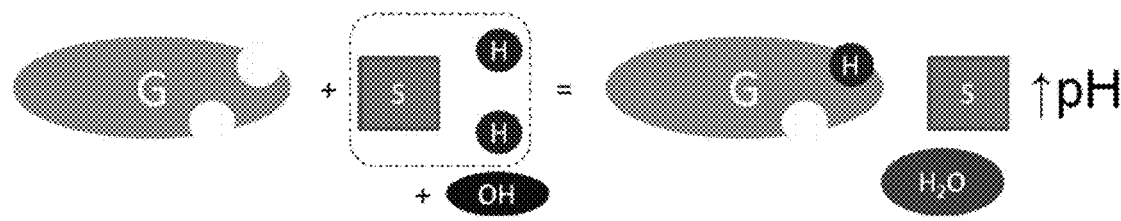
FIG. 20A depicts an embodiment composition of guanethidine monosulfate in solution that is buffered to increase the pH, for example to a pH level of guanethidine hemisulfate in solution.
Figure 20B:
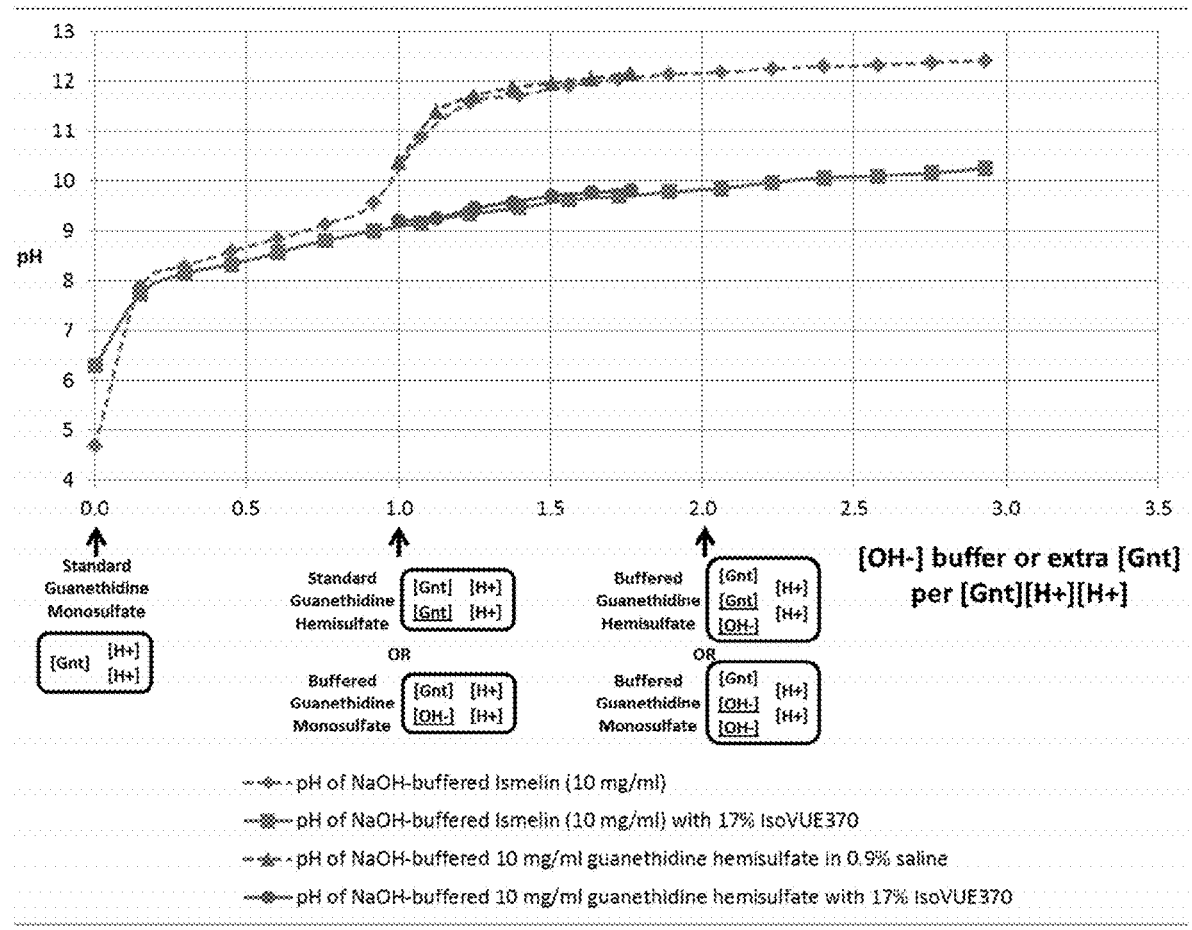
FIG. 20B depicts guanethidne monosulfate buffering that is possible to reach the pH of guanethidine hemisulfate, wherein the NaOH-buffered guanethidine monosulfate (Ismelin) 10 mg/mL data is shown in the data having a diamond marker with dashed line (starting in the bottom left of the chart), the NaOH-buffered guanethidine monosulfate (Ismelin) 10 mg/mL data with 17% isoVUE370 is shown in the data having a square marker with solid line (starting at about 6.3 pH at the bottom left of the chart at the 0.0 on the x-axis), and the Na—OH buffered 10 mg/mL guanethidine hemisulfate in 0.9% saline is shown with the triangle marker and dashed line starting above the 10 pH and at 1.0 along the x-axis, and wherein the Na—OH buffered 10 mg/mL guanethidine hemisulfate in 17% IsoVUE 370 is shown with the circle marker and solid line starting at about the 9.3 pH and at 1.0 along the x-axis.

FIG. 20A depicts an embodiment composition of guanethidine monosulfate that is buffered to increase the pH, for example to an equivalent pH level of guanethidine hemisulfate given the same concentration of the guanethidine molecule in solution. The FIG. 20B depicts guanethidine monosulfate buffering that is possible to reach the pH of guanethidine hemisulfate. The NaOH-buffered guanethidine monosulfate (Ismelin) 10 mg/mL data is shown in the data having a diamond marker with dashed line (starting in the bottom left of the chart), the NaOH-buffered guanethidine monosulfate (Ismelin) 10 mg/mL data with 17% iso-VUE370 is shown in the data having a square marker with solid line (starting at about 6.3 pH at the bottom left of the chart at the –0.0 on the x-axis, and the Na—OH buffered 10 mg/mL guanethidine hemisulfate in 0.9% saline is shown with the triangle marker and dashed line starting above the 10 pH and at 1.0 along the x-axis, and wherein the Na—OH buffered 10 mg/mL guanethidine hemisulfate in 17% Iso-VUE 370 is shown with the circle marker and solid line starting at about the 9.3 pH and at 0.0 along the x-axis.

In this chart, the x-axis depicts the addition of buffer [OH−] molecules or guanethidine [Gnt] molecules to either guanethidine monosulfate (shown to have one [Gnt] molecule for every two [H+] protons) or to guanethidine hemisulfate (shown to have one [Gnt] molecule for every one [H+] proton). In this chart, baseline guanethidine hemisulfate (unbuffered) exists on the x-axis at a value of 1.0, since there is exactly one additional [Gnt] and no [OH−] ions for each [Gnt][H+][H+], while baseline guanethidine monosulfate (unbuffered) exists at a value of 0.0, having no additional [Gnt] molecules nor [OH-] ions. As buffer (in this case, NaOH) is added, the protons are more likely to decouple from the [Gnt] molecule, de-protonating the [Gnt] and increasing its ability to cause nerve destruction when delivered into tissues. The composition of guanethidine monosulfate to reach the same pH in solution as guanethidine hemisulfate at the same concentration requires an equimolar addition of NaOH (or equivalent buffering with known buffers). Either equimolar-buffered guanethidine monosulfate or guanethidine hemisulfate could then be further buffered to further increase the pH of the solution. The addition of contrast medium (in one example, Iso-VUE370) to the composition in a proportion of 17% of the total volume reduces the pH at buffering levels greater than 1.0 on FIG. 20B, leading to a stable pH between 9 and 10 across a broad range of buffer variability (e.g. between 1.0 and 2.0 on the x-axis).

A particular embodiment of buffered guanethidine monosulfate has pH of 10 to 10.5 prior to addition of contrast medium and pH of 9 to 9.5 subsequent to 17% of the volume being replaced by contrast medium. The buffered guanethidine monosulfate is composed of 12 mg/mL guanethidine monosulfate (Gnt.$H_2SO_4$), which is a 40.5 mM solution and an equimolar amount of NaOH (40.5 mM, or 1.6 mg/mL), in 0.7% to 0.90% NaCl solution. When diluted with Iso-VUE370 by 17%, the final composition is created, with 10 mg/mL Gnt.$H_2SO_4$, 0.72% NaCl, 1.35 mg/mL NaOH and 17% IsoVUE370 and a pH of 9 to 9.5. This composition is provided as an example and is not intended to be limiting.

What is claimed is:

1. A method for modulating local tissue physiology comprising:
    injecting a preparation comprising a liquid, gel, or semi-solid into the tissue of a perivascular space beyond an external elastic lamina of a blood vessel;
    buffering the local tissue physiology by raising or lowering the pH of the local tissue with the injected preparation, wherein the preparation comprises a therapeutic agent that has its index effect at a physiological condition modulated by the injection of such preparation, but not having an index effect at a neutral physiological condition; and
    enhancing uptake of the therapeutic agent by the local tissue by the raising or lowering of the pH of the local tissue.

2. The method of claim 1, wherein the therapeutic agent has an additional or enhanced index effect at a physiological condition modulated by the injection of such preparation, but not having such additional or enhanced index effect at the neutral physiological condition.

3. The method of claim 1, wherein the gel comprises a hydrogel that consumes protons as it resorbs in the tissue.

4. The method of claim 1, wherein the preparation includes guanethidine monosulfate, or has a pH>8, or includes guanethidine monosulfate and has a pH>8.

5. The method of claim 3, wherein the hydrogel is alkaline.

6. The method of claim 3, wherein the preparation includes a contrast medium.

7. The method of claim 1, wherein the local tissue physiology comprises a local nerve tissue physiology, and wherein injecting the preparation into the tissue comprises injecting the preparation into local tissue surrounding the nerve.

8. The method of claim 7, wherein the nerve comprises a renal nerve and the blood vessel comprises a renal artery or vein.

9. The method of claim 1, wherein injecting the preparation comprises advancing an injection or infusion catheter through a lumen of the blood vessel to a site near the tissue.

10. The method of claim 9, wherein injecting the preparation further comprises advancing a needle tip from the injection or infusion catheter through one or more of an intima, an internal elastic lamina, a media, or the external elastic lamina of the blood vessel to reach the perivascular space or an adventitia of the blood vessel.

11. The method of claim 10, wherein the needle is advanced in a direction transverse to an inner wall of the blood vessel.

12. The method of claim 1, wherein injecting the preparation comprises introducing an amount of the preparation to the perivascular space sufficient to generate a plume of the preparation surrounding at least a portion of the blood vessel.

13. The method of claim 12, wherein the generated plume diffuses at least one of longitudinally or circumferentially around the blood vessel.

14. The method of claim 12, wherein the generated plume diffuses to reach local tissue surrounding a nerve.

15. The method of claim 14, wherein the nerve comprises a renal nerve and the blood vessel comprises a renal artery or vein.

16. The method of claim 12, further comprising visualizing the plume.

17. The method of claim 1, wherein injecting the preparation comprises generating a therapeutic zone of the tissue, the zone comprising an inner modulated pH zone surrounded by an outer pre-modulated pH zone, wherein enhanced uptake of the therapeutic agent occurs in the modulated pH zone.

18. The method of claim 2, wherein injecting the preparation comprises generating a therapeutic zone of the tissue, the zone comprising an inner modulated pH zone surrounded by an outer pre-modulated pH zone, wherein enhanced uptake of the therapeutic agent occurs in the modulated pH zone.

19. The method of claim 1, wherein injecting the preparation comprises generating a therapeutic zone of the tissue, the zone comprising an inner modulated pH zone surrounded by an outer pre-modulated pH zone, wherein enhanced uptake of a systemically introduced therapeutic agent occurs in the modulated pH zone.

20. The method of claim 1, wherein the preparation buffers local tissue physiology by raising the pH of the local tissue.

21. The method of claim 20, wherein the pH is raised from a neutral physiologic pH of 7.3 to 7.4 to at least 8.

22. The method of claim 20, wherein the preparation displaces interstitial fluid of the local tissue having a neutral physiologic pH.

23. The method of claim 1, further comprising creating a therapeutic agent uptake zone in the local tissue with the injected preparation, wherein the zone comprises a modulated pH as compared to a pre-modulation pH of the local tissue prior to modulation or as compared to a neutral physiologic pH, wherein the zone comprises a gradient of pH that is most modulated at a center of the zone and reduces to the pre-modulation pH of the tissue or to the neutral physiologic pH at an outer edge of the zone, and wherein enhanced uptake of the therapeutic agent occurs in the zone as compared to uptake that would occur into the local tissue at the pre-modulation pH or at the neutral physiologic pH.

* * * * *